United States Patent
Bishop et al.

(10) Patent No.: US 6,300,338 B1
(45) Date of Patent: Oct. 9, 2001

(54) TRICYCLIC CARBAMATE COMPOUNDS USEFUL FOR INHIBITION OF G-PROTEIN FUNCTION AND FOR TREATMENT OF PROLIFERATIVE DISEASES

(75) Inventors: W. Robert Bishop, Pompton Plains; Ronald J. Doll, Maplewood; Alan K. Mallams, Long Valley; F. George Njoroge, Union; Joanne M. Petrin, Cedar Grove; John J. Piwinski, Clinton Township; Ronald L. Wolin, Westfield; Arthur G. Taveras, Rockaway; Stacy W. Remiszewski, Township of Washington, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/348,916

(22) Filed: Jul. 7, 1999

Related U.S. Application Data

(62) Division of application No. 08/971,099, filed on Nov. 14, 1997, now Pat. No. 5,977,128, which is a division of application No. 08/410,479, filed on Mar. 24, 1995, now Pat. No. 5,721,236, which is a continuation-in-part of application No. 08/312,030, filed on Sep. 26, 1994, now abandoned, which is a continuation-in-part of application No. 08/137,435, filed on Oct. 15, 1993, now abandoned.

(51) Int. Cl.[7] ....................... A61K 31/435; C07D 401/04
(52) U.S. Cl. ............................ 514/290; 546/93; 544/361
(58) Field of Search ................................ 514/290; 546/93

(56) References Cited

U.S. PATENT DOCUMENTS 4,282,233    8/1981    Villani .................... 546/93

(List continued on next page.)

FOREIGN PATENT DOCUMENTS 0042544    12/1981    (EP).

(List continued on next page.)

OTHER PUBLICATIONS

*Cell*, 65, 1–4 (1991).

(List continued on next page.)

*Primary Examiner*—Alan L. Rotman
(74) *Attorney, Agent, or Firm*—Henry C. Jeanette

(57) ABSTRACT

A method of inhibiting Ras function and therefore inhibiting cellular growth is disclosed. The method comprises the administration of a compound of Formula 1.0

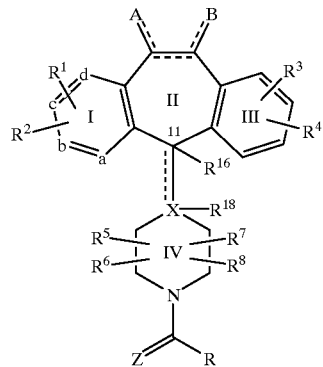

(1.0)

Also disclosed are novel compounds of the formulas:

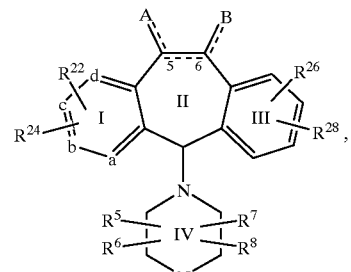

(1.1)

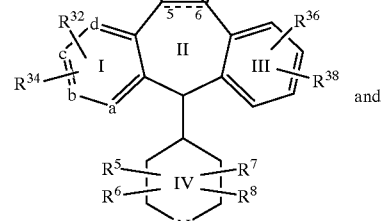

(1.2)

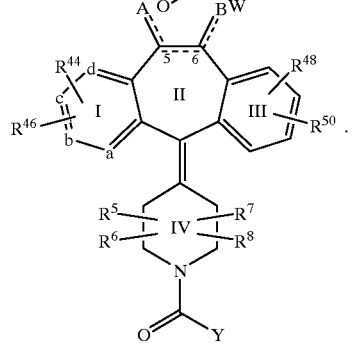

(1.3)

Also disclosed are processes for making 3-substituted compounds of the Formulas 1.1, 1.2 and 1.3.
Further disclosed are novel compounds which are intermediates in the processes for making the 3-substituted compounds of Formulas 1.1, 1.2, and 1.3.

14 Claims, No Drawings

U.S. PATENT DOCUMENTS

| | | |
|---|---|---|
| 4,826,853 | 5/1989 | Piwinski et al. ............... 514/253.03 |
| 4,831,042 | 5/1989 | Villani ............................... 514/316 |
| 4,863,931 | 9/1989 | Schumacher et al. ............ 514/290 |
| 5,089,496 | 2/1992 | Piwinski et al. .................. 514/254 |
| 5,104,876 | 4/1992 | Piwinski et al. .................. 514/254 |
| 5,141,851 | 8/1992 | Brown et al. ...................... 435/15 |
| 5,151,423 | 9/1992 | Piwinski et al. .................. 514/254 |
| 5,721,236 * | 2/1998 | Bishop et al. ..................... 514/255 |
| 5,728,703 * | 3/1998 | Bishop et al. ..................... 514/254 |
| 5,977,128 * | 11/1999 | Bishop et al. ..................... 514/290 |

FOREIGN PATENT DOCUMENTS

| | | |
|---|---|---|
| 0270818 | 6/1988 | (EP) . |
| 0495484 | 7/1992 | (EP) . |
| 0535730 | 4/1993 | (EP) . |
| WO 88/03138 | 5/1988 | (WO) . |
| WO 89/10363 | 11/1989 | (WO) . |
| WO 90/13548 | 11/1990 | (WO) . |
| WO 92/00293 | 1/1992 | (WO) . |
| WO 92/11034 | 7/1992 | (WO) . |
| WO 94/04561 | 3/1994 | (WO) . |
| WO 94/24107 | 10/1994 | (WO) . |

OTHER PUBLICATIONS

*J. Biol. Chem.*, 266, (24) 15575–15578 (1991).
*Proc. Natl. Acad. Sci. USA*, 87, 3042–3046 (1990).
*Proc. Natl. Acad. Sci. USA*, 88, 8631–8635 (1991).
*Nature*, 356, 713–715 (1992).
*Proc. Natl. Acad. Sci. USA*, 87, 7926–7929 (1990).
*J. Biol. Chem.*, 265, (25) 14701–14704 (1990).
*Proc. Natl. Acad. Sci. USA*, 87, 7926–7929 (1990).
*Cell*, 62, 81–88 (1990).
*Biochemistry*, 31, 3800–3807.
*Science*, 260, 1934–1937.
*Science*, 260, 1937–1942.
*J. Med. Chem.*, 34, 457–461 (1991).
Chem. Abstracts No. 121:53129x (1994) for WO 94/04561.
Masci, *J. Chem. Soc., Chem. Commun.*, 1262–1263 (1992).
Masci, *J. Org. Chem.*, 50, 4081–4087 (1985).
Sebti, et al., *Proc. Ann. Meeting AM Assoc. Cancer Res.*, 33:A2217 (1992).
Villani, et al., *J. Med. Chem.*, 15(7) 750–754 (1972).
Billah, et al., *Lipids*, 26, (12) 1172–1174.
Villani, et al., *Arzneim–Forsch./Drug Res.*, 36(11), 1311–1314 (1986).

* cited by examiner

TRICYCLIC CARBAMATE COMPOUNDS USEFUL FOR INHIBITION OF G-PROTEIN FUNCTION AND FOR TREATMENT OF PROLIFERATIVE DISEASES

REFERENCE TO RELATED APPLICATIONS

This is a division of application Ser. No. 08/971,099 filed Nov. 14, 1997 (now U.S. Pat. No. 5,977,128 issued on Nov. 2, 1999), which in turn is a division of application Ser. No. 08/410, 479 filed Mar. 24, 1995 (now U.S. Pat. No. 5,721, 236 issued Feb. 24, 1998), which in turn is a continuation-in-part of application Ser. No. 08/312,030 filed on Sep. 26, 1994 (abandoned), which in turn is a continuation-in-part of application Ser. No. 08/137,435 filed Oct. 15, 1993 (abandoned).

BACKGROUND

International Publication Number WO92/11034, published Jul. 9, 1992, discloses a method of increasing the sensitivity of a tumor to an antineoplastic agent, which tumor is resistant to the antineoplastic agent, by the concurrent administration of the antineoplastic agent and a potentiating agent of the formula:

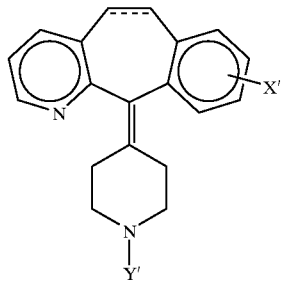

wherein the dotted line represents an optional double bond, X' is hydrogen or halo, and Y' is hydrogen, substituted carboxylate or substituted sulfonyl. For example, Y' can be, amongst others, —COOR' wherein R' is C1 to C6 alkyl or substituted alkyl, phenyl, substituted phenyl, C7 to C12 aralkyl or substituted aralkyl or -2, -3, or -4 piperidyl or N-substituted piperidyl. Y' can also be, amongst others, $SO_2R'$ wherein R' is C1 to C6 alkyl, phenyl, substituted phenyl, C7 to C12 aralkyl or substituted aralkyl. Examples of such potentiating agents include 11-(4-piperidylidene)-5H-benzo[5,6]cyclohepta[1,2-b]pyridines such as Loratadine.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors in which Ras contributes to transformation. Mutated; oncogenic forms of ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras. One compound disclosed in this invention has been demonstrated to have anti-tumor activity in animal models.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Compounds useful in the claimed methods are represented by Formula 1.0:

(1.0)

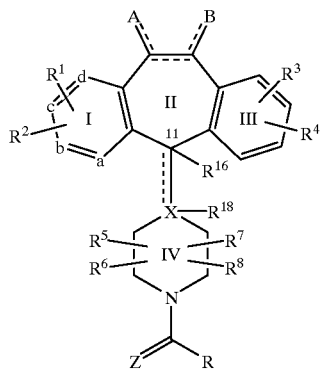

or a pharmaceutically acceptable salt or solvate thereof, wherein:

one of a, b, c and d represents N or $NR^9$ wherein $R^9$ is O—, —$CH_3$ or —$(CH_2)_nCO_2H$ wherein n is 1 to 3, and the remaining a, b, c and d groups represent $CR^1$ or $CR^2$;

each $R^1$ and each $R^2$ is independently selected from H, halo, —$CF_3$, —$OR^{10}$ (e.g. —OH), —$COR^{10}$, —$SR^{10}$, —$N(R^{10})_2$, —$NO_2$, —$OC(O)R^{10}$, —$CO_2R^{10}$, —$OCO_2R^{11}$, benzotriazol-1-yloxy, CN, alkynyl, alkenyl or alkyl, said alkyl or alkenyl group optionally being substituted with halo, —$OR^{10}$ or —$CO_2R^{10}$;

$R^3$ and $R^4$ are the same or different and each independently represents H, any of the substituents of $R^1$ and $R^2$, or $R^3$ and $R^4$ together can represent a saturated or unsaturated $C_5$–$C_7$ fused ring to the benzene ring (Ring III);

$R^5$, $R^6$, $R^7$ and $R^8$ each independently represents H, —$CF_3$, alkyl or aryl, said alkyl or aryl optionally being substituted with —OR$^{10}$, —SR$^{10}$, —N(R$^{10}$)$_2$, —NO$_2$, —COR$^{10}$, —OCOR$^{10}$, —OCO$_2$R$^{11}$, —CO$_2$R$^{10}$, OPO$_3$R$^{10}$ or one of R$^5$, R$^6$, R$^7$ and R$^8$ can be taken in combination with R as defined below to represent —(CH$_2$)$_r$— wherein r is 1 to 4 which can be substituted with lower alkyl, lower alkoxy, —CF$_3$ or aryl;

R$^{10}$ represents H, alkyl, aryl, or aralkyl (preferably benzyl);

R$^{11}$ represents alkyl or aryl;

R$^{16}$ and R$^{18}$ represent H and F respectively, or F and H respectively, when the bond to X is a single bond and X is carbon, preferably R$^{16}$ is F and R$^{18}$ is H; or R$^{16}$ and R$^{18}$ each represent H when the bond to X is a single bond;

X represents N or C, which C may contain an optional double bond (represented by the dotted line) to carbon atom 11;

the dotted line between carbon atoms 5 and 6 represents an optional double bond, such that when a double bond is present, A and B independently represent —R$^{10}$, halo, —OR$^{11}$, —OCO$_2$R$^{11}$ or —OC(O)R$^{10}$, and when no double bond is present between carbon atoms 5 and 6, A and B each independently represent H$_2$, —(OR$^{11}$)$_2$; H and halo, dihalo, alkyl and H, (alkyl)$_2$, —H and —OC(O)R$^{10}$, H and —OR$^{10}$, =O, aryl and H, =NOR$^{10}$ or —O—(CH$_2$)$_p$—O— wherein p is 2, 3 or 4;

Z represents O; and

R represents —SR$^{65}$ wherein R$^{65}$ is alkyl, aryl, heteroaryl (e.g. pyridyl or pyridyl N-oxide), 2-,3-, or 4-piperidyl or N-substituted piperidyl, wherein the substituent on said N-substituted piperidyl is C$_1$ to C$_4$ alkyl, alkylcarbonyl or —C(O)NH(R$^{10}$) wherein R$^{10}$ is H or alkyl; or R represents —OR$^{20}$ wherein R$^{20}$ is C$_1$ to C$_{12}$ alkyl, substituted C$_1$ to C$_{12}$ alkyl, phenyl, substituted phenyl, C$_7$ to C$_{12}$ phenylalkyl (e.g., benzyl), C$_7$ to C$_{12}$ phenylalkyl wherein the phenyl moiety is substituted, heteroaryl (e.g., pyridyl or pyridyl N-oxide), or R$^{20}$ is -2, -3, or -4 piperidyl or N-substituted piperidyl, wherein the substituents on said substituted C$_1$ to C$_{12}$ alkyl are selected from amino or substituted amino, with the proviso that said amino or said substituted amino for said C$_1$ to C$_{12}$ alkyl is not on C$_1$, and the substitutents on said substituted amino are selected from C$_1$ to C$_6$ alkyl, the substituents on said substituted phenyl and on said substituted phenyl moiety of the C$_7$ to C$_{12}$ phenylalkyl are selected from C$_1$ to C$_6$ alkyl and halo, and the substituent on said N-substituted piperidyl is C to C$_4$ alkyl, alkylcarbonyl (e.g., CH$_3$C(O)—) or —C(O)NH(R$^{10}$) wherein R$^{10}$ is H or alkyl.

This invention also provides novel compounds of Formula 1.1:

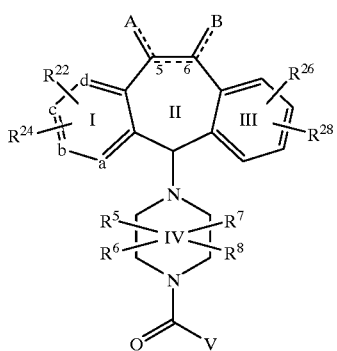

(1.1)

or a pharmaceutically acceptable salt or solvate thereof, wherein:

a, b, c, d, A, B, R$^5$, R$^6$, R$^7$, and R$^8$ are as defined for Formula 1.0;

R$^{22}$ and R$^{24}$ are the same or different and each independently represents any of the substituents of R$^1$ and R$^2$;

R$^{26}$ and R$^{28}$ are the same or different and each independently represents any of the substituents of R$^3$ and R$^4$;

V represents —OR$^{30}$ or —SR$^{70}$;

R$^{30}$ represents aralkyl (e.g., benzyl), aryl (e.g., phenyl or substituted phenyl—i.e., phenyl substituted with 1 to 3, preferably 1, group selected from halo, alkyl, haloalkyl or alkoxy), heteroaryl (e.g., pyridyl, such as 3- or 4-pyridyl, or pyridyl N-oxide, such as 3- or 4-pyridyl N-oxide), alkyl (e.g., ethyl), or -2, -3, or -4 piperidyl or N-substituted piperidyl, wherein the substituents on said N-substituted piperidyl is C$_1$ to C$_4$ alkyl, alkylcarbonyl (e.g., CH$_3$C(O)—) or —C(O)NH(R$^{10}$) wherein R$^{10}$ is H or alkyl;

R$^{70}$ represents aryl (e.g., phenyl or substituted phenyl— i.e., phenyl substituted with 1 to 3, preferably 1, group selected from halo, alkyl, haloalkyl or alkoxy), heteroaryl (e.g., pyridyl, such as 3- or 4-pyridyl, or pyridyl N-oxide, such as 3- or 4-pyridyl N-oxide), or 2-,3-, or 4-piperidyl or N-substituted piperidyl, wherein the substituent on said N-substituted piperidyl is C$_1$ to C$_4$ alkyl, alkylcarbonyl or —C(O)NH(R$^{10}$) wherein R$^{10}$ is H or alkyl; and the dotted line between carbons 5 and 6 represent an optional double bond (preferably the double bond is absent).

This invention further provides novel compounds of Formula 1.2:

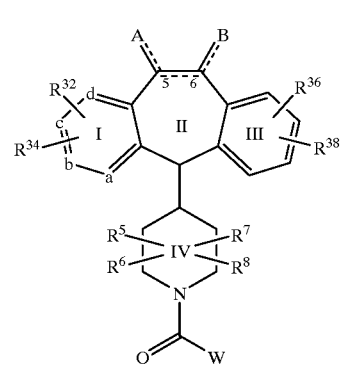

(1.2)

or a pharmaceutically acceptable salt or solvate thereof, wherein:

a, b, c, d, A, B, R$^5$, R$^6$, R$^7$, and R$^8$ are as defined for Formula 1.0;

R$^{32}$ and R$^{34}$ are the same or different and each independently represents any of the substituents of R$^1$ and R$^2$;

R$^{36}$ and R$^{38}$ are the same or different and each independently represents any of the substituents of R$^3$ and R$^4$;

W represents —OR$^{40}$ or —SR$^{70}$;

R$^{40}$ represents alkyl (e.g., ethyl), aryl (e.g., phenyl or substituted phenyl—i.e., phenyl substituted with 1 to 3, preferably 1, group selected from halo, alkyl, haloalkyl or alkoxy), heteroaryl (e.g., pyridyl, such as 3- or 4-pyridyl, or pyridyl N-oxide, such as 3- or 4-pyridyl N-oxide), or -2, -3, or -4 piperidyl or N-substituted piperidyl, wherein the substituents on said N-substituted piperidyl is C$_1$ to C$_4$ alkyl, alkylcarbonyl (e.g., CH$_3$C(O)—) or —C(O)NH(R$^{10}$) wherein R$^{10}$ is H or alkyl;

$R^{70}$ is as defined above; and the dotted line between carbons 5 and 6 represent an optional double bond.

This invention additionally provides compounds of Formula 1.3:

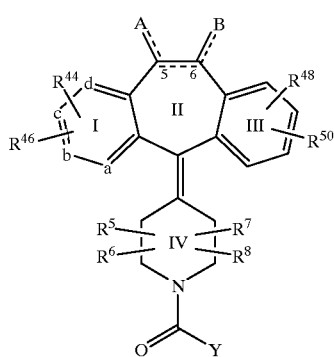

(1.3)

a, b, c, d, A, B, $R^5$, $R^6$, $R^7$, and $R^8$ are as defined for Formula 1.0;

$R^{44}$ and $R^{46}$ are the same or different and each independently represents any of the substituents of $R^1$ and $R^2$;

$R^{48}$ and $R^{50}$ are the same or different and each independently represents any of the substituents of $R^3$ and $R^4$;

Y represents —$OR^{52}$ or —$SR^{70}$;

$R^{52}$ represents aralkyl (e.g., benzyl), aryl (e.g., phenyl or substituted phenyl—i.e., phenyl substituted with 1 to 3, preferably 1, group selected from halo, alkyl, haloalkyl or alkoxy), heteroaryl (e.g., pyridyl, such as 3- or 4-pyridyl, or pyridyl N-oxide, such as 3- or 4-pyridyl N-oxide), alkyl (e.g., ethyl), or -2, -3, or -4 piperidyl or N-substituted piperidyl, wherein the substituents on said N-substituted piperidyl is $C_1$ to $C_4$ alkyl, alkylcarbonyl (e.g., $CH_3C(O)$—) or —$C(O)NH(R^{10})$ wherein $R^{10}$ is H or alkyl;

$R^{70}$ is as defined above; and the dotted line between carbons 5 and 6 represent an optional double bond (preferably the double bond is absent); and with the provisos that: (a) when Y represents —$OR^{52}$, and when there is a single bond between carbon atoms 5 and 6, and when both $R^{44}$ and $R^{46}$ are hydrogen, and when both $R^{48}$ and $R^{50}$ are H, then $R^{52}$ is not phenyl; and (b) when Y represents —$OR^{52}$, and when there is a single bond between carbon atoms 5 and 6, and when both $R^{44}$ and $R^{46}$ are hydrogen, and when $R^{48}$ is Cl at the C-8 position and $R^{50}$ is H, then $R^{52}$ is not ethyl.

This invention also provides a method for inhibiting tumor growth by administering an effective amount of the tricyclic compounds, described herein, to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, bladder carcinoma, and myelodysplastic syndrome (MDS).

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, lyn, fyn), may be inhibited by the tricyclic compounds described herein.

The compounds of this invention inhibit farnesyl protein transferase and the farnesylation of the oncogene protein Ras. This invention further provides a method of inhibiting ras farnesyl protein transferase, in mammals, especially humans, by the administration of an effective amount of the tricyclic compounds described above. The administration of the compounds of this invention to patients, to inhibit farnesyl protein transferase, is useful in the treatment of the cancers described above.

The tricyclic compounds useful in the methods of this invention inhibit abnormal cellular growth. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

This invention also provides a process for producing 3-nitro substituted compounds. The process comprises reacting one molar equivalent of a compound:

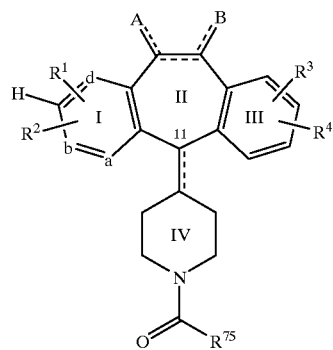

(1.0g)

wherein $R^1$, $R^2$, $R^3$, $R^4$, A, B, a, b, d, and the dotted lines are as defined for Formula 1.0; and $R^{75}$ represents H or —$OR^{76}$ wherein $R^{76}$ represents alkyl (e.g., $C_1$ to $C_4$ alkyl, preferably ethyl); with one molar equivalent of a nitrating reagent, said nitrating reagent being preformed (i.e., prepared first) by mixing, at cold temperature (e.g., at 0° C.) equimolar amounts of tetrabutyl ammonium nitrate with trifluoroacetic anhydride; the reaction of the nitrating reagent with the compound of Formula 1.0g taking place in a suitable aprotic solvent (e.g., methylene chloride, chloroform, toluene or THF); said reaction with said nitrating reagent being conducted at a temperature and for a period of time sufficient to allow the reaction to proceed at a reasonable rate to produce the desired final 3-nitro compound of Formula 1.0h (described below)—i.e., the reaction of the compound of Formula 1.0g with said nitrating reagent is conducted at an intial temperature of 0° C., and said reaction temperature is thereafter allowed to rise to about 25° C. during the reaction time period. The reaction usually proceeds overnight to completion, i.e., the reaction usually proceeds for about 16 hours. The reaction can be conducted within a temperature of 0° C. to about 25° C. during a time period of about 10 to about 24 hours. Preferably the reaction is initially conducted at 0° C. and the temperature is allowed to warm up to 25° C. The reaction produces the 3-nitro compound:

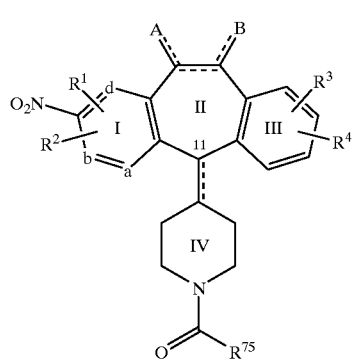

(1.0h)

is produced.

The compound of Formula 1.0h can then be converted to other 3-substituted products by methods well known to those skilled in the art. For example, the 3-nitro compounds can be converted to 3-amino, 3-halo, 3-cyano, 3-alkyl, 3-aryl, 3-thio, 3-arylalkyl, 3-hydroxyl, and 3-$OR^{77}$ wherein $R^{77}$ is alkyl or aryl. The 3-substituted compounds can then be converted to final products by the procedures described herein.

This invention also provides a process for producing 3-nitro compounds of the formula:

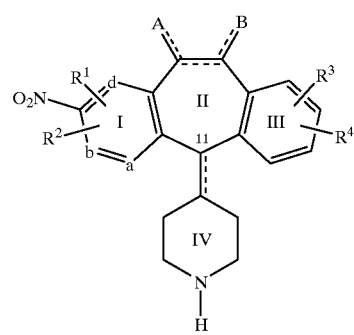

(1.0i)

by producing a compound of Formula 1.0h from 1.0g as described above; and then hydrolyzing the compound of Formula 1.0h by dissolving the compound of Formula 1.0h in a sufficient amount of concentrated acid (e.g., concentrated HCl or aqueous sulfuric acid), and heating the resulting mixture to a temperature sufficient to remove (hydrolyze) the —C(O)$R^{75}$ substituent, for example, heating to reflux or to a temperature of about 100° C.

The compound of Formula 1.0i can then be converted to other 3-substituted compounds as discussed above for the compounds of Formula 1.0h. The compounds of Formula 1.0i can then be converted to compounds of this invention by the methods described herein.

This invention also provides a process for producing compounds of the formula:

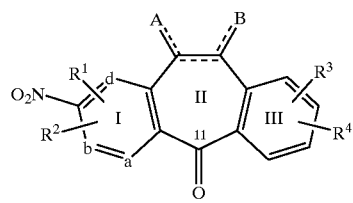

(1.0j)

by reacting one molar equivalent a compound of formula:

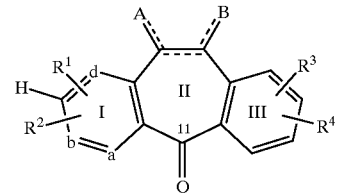

(1.0k)

with one molar equivalent of a nitrating reagent, said nitrating reagent being preformed (i.e., prepared first) by mixing, at cold temperature (e.g., at 0° C.) equimolar amounts of tetrabutyl ammonium nitrate with trifluoroacetic anhydride; the reaction of the nitrating reagent with the compound of Formula 1.0k taking place in a suitable aprotic solvent (e.g., methylene chloride, chloroform, toluene or THE); said reaction with said nitrating reagent being conducted at a temperature and for a period of time sufficient to allow the reaction to proceed at a reasonable rate to produce the desired final 3-nitro compound of Formula 1.0j—i.e., the reaction of the compound of Formula 1.0k with said nitrating reagent is conducted at an intial temperature of 0° C., and said reaction temperature is thereafter allowed to rise to about 25° C. during the reaction time period. The reaction usually proceeds overnight to completion, i.e., the reaction usually proceeds for about 16 hours. The reaction can be conducted within a temperature of 0° C. to about 25° C. during a time period of about 10 to about 24 hours. Preferably the reaction is initially conducted at 0° C. and the temperature is allowed to warm up to 25° C. In Formulas 1.0j and 1.0k, $R^1$, $R^2$, $R^3$, $R^4$, A, B, a, b, d, and the dotted lines are as defined for Formula 1.0

The compounds of Formula 1.0j can be converted to compounds of Formula 1.0h by methods described below. Also, as discussed above for the compounds of Formula 1.0h, the compounds of Formula 1.0j can be converted to other 3-substituted compounds wherein the substituents are those discussed above for Formula 1.0h.

The compounds of Formula 1.0j can be converted to compounds of Formula 1.0m:

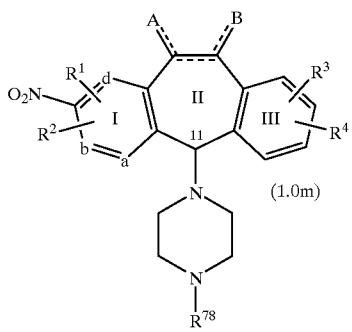

(1.0m)

wherein $R^{78}$ is H or —COOR$^a$ wherein $R^a$ is a $C_1$ to $C_3$ alkyl group (preferably $R^{78}$ is H), by reducing a compound of Formula 1.0j with a suitable reducing agent (such as sodium borohydride) in a suitable solvent (such as EtOH or MeOH) at a suitable temperature to allow the reaction to proceed at a reasonable rate (e.g., 0 to about 25° C.); reacting the resulting product (Formula 1.0j wherein the =O has been reduced to a —OH) with a chlorinating agent (e.g., thionyl chloride) in an suitable organic solvent (e.g., benzene, toluene or pyridine) at a suitable temperature to allow the reaction to proceed at a reasonable rate (e.g., about −20 to about 20° C., preferably at −15° C.) to produce a compound of Formula 1.0n:

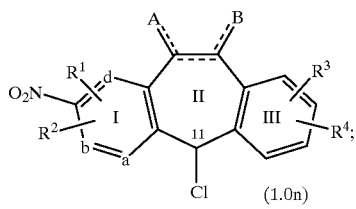

and reacting a compound of Formula 1.0n with a compound of the formula:

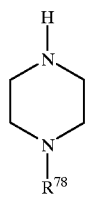

wherein $R^{78}$ is as previously defined, and is preferably H, in a suitable organic solvent (such as THF or toluene) containing a suitable base (such as triethylamine or N-methylmorpholine) at a suitable temperature to allow the reaction to proceed at a reasonable rate (e.g., 25 to about 120° C.).

Compounds of Formula 1.0m can be converted to compounds of this invention by the methods disclosed herein. Also, as discussed above for the compounds of Formula 1.0h, the compounds of Formula 1.0m can be converted to other 3-substituted compounds wherein the substituents are those discussed above for Formula 1.0h.

This invention also provides novel compounds (produced in the above described processes as intermediates to the compounds of this invention) having the formulas:

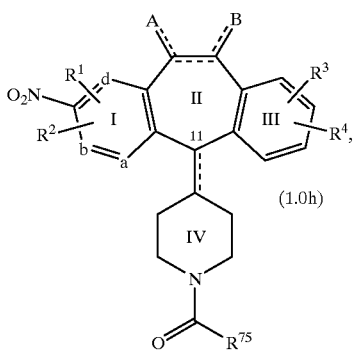

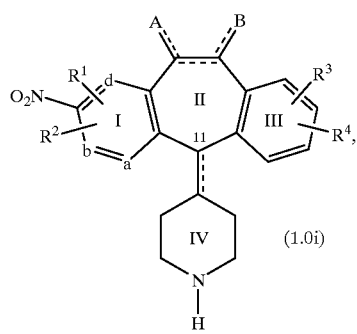

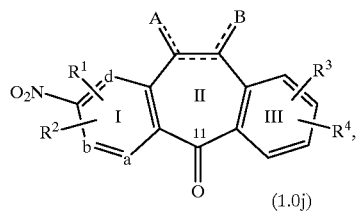

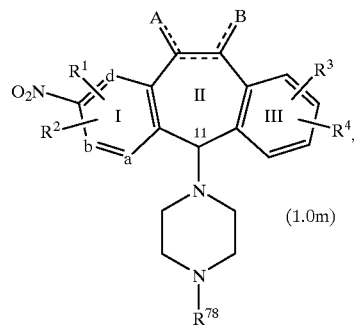

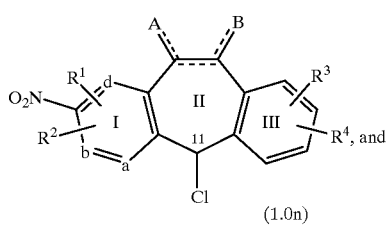

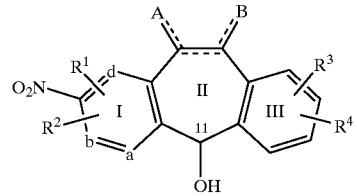

wherein all substituents are as defined herein.

Preferably, for the intermediate compounds of the processes of this invention, $R^1$ and $R^2$ are H; $R^3$ is halo, most preferably Cl, in the C-8 position; $R^4$ is H; and A and B are H when the double between C-5 and C-6 is present, and A and B are $H_2$ when the bond between C-5 and C-6 is a single bond (most preferably the bond between C-5 and C-6 is a single bond). Those skilled in the art will appreciate that Rings I, II, and/or III can be further substituted, as described herein, to produce the desired compounds of the invention.

Examples of such novel intermediate compounds include:

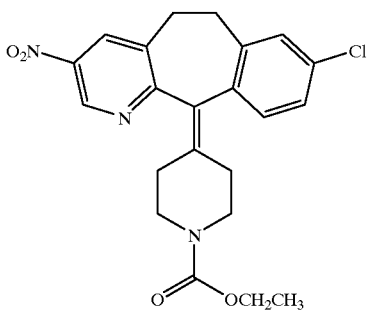

and

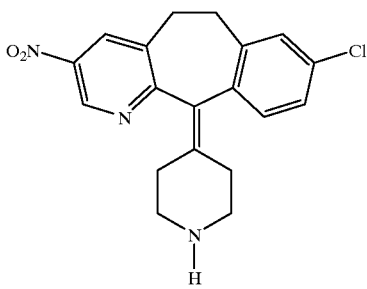

DETAILED DESCRIPTION OF THE INVENTION

As used herein, the following terms are used as defined below unless otherwise indicated:

$M^+$-represents the molecular ion of the molecule in the mass spectrum;

$MH^+$-represents the molecular ion plus hydrogen of the molecule in the mass spectrum;

alkyl-(including the alkyl portions of alkoxy, alkylamino and dialkylamino)-represents straight and branched carbon chains and contains from one to twenty carbon atoms, preferably one to six carbon atoms;

alkanediyl-represents a divalent, straight or branched hydrocarbon chain having from 1 to 20 carbon atoms, preferably 1 to 6 carbon atoms, the two available bonds being from the same or different carbon atoms thereof, e.g., methylene, ethylene, ethylidene, —$CH_2CH_2CH_2$—, —$CH_2CHCH_3$, —$CHCH_2CH_3$, etc.

cycloalkyl-represents saturated carbocyclic rings branched or unbranched of from 3 to 20 carbon atoms, preferably 3 to 7 carbon atoms;

heterocycloalkyl-represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —$NR^{10}$— (suitable heterocycloalkyl groups including 2- or 3-THFyl, 2- or 3-tetrahydrothienyl, 2-, 3- or 4-piperidinyl, 2- or 3-pyrrolidinyl, 2- or 3-piperizinyl, 2- or 4-dioxanyl, etc.);

alkenyl-represents straight and branched carbon chains having at least one carbon to carbon double bond and containing from 2 to 12 carbon atoms, preferably from 2 to 6 carbon atoms and most preferably from 3 to 6 carbon atoms;

alkynyl-represents straight and branched carbon chains having at least one carbon to carbon triple bond and containing from 2 to 12 carbon atoms, preferably from 2 to 6 carbon atoms;

aryl (including the aryl portion of aryloxy and aralkyl)-represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, $CF_3$, amino, alkylamino, dialkylamino, —$COOR^{10}$ or —$NO_2$; and halo-represents fluoro, chloro, bromo and iodo; and heteroaryl-represents cyclic groups, optionally substituted with $R^3$ and $R^4$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., 2-, 3- or 4-pyridyl (optionally substituted with $R^3$ and $R^4$) and pyridyl N-oxide:

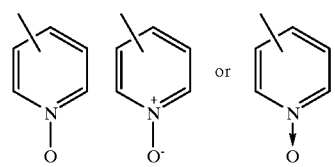

(e.g., 2-, 3- or 4-pyridyl N-oxide, optionally substituted with $R^3$ and $R^4$).

Reference to the positions of the substituents in Rings I and III, for example, is based on the numbered ring structure:

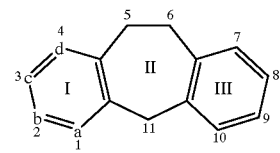

For example, in Formula 1.0, $R^1$ can be at the C-4 position and $R^2$ can be at the C-2 or C-3 position. Also, for example, $R^3$ can be at the C-8 position and $R^4$ can be at the C-9 position.

Representative structures of Formula 1.0 include but are not limited to:

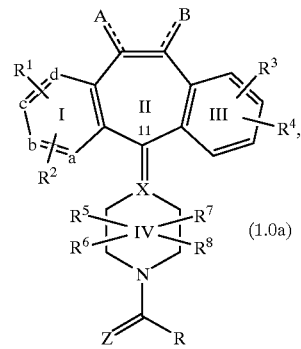

(1.0a)

-continued

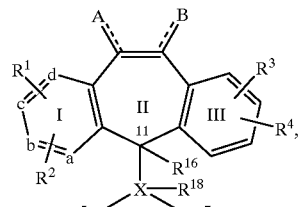

(1.0b)

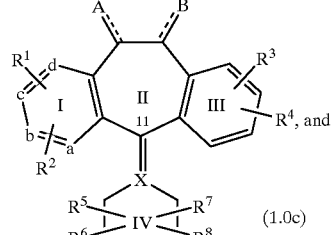

(1.0c)

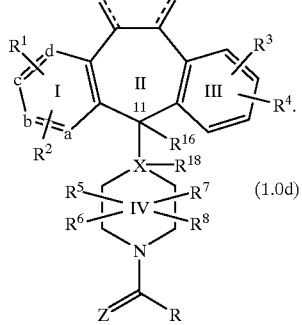

(1.0d)

Preferably, for the compounds of Formula 1.0 (including 1.0a to 1.0d):

- one of a, b, c and d (most preferably a) represents N or $NR^9$ wherein $R^9$ is O— or —$CH_3$, and the remaining a, b, c and d groups represent $CR^1$ or $CR^2$; more preferably a represents N and the remaining a, b, c and d groups represent $CR^1$ or $CR^2$;
- each $R^1$ and each $R^2$ is independently selected from H, halo, (e.g. Cl or Br) benzotriazol-1yloxy or alkyl (most preferably $C_1$ to $C_4$ alkyl, more preferably methyl); most preferably $R^1$ and $R^2$ are selected from H or halo; and more preferably $R^1$ and $R^2$ are selected from H, Cl or Br;
- $R^3$ and $R^4$ are the same or different and each independently represents H, halo or alkyl; most preferably $R^3$ is halo and $R^4$ is H; more preferably $R^3$ is Cl and $R^4$ is H; even more preferably $R^3$ is Cl at the C-8 position and $R^4$ is H;
- $R^5$, $R^6$, $R^7$ and $R^8$ each independently represents H or alkyl; and most preferably $R^5$, $R^6$, $R^7$ and $R^8$ each represents H;
- the dotted line between carbon atoms 5 and 6 represents an optional double bond, such that when a double bond is present, A and B independently represent H, —$R^{10}$ or —$OR^{10}$, and most preferably H, and when no double bond is present between carbon atoms 5 and 6, A and B each independently represent $H_2$, —$(OR^{10})_2$, (alkyl and H), (alkyl)$_2$, (—H and —$OR^{10}$) or =O, and most preferably $H_2$; and
- $R^{20}$ is $C_1$ to $C_{12}$ alkyl, phenyl, substituted phenyl, $C_7$ to $C_{12}$ phenylalkyl (e.g., benzyl), $C_7$ to $C_{12}$ phenylalkyl wherein the phenyl moiety is substituted, 3- or 4-N-substituted piperidyl, or heteroaryl (e.g., pyridyl or pyridyl N-oxide), wherein the substituents on said substituted phenyl and on said substituted phenyl moiety of the $C_7$ to $C_{12}$ phenylalkyl are selected from $C_1$ to $C_6$ alkyl and halo, and wherein the substituents on said N-substituted piperidyl is $C_1$ to $C_4$ alkyl (most preferably methyl), alkylcarbonyl (e.g., $CH_3C(O)$—) or —$C(O)NH(R^{10})$ wherein $R^{10}$ is H or alkyl; most preferably $R^{20}$ is $C_1$ to $C_6$ alkyl (more preferably ethyl), phenyl, substituted phenyl, 3-pyridyl, 3-pyridyl N-oxide, 4-pyridyl, 4-pyridyl N-oxide, or 3- or 4-N-substituted piperidyl wherein the substituent on the nitrogen is $C_1$ to $C_4$ alkyl (more preferaby methyl).

Preferably, for the compounds of Formula 1.0, R represents —$OR^{20}$, with the remaining substituents being as defined above.

Tricyclic compounds useful in the methods of this invention are described in: (1) U.S. Pat. No. 4,282,233; (2) U.S. Pat. No. 4,826,853; (3) WO 88/03138 published on May 5, 1988 (PCT/US87/02777); and (4) U.S. Pat. No. 4,863,931; the disclosures of each being incorporated herein by reference thereto.

Compounds of Formula 1.1 include compounds of the formulas:

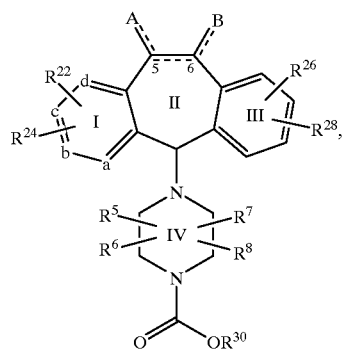

(1.1A)

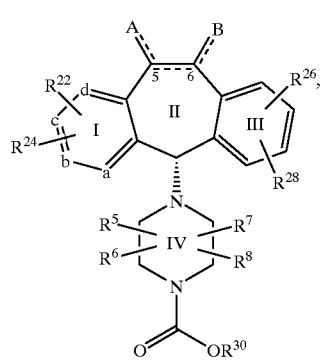

(1.1B)

(1.1C)
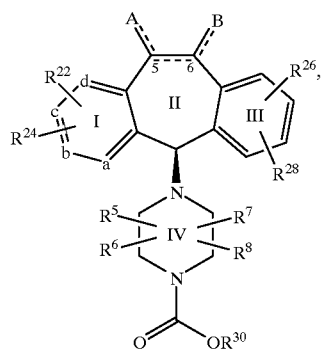

(1.1D)
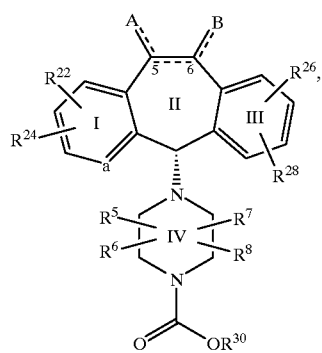

(1.1E)
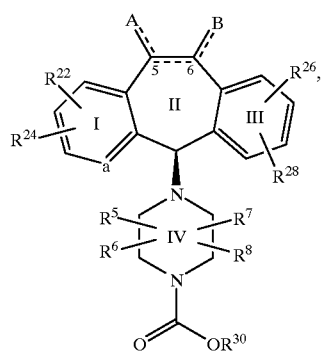

(1.1F)
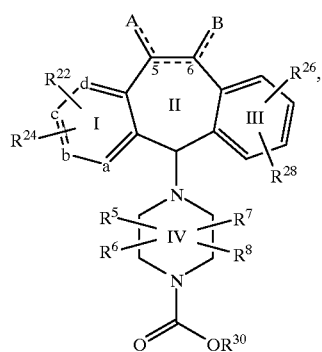

and (1.1G)
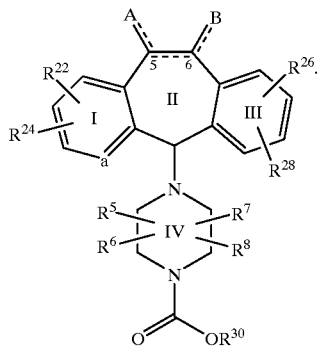

Preferably for compounds of Formula 1.1:

a represents N, and b, c, and d represent carbon;

A and B each represent $H_2$ when the double bond between C-5 and C-6 is absent, and A and B each represent H when the double bond is present;

$R^5$, $R^6$, $R^7$, and $R^8$ each represent H;

$R^{22}$ and $R^{24}$ are each independently selected from H, halo (e.g., Cl or Br), benzotriazol-1yloxy or alkyl (most preferably $C_1$ to $C_4$ alkyl, more preferably methyl); most preferably $R^{22}$ and $R^{24}$ are each independently selected from H or halo; more preferably $R^{22}$ and $R^{24}$ are each independently selected from H, Cl or Br;

$R^{26}$ and to $R^{28}$ are each independently selected from H, halo (e.g, Cl or Br) or alkyl, most preferably $R^{26}$ is halo and $R^{28}$ is H, more preferably $R^{26}$ is Cl and $R^{28}$ is H, even more preferably $R^{26}$ is Cl at the C-8 position and $R^{28}$ is H;

V represents —$OR^{30}$; and $R^{30}$ represents aryl (e.g., phenyl), heteroaryl (e.g., pyridyl, such as 3- or 4-pyridyl, and pyridyl N-oxide, such as 3- or 4-pyridyl N-oxide), alkyl (e.g., ethyl), or 3- or 4-N-substituted piperidyl (most preferably the substituent on said N-substituted piperidyl is $C_1$ to $C_4$ alkyl, and more preferaby methyl).

For example compounds of Formula 1.1 include:

(1.1H)
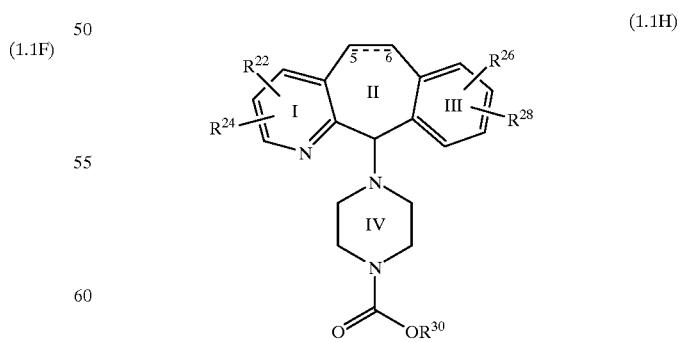

wherein the substituents are as defined above.

Representative examples of compounds of Formula 1.2 include:

(1.2A)
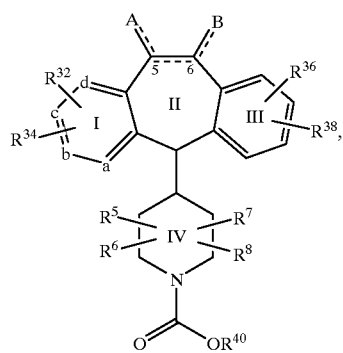

(1.2B)
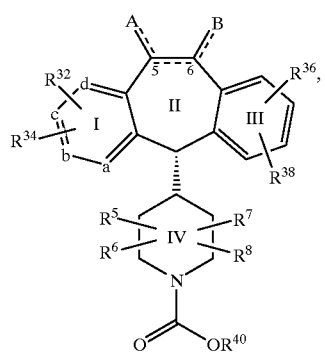

(1.2C)
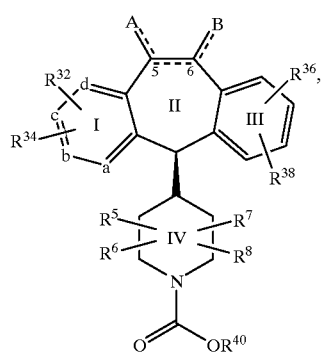

(1.2D)
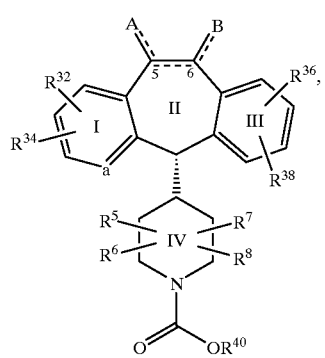

-continued (1.2E)
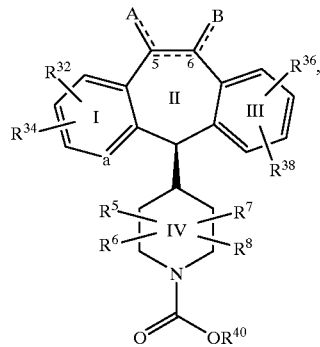

(1.2F)
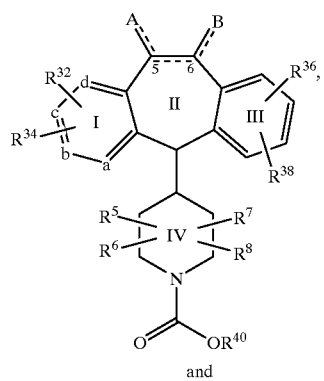

and (1.2G)
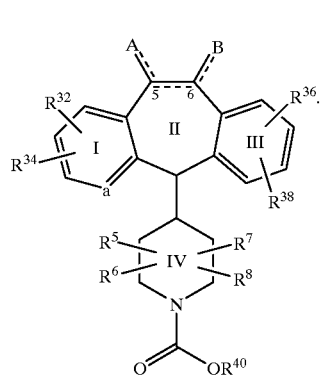

Preferably for compounds of Formula 1.2:

a represents N, and b, c, and d represent carbon;

A and B each represent $H_2$ when the double bond between C-5 and C-6 is absent, and A and B each represent H when the double bond is present;

$R^5$, $R^6$, $R^7$, and $R^8$ each represent H;

$R^{32}$ and $R^{34}$ are each independently selected from H, halo (e.g., Cl or Br) benzotriazol-1yloxy or alkyl (most preferably $C_1$ to $C_4$ alkyl, more preferably methyl); most preferably $R^{32}$ and $R^{34}$ are each independently selected from H or halo; more preferably $R^{32}$ and $R^{34}$ are each independently selected from H, Cl or Br;

$R^{36}$ and to $R^{38}$ are each independently selected from H or halo (e.g, Cl or Br), most preferably $R^{36}$ is halo and $R^{38}$ is H, more preferably $R^{36}$ is Cl and $R^{38}$ is H, even more preferably $R^{36}$ is Cl at the C-8 position and $R^{38}$ is H;

W represents —$OR^{40}$; and $R^{40}$ represents heteroaryl (e.g., pyridyl, such as 3- or 4-pyridyl, and pyridyl N-oxide, such as 3- or 4-pyridyl N-oxide), alkyl (e.g., ethyl), or 3- or 4-N-substituted piperidyl (most preferably the substituent on said N-substituted piperidyl is $C_1$ to $C_4$ alkyl, and more preferably methyl).

Compounds of Formula 1.3 include compounds wherein (a) when Y represents —$OR^{52}$, and when both $R^{44}$ and $R^{46}$ are hydrogen, and when both $R^{48}$ and $R^{50}$ are H, then $R^{52}$ is not phenyl; and (b) when Y represents —$OR^{52}$, and when both $R^{44}$ and $R^{46}$ are hydrogen, and when $R^{48}$ is Cl at the C-8 position and $R^{50}$ is H, then $R^{52}$ is not ethyl.

Compounds of Formula 1.3 also include compounds wherein (a) when Y represents —$OR^{52}$, and when both $R^{44}$ and $R^{46}$ are hydrogen, and when both $R^{48}$ and $R^{50}$ are H, then $R^{52}$ is not aryl; and (b) when Y represents —$OR^{52}$, and when both $R^{44}$ and $R^{46}$ are hydrogen, and when $R^{48}$ is Cl at the C-8 position and $R^{50}$ is H, then $R^{52}$ is not alkyl.

Compounds of Formula 1.3 further include compounds wherein (a) when Y represents —$OR^{52}$, and when both $R^{44}$ and $R^{46}$ are hydrogen, and when both $R^{48}$ and $R^{50}$ are H, then $R^{52}$ is not aryl; and (b) when Y represents —$OR^{52}$, and when both $R^{44}$ and $R^{46}$ are hydrogen, and when $R^{48}$ is halo at the C-8 position and $R^{50}$ is H, then $R^{52}$ is not alkyl.

Compounds of Formula 1.3 still further include compounds wherein (a) when Y represents —$OR^{52}$, and when both $R^{44}$ and $R^{46}$ are hydrogen, and when both $R^{48}$ and $R^{50}$ are H, then $R^{52}$ is not aryl; and (b) when Y represents —$OR^{52}$, and when both $R^{44}$ and $R^{46}$ are hydrogen, and when $R^{48}$ is halo and $R^{50}$ is H, then $R^{52}$ is not alkyl.

Compounds of Formula 1.3 even further include compounds wherein when Y represents —$OR^{52}$, and when both $R^{44}$ and $R^{46}$ are hydrogen, and when both $R^{48}$ and $R^{50}$ are H, then $R^{52}$ is not aryl and $R^{52}$ is not alkyl.

Preferably for compounds of Formula 1.3:

a represents N, and b, c, and d represent carbon;

A and B each represent $H_2$ when the double bond between C-5 and C-6 is absent, and A and B each represent H when the double bond is present;

$R^5$, $R^6$, $R^7$, and $R^8$ each represent H;

$R^{44}$ and $R^{46}$ are each independently selected from H, halo (e.g., Cl or Br) benzotriazol-1yloxy or alkyl (most preferably $C_1$ to $C_4$ alkyl, more preferably methyl); most preferably $R^{44}$ and $R^{46}$ are each independently selected from H or halo; more preferably $R^{44}$ and $R^{46}$ are each independently selected from H, Cl or Br;

$R^{48}$ and to $R^{50}$ are each independently selected from H or halo (e.g, Cl or Br), most preferably $R^{48}$ is halo and $R^{50}$ is H, more preferably $R^{48}$ is Cl and $R^{50}$ is H, even more preferably $R^{48}$ is Cl at theC-8 position and $R^{50}$ is H;

$R^{52}$ represents heteroaryl (most preferably 3- or 4-pyridyl, or 3- or 4-pyridyl N-oxide), aryl (most preferably phenyl or substituted phenyl, e.g., halo substituted phenyl such as p-bromophenyl), or 3- or 4-N-substituted piperidyl (most preferably the substituent on said N-substitued piperidyl is $C_1$ to $C_4$ alkyl, and more preferaby methyl); and $R^{70}$ represents phenyl, 3-pyridyl, 4-pyridyl, 3-pyridyl N-oxide, 4-pyridyl N-oxide, 3- or 4-N-substituted piperidyl, wherein the substituent on said N-substituted piperidyl is $C_1$ to $C_4$ alkyl (most preferably methyl), alkylcarbonyl or —$C(O)NH(R^{10})$ wherein $R^{10}$ is H or alkyl, most preferably the substituent on the N-substituted piperidyl group is $C_1$ to $C_4$ alkyl.

Compounds of Formula 1.3 include:

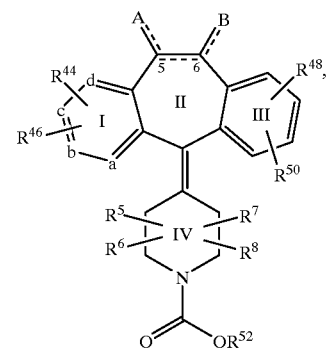

(1.3A)

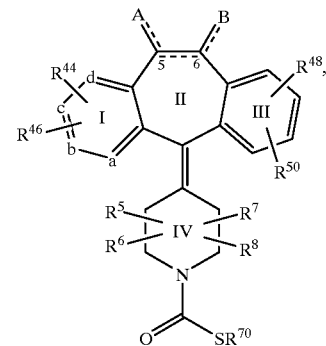

(1.3B)

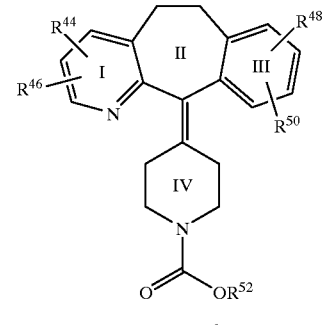

and

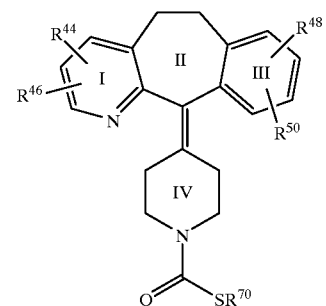

(1.3D)

wherein all substituents are as defined above

Compounds of Formula 1.0 include compounds Formula 1.4:

(1.4)

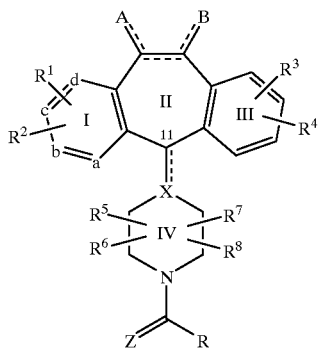

wherein all substituents are as defined for Formula 1.0. In particular, compounds of Formula 1.4 include compounds wherein R is —SR$^{65}$. Compounds of Formula 1.4 further include compounds wherein R is —SR$^{65}$ and R$^{10}$ is H, alkyl or aryl. Compounds wherein R is —SR$^{65}$ (and R$^{65}$ is alkyl) and R$^{10}$ is H, alkyl or aryl are disclosed in U.S. Pat. No. 4,826,853 and WO88/03138, and can be made inaccordance with procedures therein.

Compounds of Formula 1.0 also include compounds of Formula (1.5)

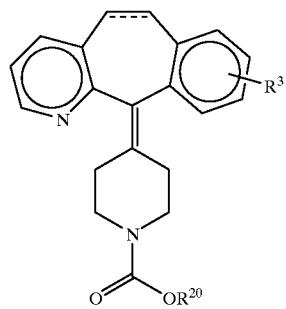

wherein all substituents are as defined in Formula 1.0. In particular, compounds of Formula 1.5 include compounds wherein R$^3$ is H or halo and R$^{20}$ is as defined for Formula 1.0 except that heteroaryl is excluded; these compounds are disclosed in U.S. Pat. No. 4,282,233 and can be made according to the process disclosed therein.

Also included in Formula 1.0 are compounds of Formula 1.6:

(1.6)

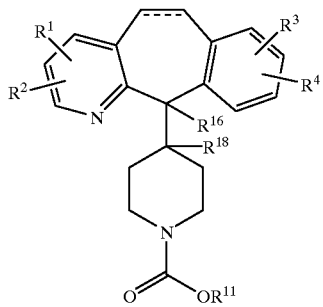

wherein the substituents are as defined for Formula 1.0. In particular, Formula 1.6 includes compounds wherein R$^1$ to R$^4$ are each independently selected from the substituents given for R$^1$ and R$^2$ of Formula 1.0, and R$^{16}$ and R$^{18}$ represent H and F respectively, or F and H respectively (preferably R$^{16}$ is F and R$^{18}$ is H); these compounds are disclosed in U.S. Pat. No. 4,863,931 and can be made in accordance with the procedures disclosed therein.

Lines drawn into the ring systems indicate that the indicated bond may be attached to any of the substitutable ring carbon atoms.

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine (Et$_3$N); diethyl ether (Et$_2$O).

Certain compounds of the invention may exist in different isomeric (e.g., enantiomers and diastereoisomers) forms. The invention contemplates all such isomers both in pure form and in admixture, including racemic mixtures. Enol forms are also included.

The compounds of the invention can exist in unsolvated as well as solvated forms, including hydrated forms, e.g., hemi-hydrate. In general, the solvated forms, with pharmaceutically acceptable solvents such as water, EtOH and the like are equivalent to the unsolvated forms for purposes of the invention.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds within the above described formulas include:
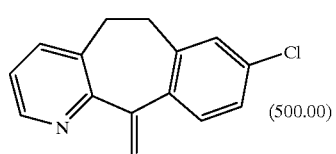
(500.00)
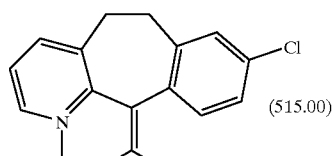
(515.00)
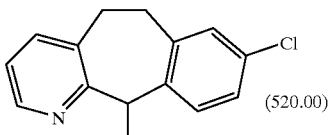
(520.00)
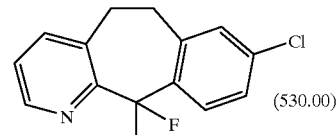
(530.00)
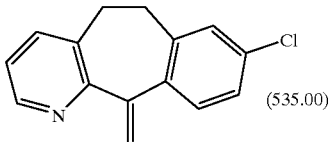
(535.00)
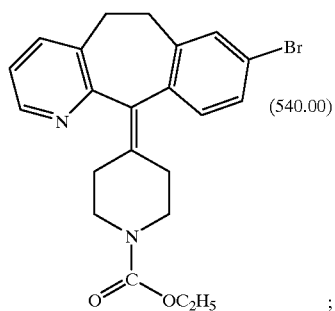
(540.00)
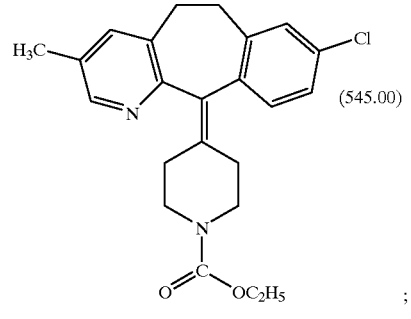
(545.00)
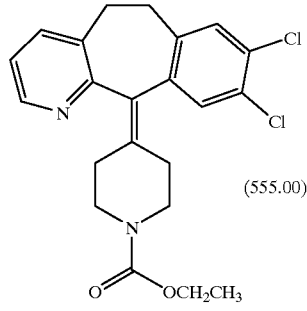
(555.00)
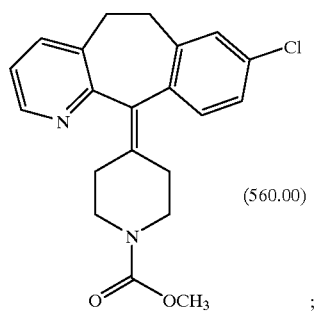
(560.00)
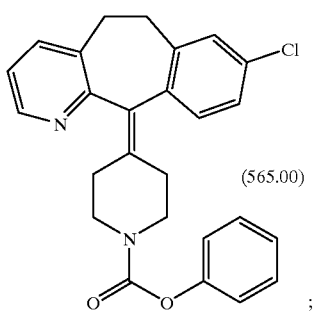
(565.00)

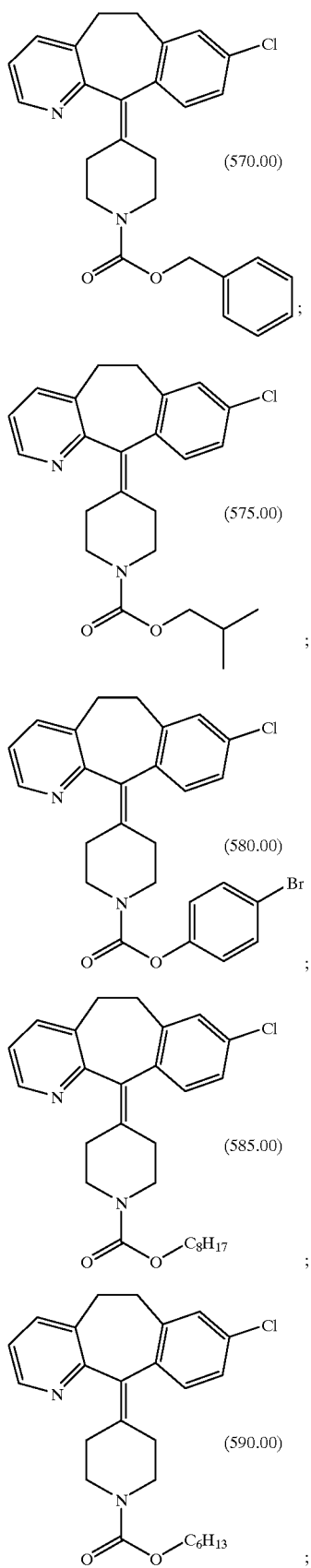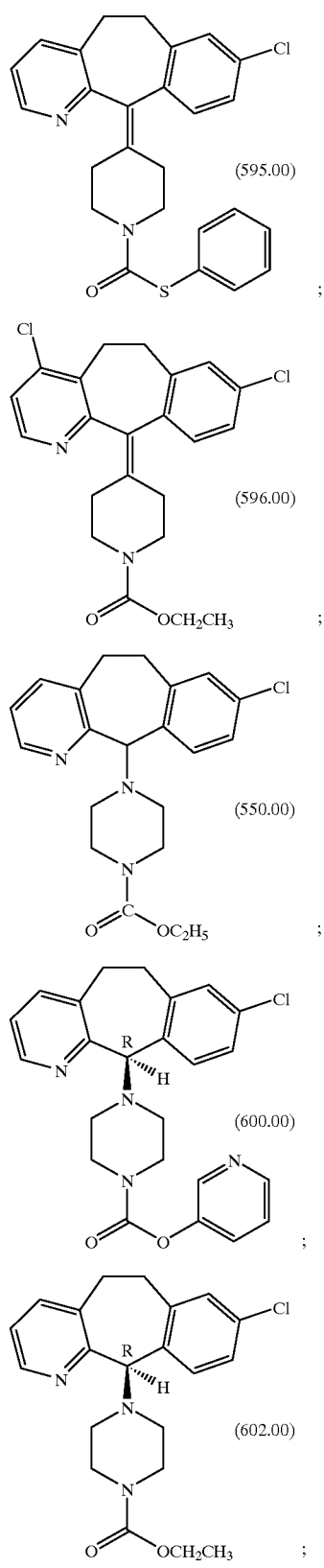

-continued
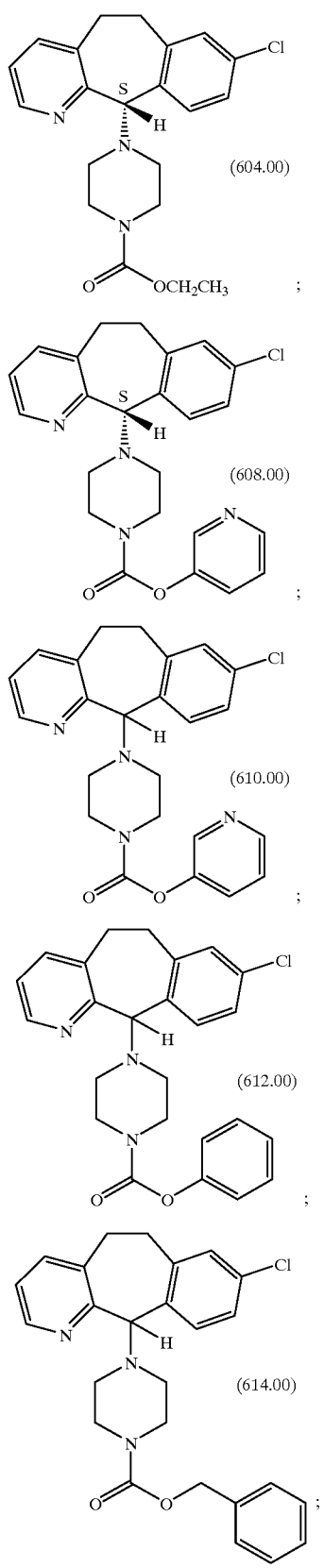
-continued
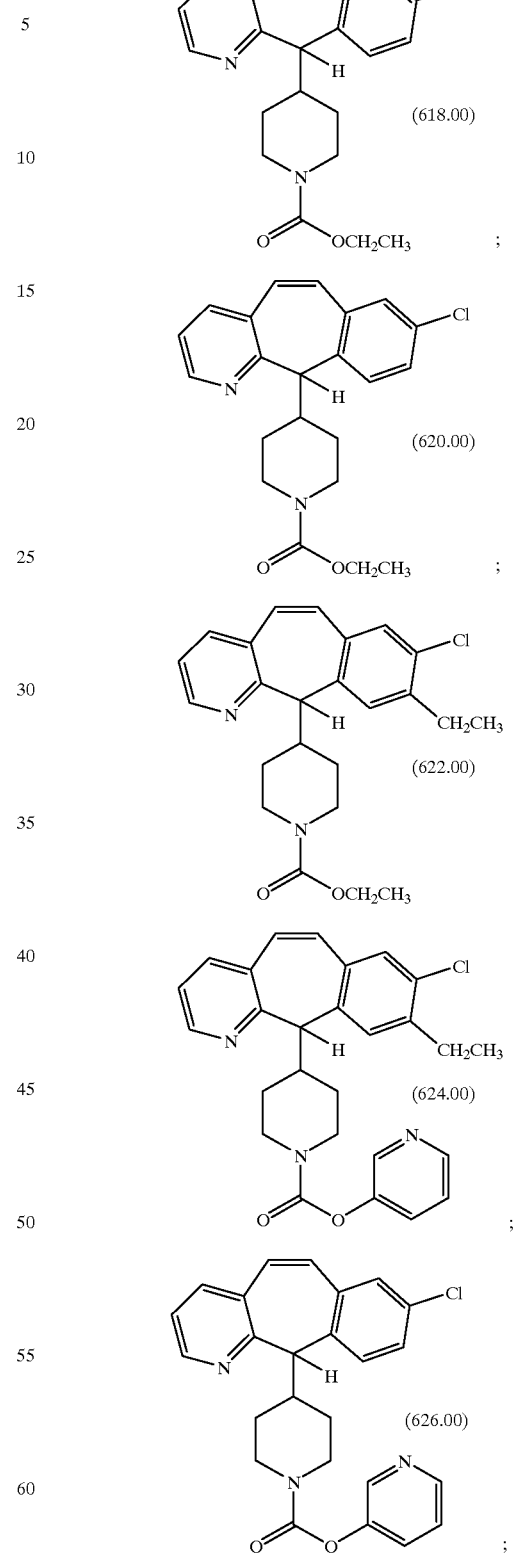

-continued
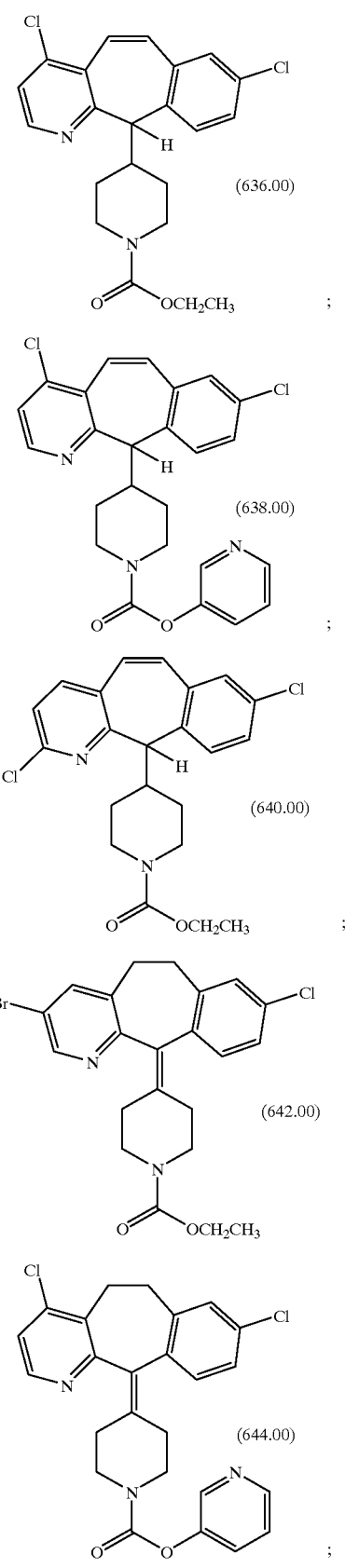
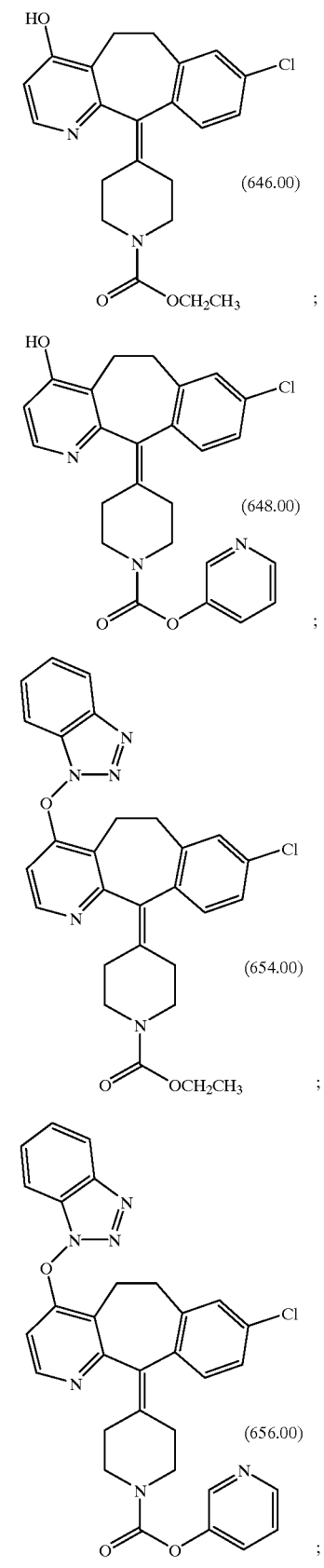

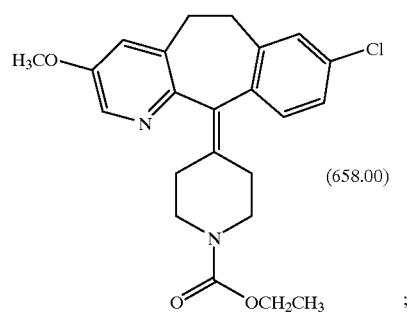
(658.00)
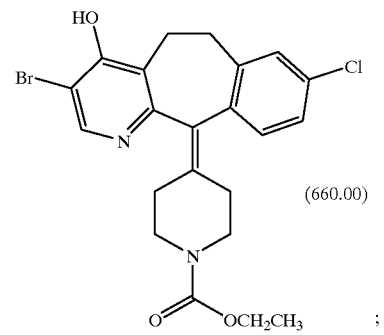
(660.00)
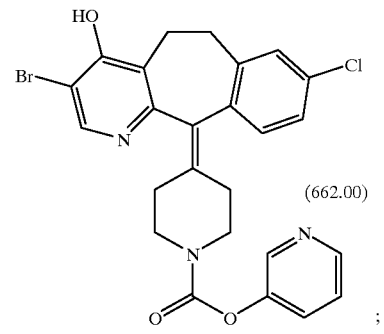
(662.00)
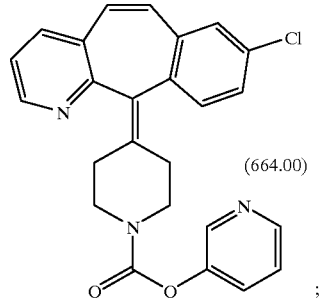
(664.00)
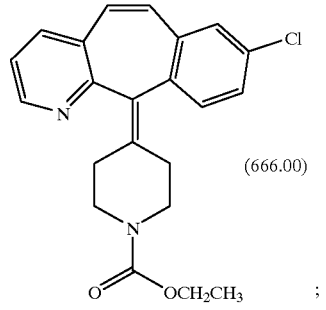
(666.00)
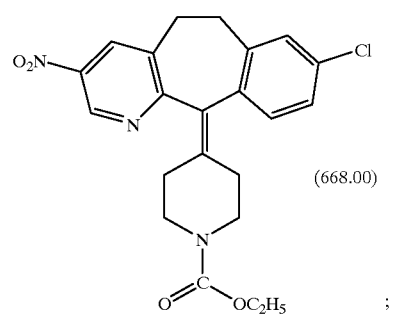
(668.00)
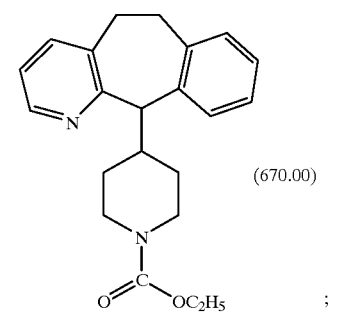
(670.00)
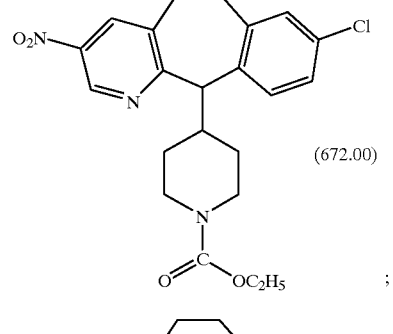
(672.00)
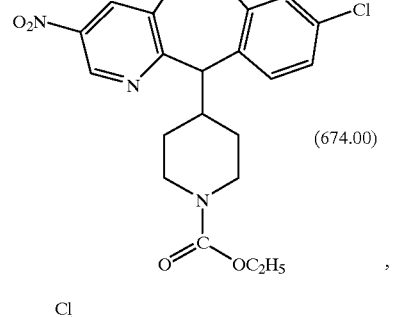
(674.00)
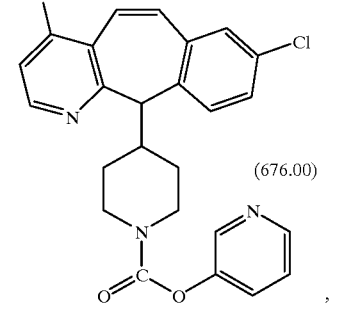
(676.00)

-continued

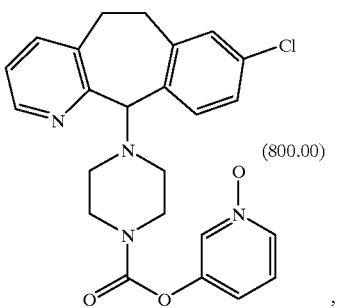
(800.00)

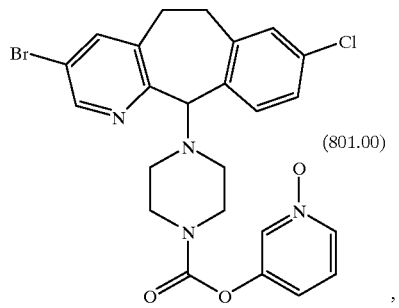
(801.00)

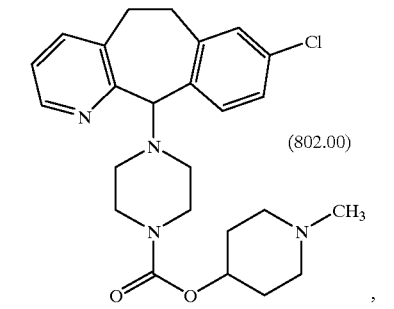
(802.00)

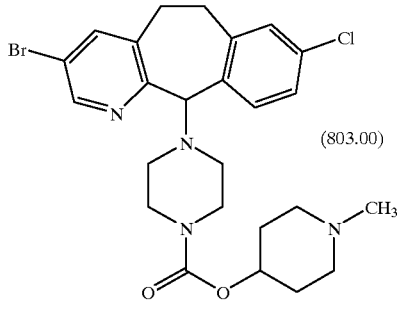
(803.00)

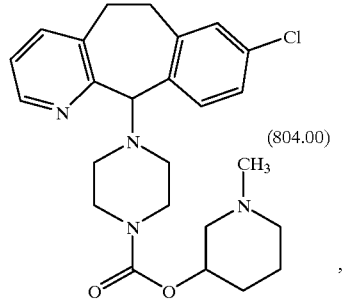
(804.00)

-continued

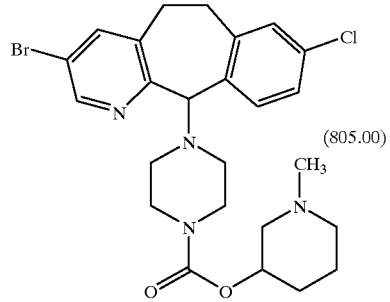
(805.00)

Preferred compounds useful in this invention are represented by Formulas 500.00, 530.00, 550.00, 565.00, 580.00, 595.00, 600.00, 604.00, 608.00, 610.00, 612.00, 618.00, 626.00, 642.00, 644.00, 656.00, 662.00, 676.00, 800.00, 801.00, 802.00, 803.00, 804.00 and 805.00, and the compounds of Examples 32 and 33.

More preferred compounds useful in this invention are represented by Formulas 500.00, 530.00, 565.00, 580.00, 595.00, 600.00, 608.00, 610.00, 612.00, 618.00, 626.00, 642.00, 644.00, 656.00, 662.00, 801.00, 802.00, 803.00, 804.00 and 805.00, and the compounds of Examples 32 ansd 33.

The following processes may be employed to produce compounds of Formula 400.00:

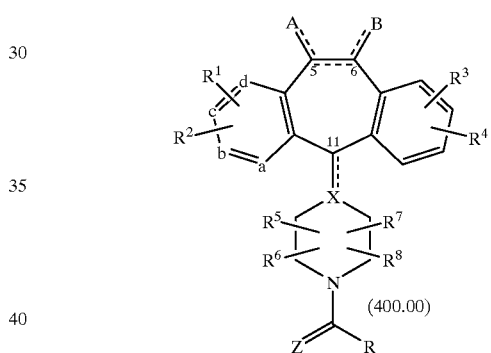

Those skilled in the art will appreciate that compounds of Formula 1.0, e.g., Formula 1.4, are represented by compounds of Formula 400.00. Those skilled in the art will also appreciate that the processes described below for producing compounds of Formula 400.00 (Formula 1.4) are also applicable to the compounds of Formulas 1.1, 1.2 and 1.3.

A compound of Formula 405.00 may be reacted with RC(O)L, wherein R is as defined for Formula 1.0, in the presence of a base to produce compounds of Formula 400.00.

Representative examples of appropriate bases are pyridine and triethylamine. L designates a suitable leaving group (e.g., Cl or Br).

Compounds of Formula 405.00 may be prepared by cleaving the group COOR$^a$ from the corresponding carbamates 415.00, for example, via acid hydrolysis (e.g., HCl) or base hydrolysis (e.g., KOH):

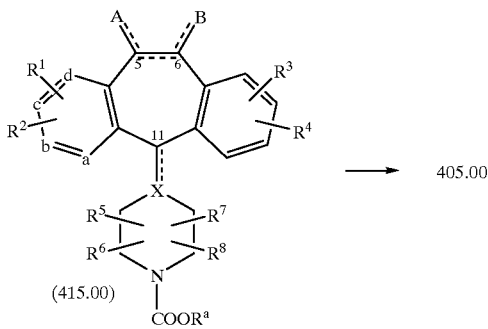 → 405.00 wherein R$^a$ is a group which does not prevent the cleavage reaction, e.g., R$^a$ is an optionally substituted alkyl such as ethyl.

Alternatively, depending upon the nature of R$^a$, as determined by one skilled in the art, Compound 415.00 may be treated with an organometallic reagent (e.g., CH$_3$Li), a reductive reagent (e.g., Zn in acid), etc., to form compounds of Formula 405.00.

Compound 415.00 may be prepared from the N-alkyl compound shown as Formula 420.00 below, in the manner disclosed in U.S. Pat. Nos. 4,282,233 and 4,335,036.

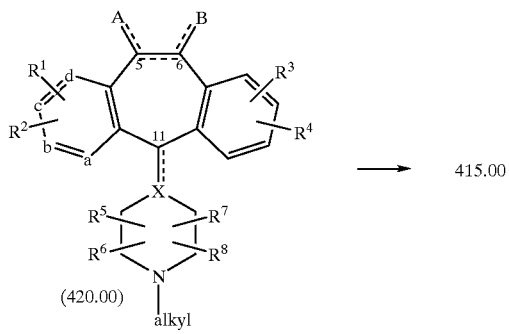 → 415.00

It also will be apparent to one skilled in the art that there are other methods for converting Compound 420.00 to Compound 405.00. For example, treatment of Compound 420.00 with BrCN via von Braun reaction conditions would provide nitrile 420.00a. Subsequent hydrolysis of the nitrile under either aqueous basic or acidic conditions would produce Compound 405.00. This method is preferable when there is substitution on the piperidine or piperazine ring.

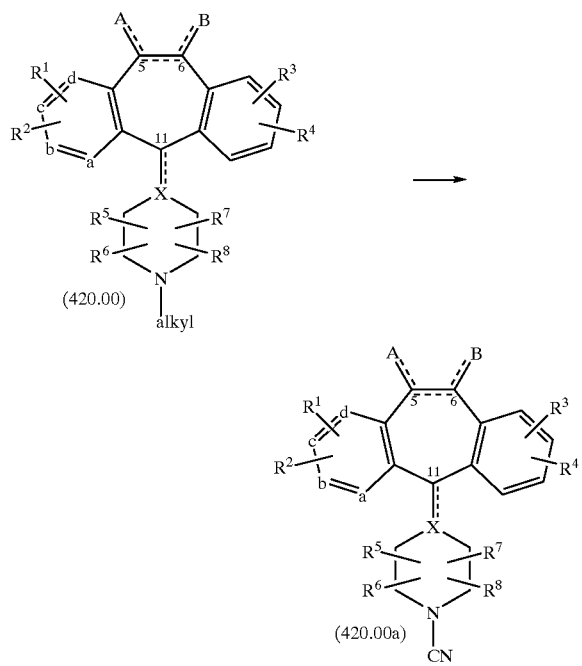

C. The compounds of Formula 400.00 wherein Z is O may be made by an alternative process using direct conversion of the N-alkyl compound 420.00 with an appropriate compound of Formula 410.00 such as a chloroformate (such as phenylchloroformate). An appropriate base, may be added, and heating may be required. Typically, a temperature ranging from 50–150° C. is utilized. Other compounds of the invention can be made by reacting a compound of Formula 400.00, wherein R is phenoxy, with the sodium salt of the appropriate alcohol.

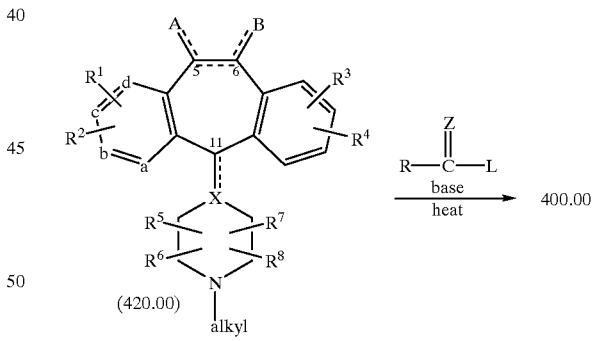

Compound 420.00 is prepared as described in part B above.

PREPARATION OF SINGLE BOND COMPOUNDS

Compounds of Formula 400.00, wherein X is carbon and the bond to carbon 11 (C-11) is a single bond, can be prepared by reducing compounds of Formula 405.00, wherein X is carbon and the bond to C-11 is a double bond, with lithium aluminum hydride in THF. Conversion to final products can be done following the process described above for conversion of compounds of Formula 405.00 to compounds of Formula 400.00.

PREPARATION OF DOUBLE BOND COMPOUNDS

Compounds of Formula 400.00, wherein X is a carbon atom having an exocyclic double bond to carbon 11, may be prepared from compound 420.00 as described above. Compounds of Formula 420.00 may be produced by the methods disclosed generally in U.S. Pat. No. 3,326,924 or alternatively may be prepared by a ring closure reaction, wherein the desired cycloheptene ring is formed by treating compound 425.00 with a super acid. Suitable super acids for this purpose include, for example, $HF/BF_3$, $CF_3SO_3H$ (triflic acid), $CH_3SO_3H/BF_3$, etc. The reaction can be performed in the absence of, or with, an inert co-solvent such as $CH_2Cl_2$. The temperature and time of the reaction vary with the acid employed. For example, with $HF/BF_3$ as the super acid system the temperature may be controlled so as to minimize side reactions, such as HF addition to the exocyclic double bond. For this purpose, the temperature is generally in the range of from about +5° C. to -50° C. With $CF_3SO_3H$ as the super acid system, the reaction may be run at elevated temperatures, e.g., from about 25° C. to about 150° C. and at lower temperatures but the reaction then takes longer to complete.

Generally the super acid is employed in excess, preferably in amounts of from about 1.5 to about 30 equivalents.

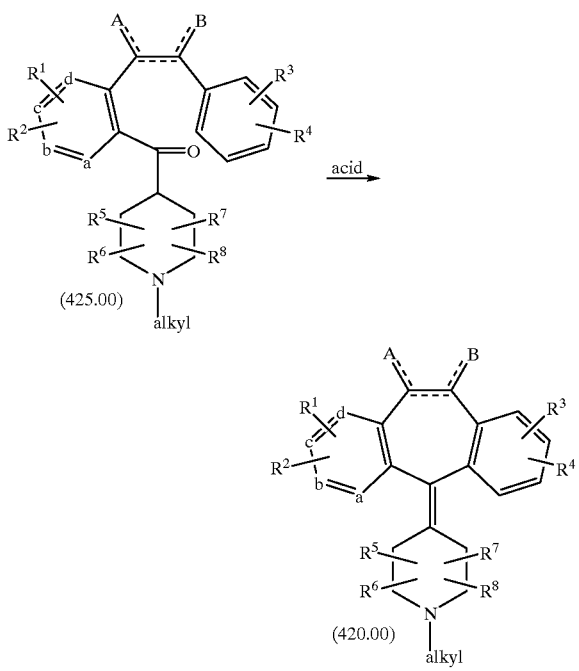

A ketone compound of Formula 425.00 may be formed by hydrolysis of 430.00, e.g., such as by reacting a Grignard intermediate of Formula 430.00 with an aqueous acid (e.g., aqueous HCl). $I^a$ in Formula 430.00 represents chloro, bromo or iodo.

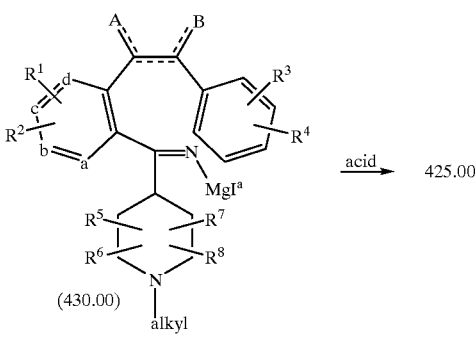

The Grignard intermediate 430.00 is formed by the reaction of the cyano compound 435.00 with an appropriate Grignard reagent 440.00 prepared from 1-alkyl-4halopiperidine. The reaction is generally performed in an inert solvent, such as ether, toluene, or THF, under general Grignard conditions e.g., temperature of from about 0° C. to about 75° C. Alternatively, other organometallic derivatives of the 1alkyl-4-halo piperidine can be employed.

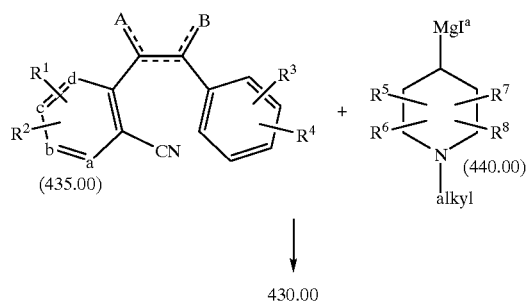

The cyano compound of Formula 435.00 is produced by converting the tertiary butyl amide of Formula 445.00 with a suitable dehydrating agent, such as $POCl_3$, $SOCl_2$, $P_2O_5$, toluene sulfonyl chloride in pyridine, oxalyl chloride in pyridine, etc. This reaction can be performed in the absence of or with a co-solvent, such as xylene.

The dehydrating agent such as $POCl_3$ is employed in equivalent amounts or greater and preferably in amounts of from about 2 to about 15 equivalents. Any suitable temperature and time can be employed for performing the reaction, but generally heat is added to accelerate the reaction. Preferably the reaction is performed at or near reflux.

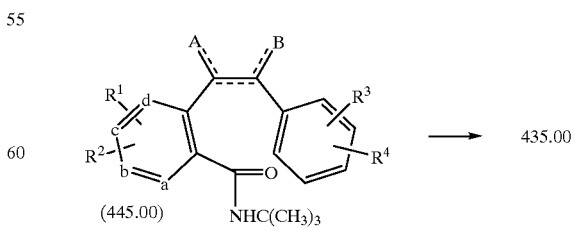

The tert-butylamide of Formula 445.00 may be produced by reaction of a compound of Formula 450.00a and 450.00b, in the presence of base, wherein G is chloro, bromo or iodo.

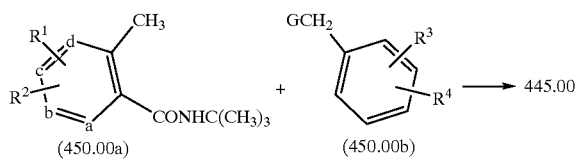

(450.00a) + (450.00b) → 445.00

The compound of Formula 450.00a may be formed by hydrolysis of the corresponding nitrile wherein the appropriate cyanomethyl pyridine, such as 2-cyano-3-pyridine, is reacted with a tertiary butyl compound in acid, such as concentrated $H_2SO_4$ or concentrated $H_2SO_4$ in glacial acetic acid. Suitable tertiary butyl compounds include, but are not limited to, t-butyl alcohol, t-butyl chloride, t-butyl bromide, t-butyl iodide, isobutylene or any other compound which under hydrolytic conditions forms t-butyl carboxamides with cyano compounds. The temperature of the reaction will vary depending upon the reactants, but generally the reaction is conducted in the range of from about 50° C. to about 100° C. with t-butyl alcohol. The reaction may be performed with inert solvents, but is usually run neat.

An alternative process for the formation of compounds of Formula 400.00a may involve direct cyclization of Compound 455.00 as shown below.

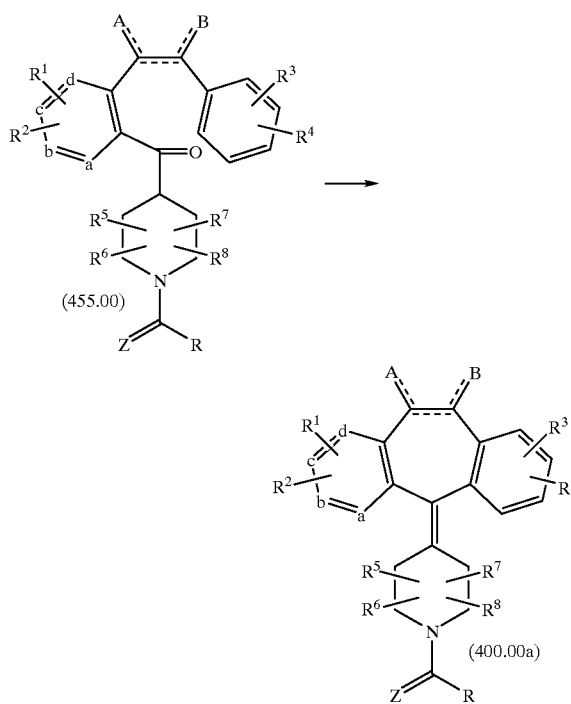

Cyclization to form the cycloheptene ring may be accomplished with a strong acid (e.g., triflic, polyphosphoric, $HF/BF_3$), and may be performed in an inert solvent, such as ether, toluene or THF. The temperature and time may vary with the acid employed, as described in process A above.

Compounds of Formula 455.00 wherein Z=O may be prepared by treating a compound of Formula 425.00 with an appropriate chloroformate (e.g. ethyl chloroformate) of formula 410.00 in the appropriate solvent, such as toluene, dioxane or xylene, and at a temperature ranging from 50–150° C., preferably 100–120° C.

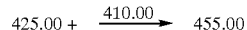

425.00 + 410.00 → 455.00

A second method of preparing compounds of Formula 455.00 involves reacting an unsubstituted piperidylidene compound of Formula 460.00 with the appropriate chloroformate (e.g., ethyl chloroformate) of Formula 410.00 in the presence of base, such as pyridine or $Et_3N$.

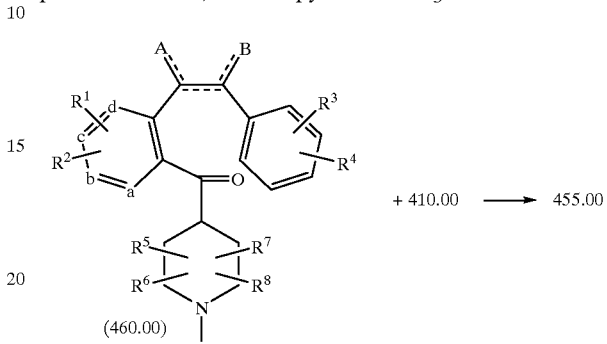

+ 410.00 → 455.00

Compounds of Formula 460.00 may be produced from the corresponding carbamates of Formula 465.00, via acid hydrolysis, using for example, aqueous HCl, or base hydrolysis using for example, KOH. Alternatively, some compounds can be prepared by treating the carbamate, Formula 465.00, with an organometallic reagent, such as methyl lithium or a reductive reagent, such as Zn in acid, etc., depending upon the nature of the $R^a$ group. For example, if $R^a$ is a simple alkyl group, $CO_2R^a$ may be cleaved by alkaline hydrolysis at 100° C.

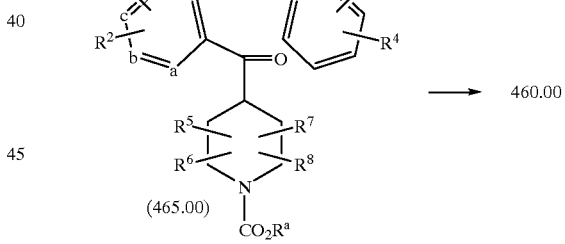

→ 460.00

The carbamate compounds of Formula 465.00 may be prepared from the appropriate alkyl compound of Formula 425.00 by treatment with a chloroformate, preferably in an inert solvent, such as toluene, with warming to approximately 80° C. Other alternative methods are available for the conversion of 425.00 to 455.00 as previously described (e.g. Von Braun reaction conditions). Compounds of Formula 425.00 may be prepared as described above.

SUBSTITUTION ON THE PYRIDINE RING

Various methods can be used as described in WO 88/03138 to provide compounds which are substituted on the pyridine ring, i.e., in positions 2-, 3- and or 4-positions of the tricyclic ring system. For example, the cyclization methods described on pages 20–30 of WO 88/03138 can already have the appropriate substituents on the pyridine ring in place. A variety of substituted pyridines are known in the literature and can be employed in these syntheses. Alternatively, the azaketone of Formula XIX (from page 27 of WO 88/03138)

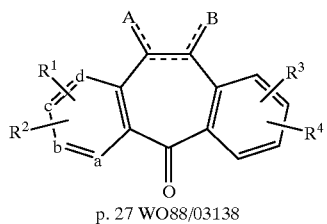

p. 27 WO88/03138 wherein $R^1$ and $R^2$ are both H can be converted to the appropriately substituted azaketone wherein $R^1$ and $R^2$ are non-H substitutents. If both $R^1$ and $R^2$ are desired to be non-H substitutents the procedure would be repeated.

The azaketone is thus reacted with an oxidizing agent such as MCPBA or $H_2O_2$ to produce the corresponding compound in which the nitrogen of the pyridine ring is an N-oxide:

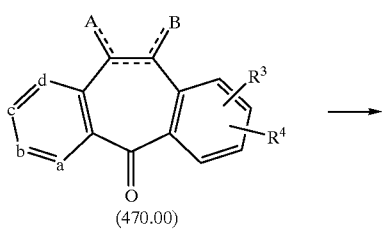

(470.00)

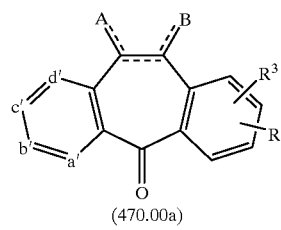

(470.00a)

wherein one of a', b', c' or d' is N→O and the others are CH or $CR^1$ or $CR^2$. This reaction is normally run at temperatures from −15° C. to reflux, more typically at about 0° C. The reaction is preferably conducted in an inert solvent such as $CH_2Cl_2$ for MCPBA or acetic acid for hydrogen peroxide.

The azaketone N-oxide of Formula 470.00a can then be reacted with a chlorinating agent such as $SO_2Cl_2$ or $SOCl_2$ to form a compound of Formula 470.00b. Typically, this reaction results in monosubstitution of Cl in the ortho or para-position relative to the N atom of the ring.

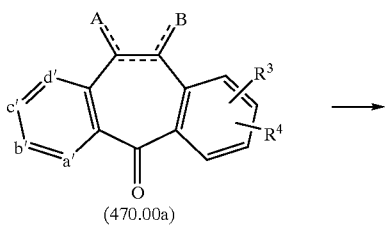

(470.00a)

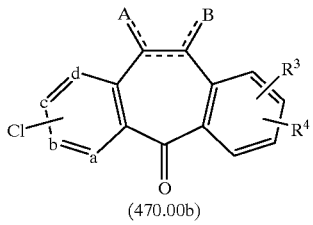

(470.00b)

To provide the disubstituted products, steps 1 and 2 above are repeated

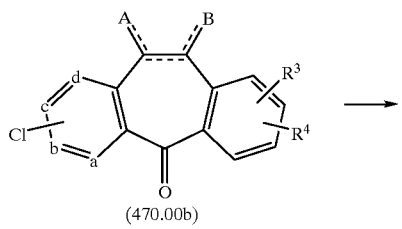

(470.00b)

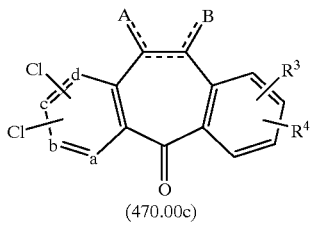

(470.00c)

Typically, the resulting disubstituted compounds have Cl ortho and para relative to the N atom of the pyridine ring.

The mono or disubstituted compounds of Formulas 470.00b and 470.00c above can be reacted with various nucleophiles such as alkoxides, amines, thiols, etc. This will result in compounds where one or both of the Cl substituents are replaced by the nucleophile to provide a compound of Formula 470.00d or a compound easily converted to Formula 470.00d.

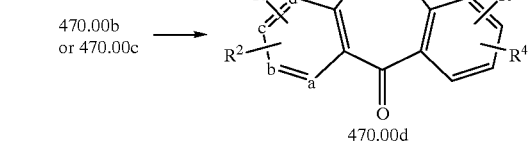

470.00d

The substituted ketone of Formula 470.00 can then be converted to the desired compound by the methods described above.

Formula 405.00, wherein $R^1$ or $R^2$ are chlorine, can be made by the following alternate process.

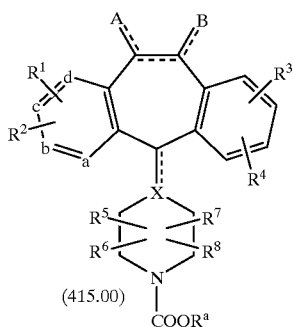

(415.00)

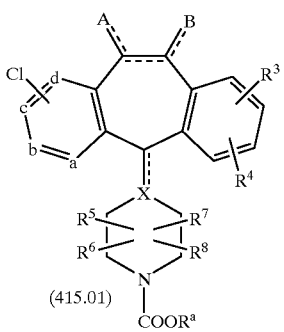

(415.01)

The N-oxide of Formula 415.00 can be treated with $POCl_3$ to form a 10 compound of Formula 415.01. Typically, this reaction results in mono-substitution of Cl in the ortho or para position relative to the N atom of the ring. The N-oxide of Formula 415.00 can be formed by oxidizing Formula 415.00 with a peroxyacid such as 4-chloroperoxybenzoic acid.

Alternatively, the Cl substituted azaketones of formula 470.00b or 470.00c above can be converted to the corresponding derivatives of Formula 405.00 above wherein $R^1$ and/or $R^2$ is Cl by methods analogous to those described above. At this point the Cl substituent(s) can be displaced by an appropriate nucleophile to provide the desired substituent. Suitable nucleophiles include alkoxide, amines, thiols, etc. This reaction usually requires higher tempertures (e.g., from about 100° to about 200° C.) than the displacement reaction to produce ketone 470.00d above. It is also usually conducted in a sealed vessel in an inert solvent. The compound of Formula 405.00 is then converted to a compound of Formula 400.00 as described above.

PREPARATION OF C5–C6-ENE DERIVATIVES

Compounds of formula 400.00 with a double bond between C-5 and C-6 can be prepared by heating a compound of Formula 470.00h in acetic acid with $SeO_2$ to produce a compound of Formula 470.00i. Compounds of Formula 470.00i can be converted to final products according to methods already described.

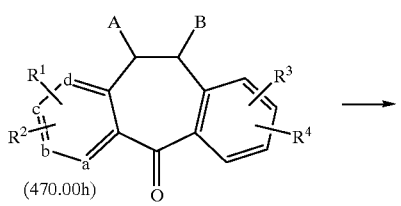

(470.00h)

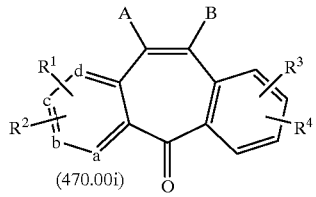

(470.00i)

PREPARATION OF PIPERAZINE ANALOGS

Compounds having a piperazine ring bound to the C-11 of the tricyclic nucleus, i.e., Formula 1.0 wherein X is N, are best prepared via alkylation of the appropriately substituted piperazine compound of Formula 700.00 with a compound of Formula 705.00. Compounds of Formula 705.00 contain the appropriately substituted halide (such as Cl, Br, or I) or other similar leaving group (e.g., tosyloxy or mesyloxy). The reaction is usually conducted in an inert solvent, such as THF or toluene, optionally with a base such as $Et_3N$ or $K_2CO_3$, and typically at a temperature range of ambient to reflux to produce a compound of Formula 710.00.

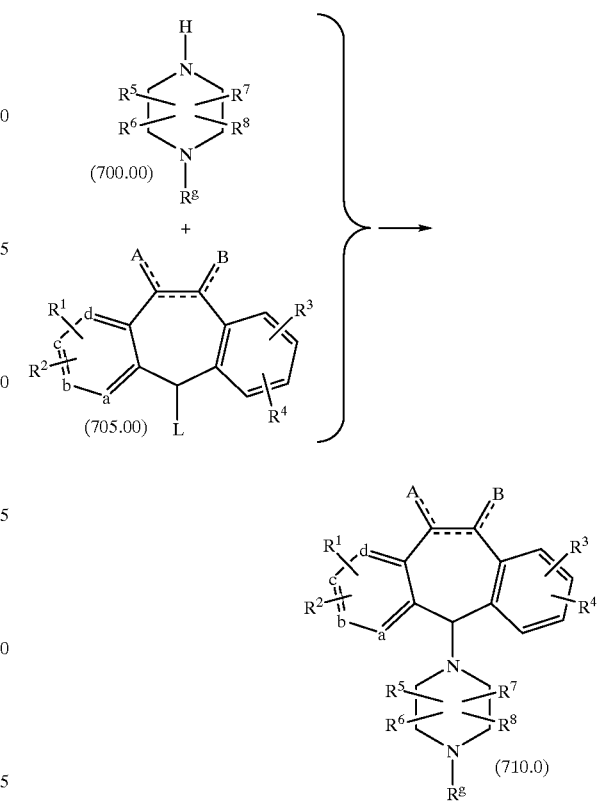

In this reaction $R^g$ is H or $CO_2R^a$ (wherein $R^a$ is a $C_1$ to $C_4$ alkyl group). The preparation of compound 705.00 wherein L is Cl is analogous to the procedure described in U.S. Pat. No. 3,409,621. By methods known in the art compounds of Formula 710.00, wherein $R^g$ is $CO_2R^a$, can be converted to Formula 710.00 wherein $R^g$ is H, by acid or base hydrolysis as described in U.S. Pat. No. 4,826,853. Compounds of formula 710.00, wherein $R^g$ is H, can be converted to compounds of Formula 400.00 by the process used to convert Formula 405.00 to Formula 400.00. Compounds of 410.00, wherein R is 3-pyridyloxy, can be prepared by reacting 3-hydroxy-pyridine with an excess of phosgene in toluene/CH$_2$Cl$_2$ at 0° C. in the presence of a base such as pyridine.

An alternate route for generating the compound of Formula 710.00 is by reductive amination of the aza ketone 715.00 with the piperazine 700.00

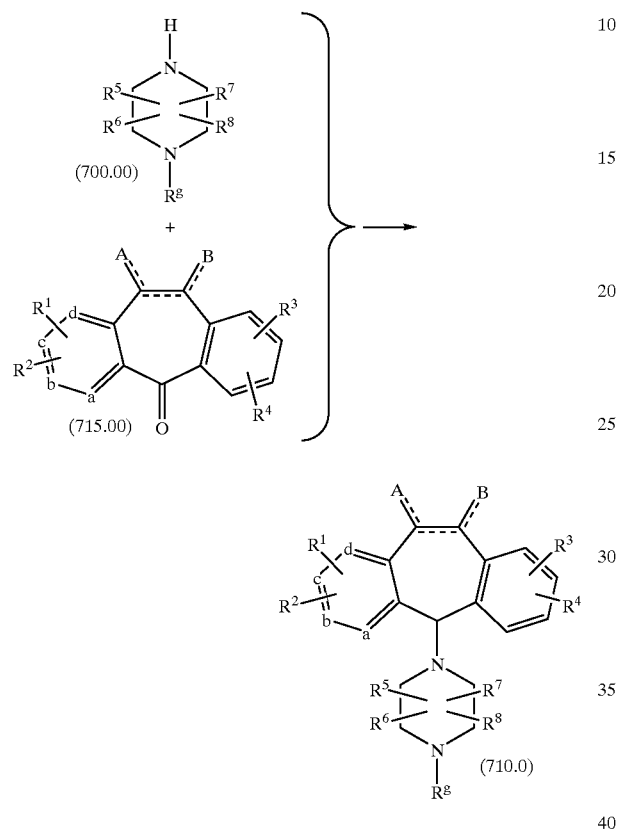

The reaction is typically carried out in a polar solvent, such as MeOH or EtOH, optionally in the presence of a dehydrating agent, such as 3Å molecular sieves. The intermediate Schiff base can be reduced to the compound of Formula 710.00 by employing a variety of reducing agents, such as NaCNBH$_3$, or catalytic hydrogenation, for example, hydrogen over Pd/C.

When R$^g$ is C(Z)R, these are the compounds of the invention.

An alternative process for introducing substituents at the C-3 position of pyridine Ring I of Formula 1.0, involves nitrating a compound of Formula 415.00 (except wherein X is nitrogen) or a compound of Formula 470.00d with tetrbutylammonium nitrate—TFAA in CH$_2$Cl$_2$ at a temperature of 0° C. to room temperature (about 25° C.). The nitro group may then be reduced to the corresponding amine using iron filings in ethanol, or powdered Zn-HOAc in aqueous THF. By methods known to those skilled in the art, the amine group can be converted to a variety of substituents, such as, halo, cyano, thio, hydroxyl, alkyl, alkenyl, alkynyl and haloalkyl.

Compounds of Formulas 1.2 and 1.3, wherein R$^{30}$, R$^{40}$, R$^{52}$ and R$^{70}$ represent a pyridyl N-oxide, can be produced by reacting compounds of Formulas 1.2, and 1.3, wherein R$^{30}$, R$^{40}$, R$^{52}$ and R$^{70}$ represent pyridyl, with one molar equivalent of an oxidizing agent (such as oxone).

Compounds of Formula 1.1, wherein R$^{30}$ or R$^{70}$ represent a pyridyl N-oxide, can be produced by reacting a compound of the formula (XI)

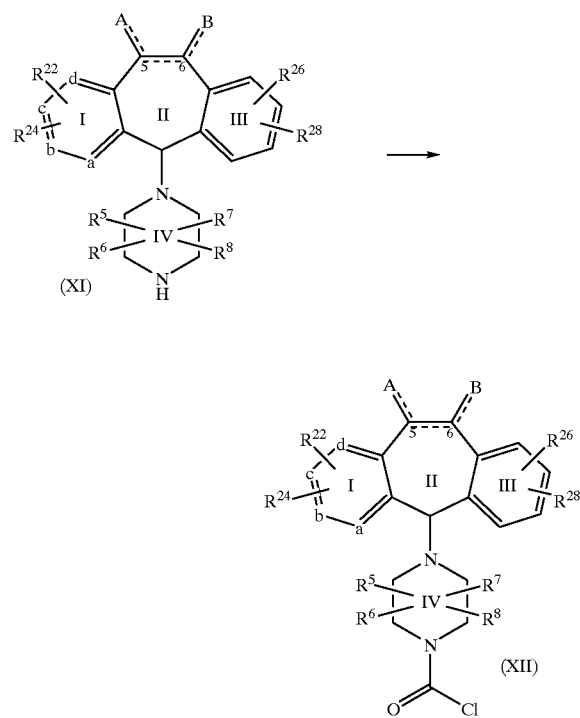

OR

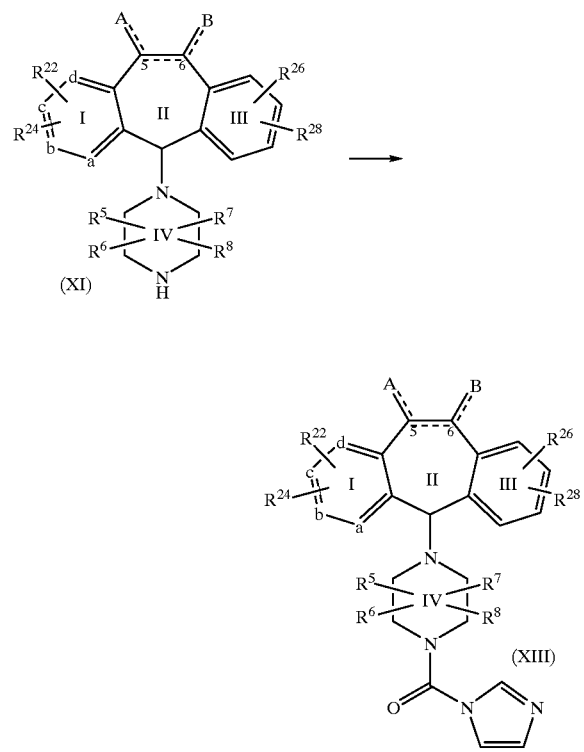

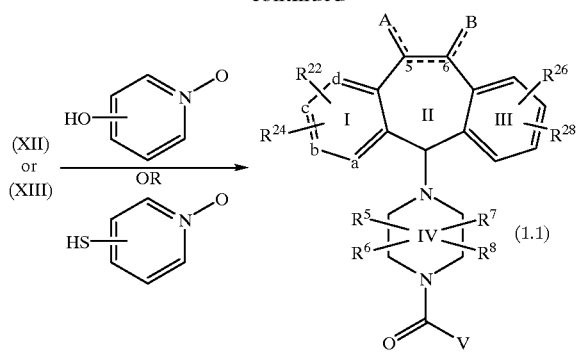

with phosgene in the presence of a suitable base, such as pyridine, to form a compound of the formula (XII), which is then reacted with the approriate hydroxypyridine N-oxide or mercaptopyridine N-oxide.

Alternatively, compounds of Formula 1.1, wherein $R^{30}$ or $R^{70}$ represent a pyridyl N-oxide, can be produced by reacting a compound of the formula (XI) with carbonyldiimidazole to form a compound of the formula (XIII) which is reacted with the approriate hydroxypyridine N-oxide (or mercaptopyridine N-oxide) in the presence of either $ZnBr_2$ or NaH.

Various electrophilic species can also be added to the pyridine ring from the corresponding halo-substituted pyridine (Formula 405.00 wherein $R^1$ is halo, preferably bromo or iodo). Transmetallation of the halo derivative using an alkyl lithium (e.g. n-BuLi) provides the lithio derivative, which can then be quenched with the appropriate electrophile (e.g. $R^1L$, etc.).

Also, the halogens can be displaced with nucleophiles, such as HOBT, to give compounds with substituents in the pyridine ring.

In the above processes, it is sometimes desirable and/or necessary to protect certain $R^1$, $R^2$, $R^3$ and $R^4$ etc., groups during the reactions. Conventional protecting groups are operable as described in Greene, T. W., "Protective Groups In Organic Synthesis," John Wiley & Sons, New York, 1981. For example, the groups listed in column 1 of Table 1 may be protected as indicated in column 2 of the table:

TABLE 1

| PROTECTED GROUPS | |
|---|---|
| 1. GROUP TO BE PROTECTED | 2. PROTECTED GROUP |
| —COOH | —COOalkyl, —COObenzyl, —COOphenyl,  |
| >NH | >NCOalkyl, >NCObenzyl |

TABLE 1-continued

| PROTECTED GROUPS | |
|---|---|
| 1. GROUP TO BE PROTECTED | 2. PROTECTED GROUP |
| | >NCOphenyl |
| —OH | 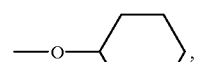, —OCH₂phenyl₂, —OCH₃, OSi(CH₃)₂(t-Bu), |
| —NHR, wherein R is any substituent on an amino group within the scope of the claims | 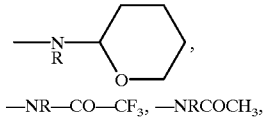, —NR—CO—CF₃, —NRCOCH₃, —NRCH₂-phenyl |
| —NH₂ | 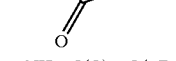, —NH—C(O)—O(t-Bu) |

Other protecting groups well known in the art also may be used. After the reaction or reactions, the protecting groups may be removed by standard procedures.

Compounds useful in this invention are exemplified by the following preparative examples, which should not be construed to limit the scope of the disclosure. Alternative mechanistic pathways and analogous structures within the scope of the invention may be apparent to those skilled in the art.

PREPARATIVE EXAMPLE 1

A. N-(1,1-DIMETHYLETHYL)-3-METHYL-2-PYRIDINE CARBOXAMIDE

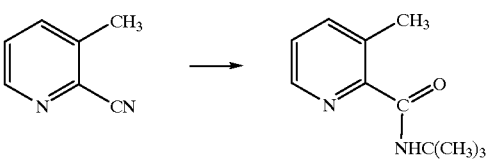

Suspend 2-cyano-3-methyl pyridine (400 g) in t-butanol (800 mL) and heat to 70° C. Add concentrated $H_2SO_4$ (400 mL) dropwise over 45 minutes. Maintain the temperature at 75° C., until the reaction is complete, and for an additional 30 minutes. Dilute the mixture with water (400 mL), charge with toluene (600 mL) and bring to pH 10 with concentrated aqueous ammonia. Maintain the temperature at 50–55° C. during the work up. Separate the toluene phase, and extract the aqueous layer.

Combine toluene phases and wash with water. Remove the toluene to yield the title compound N-(1,1-dimethylethyl)-3-methyl-2-pyridine carboxamide, as an oil, from which solid product is crystallized. (Yield 97%, as determined by an internal standard assay with gas chromatography).

B. 3-[2-(3-CHLOROPHENYL)ETHYL]-N-(1,1-DIMETHYLETHYL)-2-PYRIDINE CARBOXAMIDE

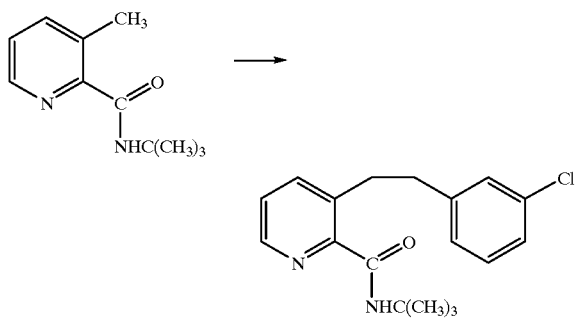

Dissolve the title compound of Preparative Example 1A, N-(1,1-dimethylethyl)-3-methyl-2-pyridine carboxamide (31.5 g.) in THF (600 mL) and cool the resulting solution to −40° C. Add n-butyllithium (2 eq.) in hexane while maintaining the temperature at −40° C. The solution turns deep purple-red. Add NaBr (1.6 g) and stir the mixture. Add solution of m-chlorobenzylchloride (26.5 g., 0.174 mole) in THF (125 mL) while maintaining the temperature at −40° C. Stir the reaction mixture until the reaction is complete as determined by thin layer chromatography. Add water to the reaction until the color is dissipated. Extract the reaction mixture with EtOAc, wash with water, and concentrate to a residue which is the title compound. (Yield 92% as shown by chromatography).

C. 3-[2-(3-CHLOROPHENYL)ETHYL]-2-PYRIDINE-CARBONITRILE

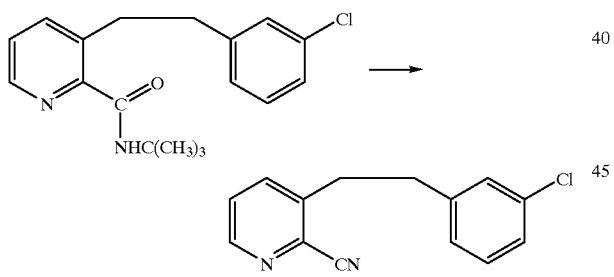

Heat a solution of the title compound of Preparative Example 1B, 3-[2-(3-chlorophenyl)ethyl]-N-(1,1-dimethylethyl)-2-pyridine carboxamide (175 g, 0.554 mole) in phosphorous oxychloride (525 mL, 863 g, 5.63 mole) and reflux for 3 hours. Determine completion of the reaction by thin layer chromatography. Remove any excess phosphorous oxychloride by distillation at reduced pressure and quench the reaction in a mixture of water and isopropanol. Bring to pH 5–7 by adding 50% aqueous NaOH solution while maintaining the temperature below 30° C. Filter the crystalline slurry of crude product and wash with water. Purify the crude product by slurrying the wet cake in hot isopropanol, and cool to 0–5° C. Filter the product, wash with hexane and dry at a temperature below 50° C. to yield the title compound. (Yield: 118 g (HPLC purity 95.7%), m.p. 72° C.–73° C., 89.4% of theory).

D. 1-(METHYL-4-PIPERIDINYL)[3-(2-(3-CHLOROPHENYL)ETHYL)-2-PYRIDINYL] METHANONE HYDROCHLORIDE

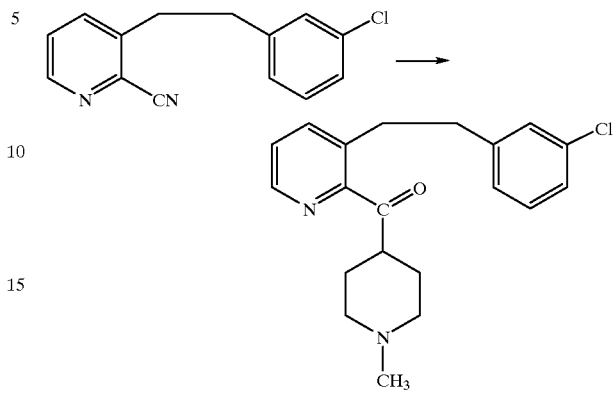

Dissolve the title compound of Preparative Example 1C, (118 g, 0.487 mole) in dry THF (1.2 L) and add N-methyl-piperidyl magnesium chloride (395 mL, 2.48 mole/liter, 0.585 mole, 1.2 eq.) over 15 minutes. Maintain the temperature at 40° C.–50° C. by cooling with water as necessary, for 30 minutes. Determine completion of the reaction by thin layer chromatography. Quench the reaction by reducing the pH to below 2 with 2N HCl and stir the resulting solution at 25° C. for 1 hour. Remove the bulk of the THF by distillation and adjust the resulting solution to pH 3.5 by addition of aqueous NaOH. Cool to 0 to 5° C. and filter off the crystalline hydrochloride salt product. Wash with ice cold water and dry to constant weight at 60° C. to yield the title compound. (Yield: 168.2 g (HPLC purity 94%), m.p. 183°–185° C., 89% of theory).

E. 8-CHLORO-11-(1-METHYL-4-PIPERIDYLIDENE)-6,11-DIHYDRO-5H-BENZO[5,6]CYCLOHEPTA[1,2-b]PYRIDINE

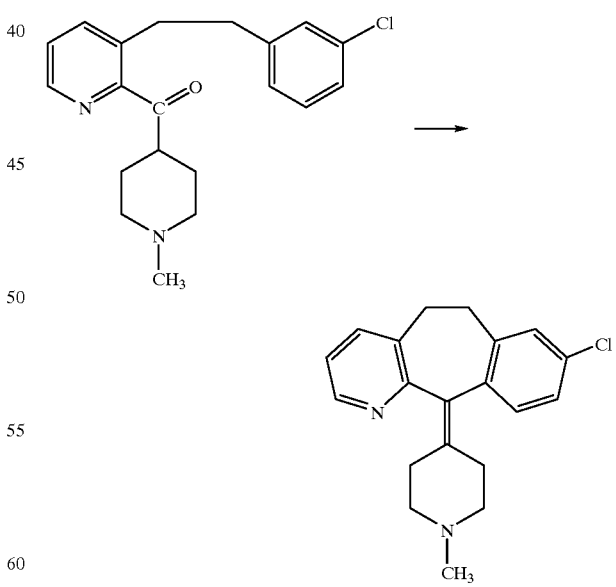

Dissolve the title compound of Preparative Example 1D above (59 g, 0.15 mole) in HF (120 mL, 120 g, 6.0 mole) at −35° C. and add BF₃ (44.3 g, 0.66 mole) over 1 hour. Determine completeness of the reaction by thin layer chromatography. Quench the reaction using ice, water and KOH bringing the solution to a final pH of 10. Extract the product with toluene and wash with water and brine. Concentrate the toluene solution to a residue, and dissolve in hot hexane. Remove the insolubles by filtration and concentrate the filtrate to yield the title compound as an off-white powder. (Yield: 45.7 g (HPLC purity: 95%), 92% of theory).

Alternative Step E: 8-CHLORO-11-(1-METHYL-4-PIPERIDYLIDENE)-6,11-DIHYDRO-5H-BENZO[5,6CYCLOHEPTA[1,2-b]PYRIDINE React the title compound of Preparative Example 1D above (177 g, 0.49 mole) in trifluoromethanesulfonic acid (480 ml, 814.1 g, 5.31 mole) at 90–95° C. for 18 hours under nitrogen. Determine the completeness of the reaction by thin layer chromatography. Cool the reaction and quench the reaction with ice-water and adjust the pH to 6 with $BaCO_3$. Extract the product with $CH_2Cl_2$, and concentrate under reduced pressure to about 1 liter. Wash with water, and extract the product into 1 N HCl which is treated with 30 g of activated charcoal, and filter through celite. Adjust the pH of the filtrate to 10 with aqueous NaOH (50%), extract the product into $CH_2Cl_2$, and remove under reduced pressure to form a residue. Dissolve the residue in hot hexane, and filter to remove insolubles. Concentrate the filtrate to yield the title compound as a beige powder. (Yield: 126 g (HPLC purity 80%), 65% of theory).

F. 8-CHLORO-11-(1-ETHOXYCARBONYL-4-PIPERIDYLIDENE)-6,11-DIHYDRO-5H-BENZO[5,6]CYCLOHEPTA[1,2-b]PYRIDINE

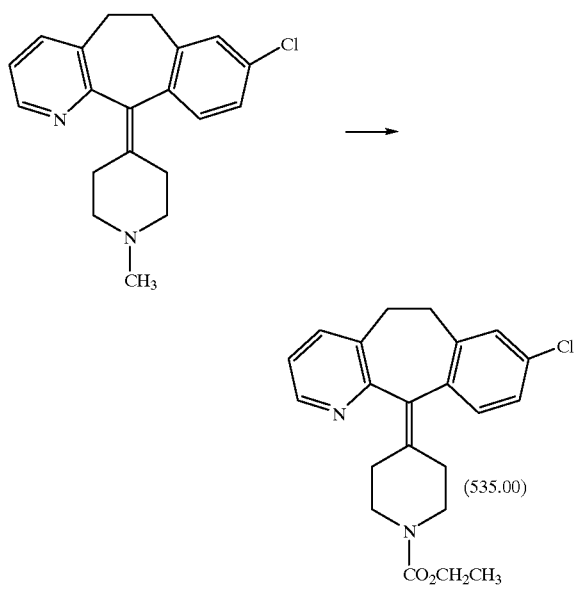

Dissolve the title compound of Preparative Example 1E above (45.6 g, 0.141 mole) in toluene (320 mL) at 80° C. and to it gradually add ethyl chloroformate (40.4 mL, 45.9 g, 0.423 mole). Following complete addition, maintain the temperature at 80° C. for 1 hour, then add diisopropylethylamine (2.7 mL, 2.00 g, 0.016 mole) and additional ethyl chloroformate (4.1 mL, 4.65 g, 0.0429 mole). Monitor completeness of the reaction by thin layer chromatography. Upon completion, cool the reaction mixture to ambient temperature, and wash the toluene solution with water. Concentrate the organic layer to a residue and dissolve in hot $CH_3CN$ (320 mL). Decolorize the solution with 14 g of activated charcoal. Remove the activated charcoal by filtration and concentrate the filtrate to a crystalline slurry. Cool the mixture to 0–5° C., and isolate the product by filtration. Wash with cold $CH_3CN$ and dry the product at below 70° C. to yield compound 535.00. (Yield: 42.4 g (HPLC purity 97.4%), 80% of theory).

G. 8-CHLORO-11-(4-PIPERIDYLIDENE)-6,11-DIHYDRO-5H-BENZO[5,6]CYCLOHEPTA[1,2-b]PYRIDINE

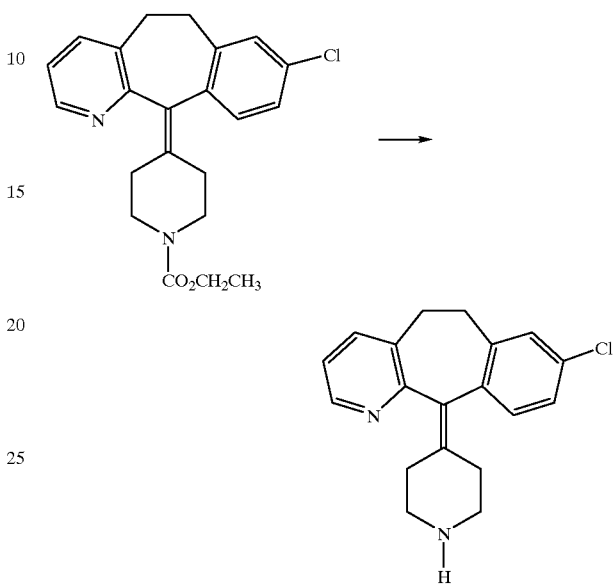

Hydrolize the title compound of Preparative Example 1F, 8-chloro-11-(1-ethoxycarbonyl-4-piperidylidene)-6,11-dihydro-5H-benzo[5,6]cyclohepta[1,2-b]pyridine (39 g, 0.101 mole) with KOH (50 g) in EtOH (305 mL) and water (270 mL) at reflux under an argon atmosphere for 64 hours. Partially distill off the EtOH and dilute the residue with brine, and extract with EtOAc (3×). Wash the combined organic phases with water and dry with $Na_2SO_4$. Remove the solvent to give a solid which can be recrystallized from toluene to give the title compound as a white solid. (Yield: 24.5 g, 77%, melting point 154–155° C.).

H. By substituting in step 1B above, the benzylic halides:

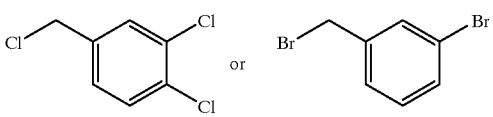

for meta-chlorobenzylchloride, and employing basically the same methods as steps C through G, the compounds (I)

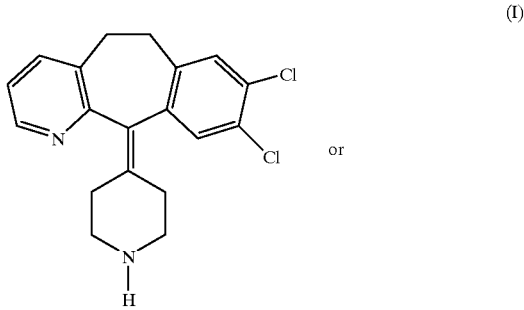

-continued

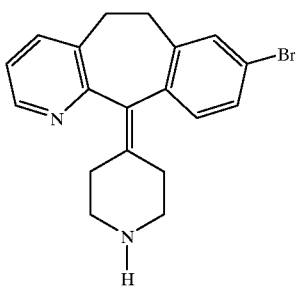

(II)

respectively, are prepared. Dichloro compound (I) is recrystallized from toluene and has a melting point of 150–152° C. Bromo compound (II) has a melting point of 146–148° C.

PREPARATIVE EXAMPLE 2
A. 3,5-DIMETHYLPYRIDINIUM N-OXIDE

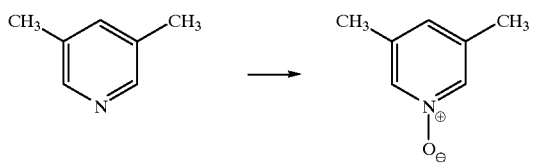

A solution of 285 mL (1.31 mol) of 35% peracetic acid was slowly added to a stirred solution of 149 g (1.39 mol) of 3,5-dimethylpyridine during which the temperature rose to 85° C. and was maintained at this temperature during addition. After the temperature of the mixture dropped to about 35° C. the reaction was stored at 5° C. overnight.

After partial removal of 185 ml of acetic acid via distillation under vacuum, the reaction was washed with NaHSO$_4$ solution and then neutralized with 10% NaOH solution to pH of about 7. The product was extracted with CH$_2$Cl$_2$ to give the title compound as a white solid (yield 142 g, 83%).

B. 1-METHOXY-3,5-DIMETHYLPYRIDINIUM METHYL SULFATE

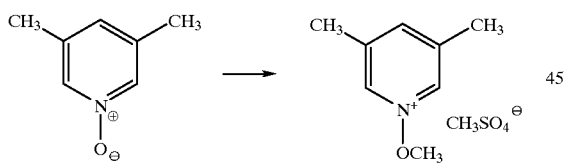

Dimethylsulfate (42.0 g, 0.33 mol) was slowly added to 41.0 g (0.33 mol) of 3,5-dimethylpyridinium N-oxide with mechanical stirring. The mixture was then heated on a steam bath for 1 hr. Then vacuum was applied while cooling to give a brownish solid of the title compound in quantitative yield.

C. 2-CYANO-3,5-DIMETHYLPYRIDINE

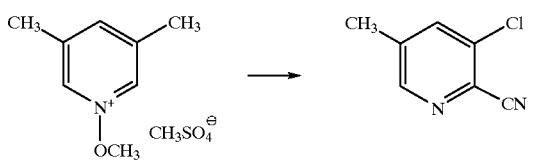

To a cooled (0° C.) solution of NaCN (49.0 g, 0.999 mol, 3.0 eq.) in 135 mL of water (air free) was dripped 1-methoxy-3,5-dimethyl pyridinium methyl sulfate (83.0 g, 0.33 mol) in 100 mL water (air free) in 1.25 hr., keeping the temperature below 3° C. The reaction mixture was stored at about 3° C. overnight. The mixture was filtered and washed with water to give 40 g of the title compound. An analytical sample was recrystallized from isopropyl ether and pentane (4:1) (m.p.: 61–62° C.).

D. N-(1,1-DIMETHYLETHYL)-3,5-DIMETHYL-2-PYRIDINE CARBOXAMIDE

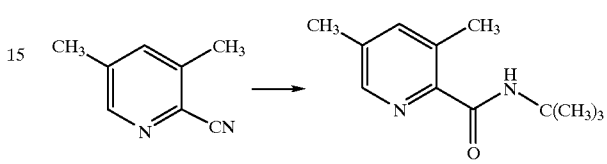

To a stirred solution of 20.3 g (0.153 mol) of 2-cyano-3,5-dimethylpyridine in 100 mL of 20 mL of conc. H$_2$SO$_4$ within 10 minutes, followed by 20 mL of t-butanol over an additional 15 minutes. The solution was warmed at 75° C. for 30 minutes after which it was cooled to room temperature and basified with 25% NaOH. The product was extracted 3× with EtOAc (600 mL), which was combined and washed 1× with brine, dried (Na$_2$SO$_4$), filtered and concentrated in vacuo to give the title compound (31.26 g) as a yellowish oil.

E. 8-CHLORO-3-METHYL-11-(4-PIPERIDYLIDENE)-6,11-DIHYDRO-5H-BENZO[5,6]CYCLOHEPTA[1,2-b]PYRIDINE

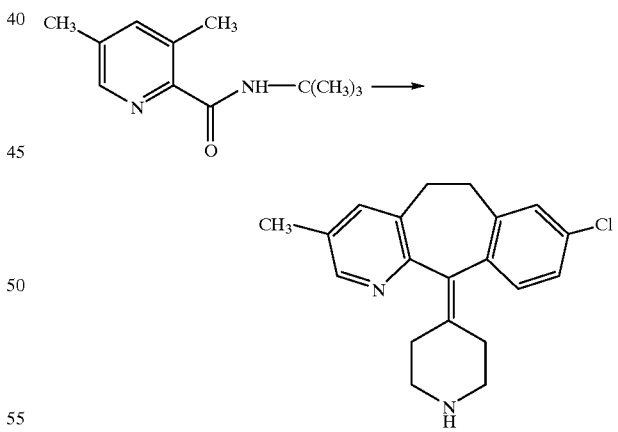

By substituting in step 1B above N-(1,1-dimethylethyl)-3,5-dimethyl-2-pyridine carboxamide for N-(1,1-dimethylethyl)-3-methyl-2-pyridine carboxamide and employing basically the same methods as steps B through G of Preparative Example 1, one obtains 8-chloro-3-methyl-11-(4-piperidylidene)-6,11-dihydro-5H-benzo[5,6]cyclohepta[1,2-b]pyridine. Reaction times are determined by TLC or HPLC.

PREPARATIVE EXAMPLE 3

By substituting

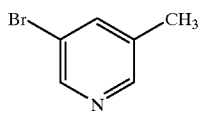

for 3,5-dimethylpyridine in Preparative Example 2 above and following basically the same procedure (steps A–E), the compound

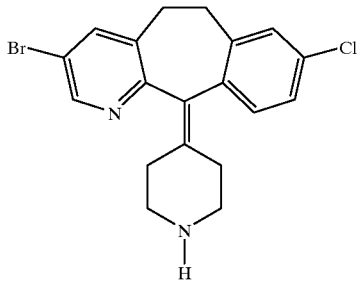

can be prepared. Note that the addition of the nitrile group to the pyridine in step C of Preparative Example 2 can result in the formation of other undesirable isomers which can be removed via flash chromatography.

PREPARATIVE EXAMPLE 4

A. 8-CHLORO-5,6-DIHYDRO-11H-BENZO[5,6]CYCLOHEPTA-[1,2-b]PYRIDIN-11-ONE N-OXIDE

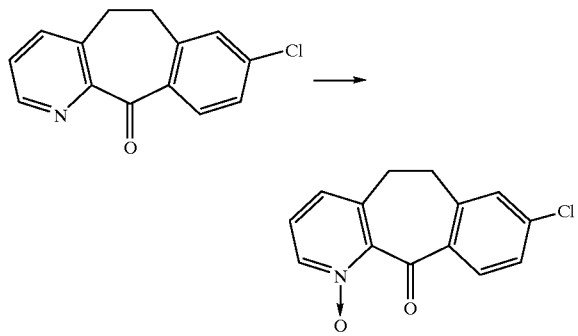

To a mixture of 25.1 grams (0.103 mole) of 8-chloro-5,6-dihydro-11H-benzo[5,6]cyclohepta[1,2-b]pyridin-11-one in 175 ml of dry $CH_2Cl_2$ at 0° C. under an argon atmosphere was added dropwise over 70 minutes a solution of 24.12 grams of MCPBA in 150 ml of $CH_2Cl_2$. After the addition the solution was stirred for ½ hour after which the ice bath was removed. After two days the reaction was poured into 1.0 N aqueous NaOH and extracted with $CH_2Cl_2$. The organic portions were combined, washed once with water, dried over $MaSO_4$, filtered and concentrated in vacuo. The resultant product was triturated with isopropyl ether and filtered to provide 25.8 grams (96%) yield of the title compound.

B. 2,8-DICHLORO-5,6-DIHYDRO-11H-BENZO[5,6]CYCLO-HEPTA[1,2-b]PYRIDIN-11-ONE AND 4,8-DICHLORO-5,6-DIHYDRO-11H-BENZO[5,6]CYCLOHEPTA[1,2-b]PYRIDIN-11-ONE

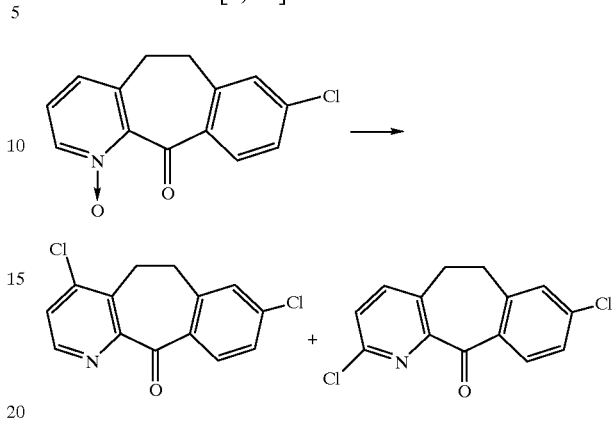

To a mixture of 29.13 grams (112.2 mmol) of the title compound from Preparative Example 4A above, in 40 ml of dry $CH_2Cl_2$ at 0° C. and under argon atmosphere was added 500 ml of 1.0 M $SO_2Cl_2$ dropwise over 1 hour. The ice bath was then removed and the reaction stirred at room temperature for 1 hr and then refluxed for seven hours. The mixture was poured into 1.0 N aqueous NaOH and extracted three times with $CH_2Cl_2$. The organic portions were combined, dried over $MgSO_4$, filtered and concentrated in vacuo to yield a product which was purified and separated via flash chromatography to yield the two title compounds.

Alternatively, A mixture of 1 gram of the title compound from Preparative Example 4A above, in phosphorus oxychloride (7 ml), was heated at 107° C. in a silicone bath for 4.5 h. The mixture was evaporated to dryness and the residue was taken up in $CH_2Cl_2$ and the latter was washed with saturated aqueous $NaHCO_3$. The $CH_2Cl_2$ layer was dried ($MgSO_4$), filtered and evaporated to give a mixture of the two title compounds. The mixture was separated by column chromatography on a silica gel column using a 0.25% solution of 10% concentrated $NH_4OH$ in MeOH in $CH_2Cl_2$ as the eluant to give the 2-chloro compound (Yield: 0.4457 g., 42%, MH+ 278) and the 4-chloro compound (Yield: 0.5358 g., 51%, MH+ 278), the N-oxide group having been removed under the reaction conditions used in the reaction.

C. 4-(2,8-DICHLORO-5,6-DIHYDRO-11H-BENZO[5,6]CYCLOHEPTA[1,2-b]PYRIDIN-11-YLIDENE)PIPERIDINE AND 4-(4,8-DICHLORO-5,6-DIHYDRO-11H-BENZO[5,6]CYCLOHEPTA-[1,2-b]-PYRIDIN-11-YLIDENE)PIPERIDINE

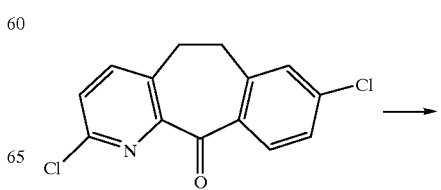

-continued

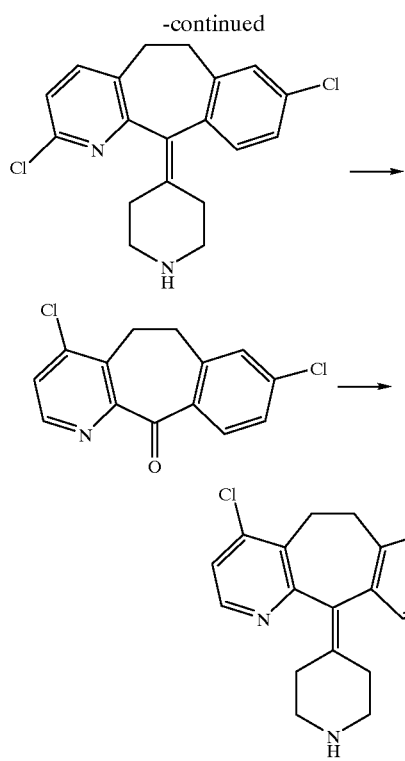

By following essentially the same procedure as that described in parts E TO H of Example 2 below, the 2,8-dichloro and 4,8-dichloro products of Preparative Example 4B above were converted to the corresponding title compounds of Preparative Example 4C.

PREPARATIVE EXAMPLE 5

To phosphorous oxychloride (256 mL) stirring at reflux was added dropwise a solution of compound 515.00 (109 grams) from Example 1 dissolved in CHCl₃ (850 mL). After stirring the resulting solution for an additional 20 minutes at reflux, the reaction mixture was cooled to room temperature and the CHCl₃ removed in vacuo. The resulting solution was cooled in an ice-water bath and to it was slowly added 1N aqueous NaOH (850 mL) followed by 50% aqueous NaOH until the resulting mixture was slightly basic. Extraction with EtOAc, drying of the organic phase over anhydrous MgSO₄, concentration in vacuo, and purification by flash column chromatography provided the 4,8-dichloro product, 596.00, (27 grams, 23% yield, mp 141.6–145.6° C.) and the 2,8-dichloro product, 515.01,

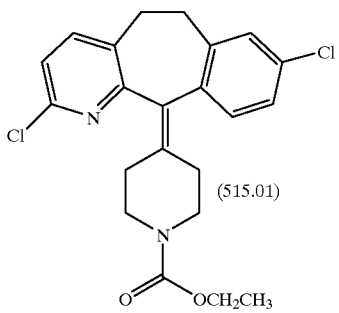

(515.01)

(9 grams, 8% yield, mp 176.5–177.9° C.).

PREPARATIVE EXAMPLE 6
4-(8-CHLORO-4-METHOXY-5,6-DIHYDRO-11H-BENZO[5,6]-CYCLOHEPTA]1,2-b]PYRIDIN-11-YLIDENE)PIPERIDINE

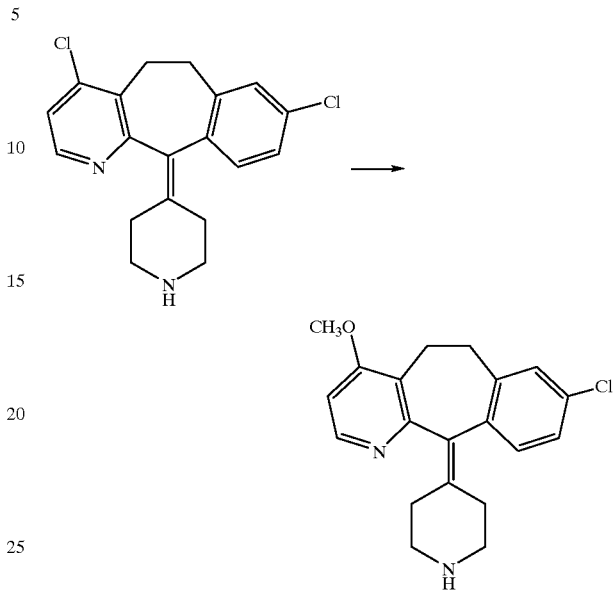

A mixture of 212 mg of the 4,8-dichloro title compound of Preparative Example 5C above, 7 ml of 2.0 N aqueous KOH and 7 ml of MeOH were heated at 135° C. under a nitrogen atmosphere in a sealed pressure vessel for 18 hours. The vessel was then cooled to room temperature. The mixture was poured into water and extracted three times with CH₂Cl₂. The organic portions were combined, dried over MgSO₄, filtered and concentrated in vacuo to provide a residue which was purified via flash chromatography (4→7% MeOH saturated with NH₄OH in CH₂Cl₂) and then triturated with isopropyl ether/CH₂Cl₂ to provide 144 mg of the title compound as a white glass.

PREPARATIVE EXAMPLE 7
A. 8-CHLORO-6,11-DIHYDRO-11-HYDROXY-5H-BENZO[5,6]-CYCLOHEPTA[1,2-b]PYRIDINE

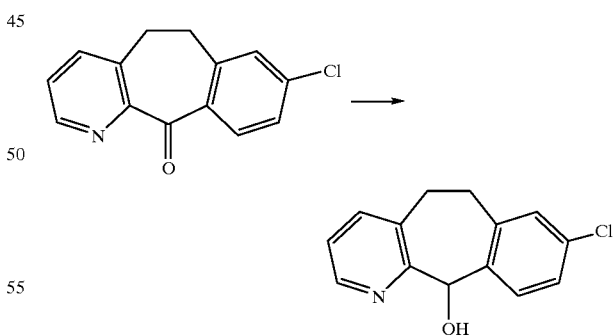

To a mixture of 25.03 g (103 mmol) of 8-chloro-5,6-dihydro-11H-benzo[5,6]cyclohepta[1,2-b]pyridin-11-one in 200 mL of MeOH at room temperature and under a nitrogen atmosphere was added portionwise over a period of about 1 hour 4.82 g (124 mmol) of NaBH₄. Occasional cooling with an ice bath was necessary at times during the addition in order to avoid excessive reflux. After 1.6 hours the mixture was poured into ice cold water and then extracted with EtOAc (3×). The combined organic portions were washed with brine, dried over MgSO$_4$, filtered, and concentrated in vacuo. The residue was recrystallized from hot isopropyl ether. The remaining filtrate was purified via flash chromatography (20% EtOAc in hexanes) to yield more product which solidified on standing. Both batches were combined to yield 20.41 g of the title compound as a white solid.

B. 8,11-DICHLORO-6,11-DIHYDRO-5H-BENZO[5,6]CYCLOHEPTA[1,2-b]PYRIDINE

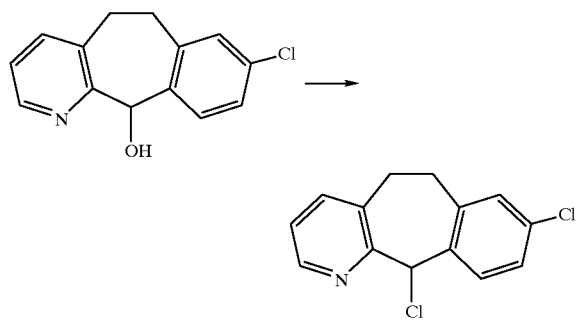

To a mixture of 13.3 g (54 mmol) of 8-chloro-6,11-dihydro-11-hydroxy-5H-benzo[5,6]cyclohepta[1,2-b]pyridine in 290 mL of toluene at −15° C. and under an atmosphere of nitrogen was added via syringe pump over a period of 1 hour 6.20 mL (85.7 mmol) of SOCl$_2$. The extent of reaction was monitored by TLC (50% EtOAc in hexanes). When completed the mixture was poured into 300 mL of 1.0 N aqueous NaOH and extracted with EtOAc (5×). The combined organic portions were washed with brine, dried over Na$_2$SO$_4$, filtered, and concentrated in vacuo. The residue was taken up in EtOAc, quickly filtered through basic alumina, and concentrated again to yield a product which was triturated with pentane to yield 10.22 g of the title compound as a tan solid.

C. 8-CHLORO-11-(1-PIPERAZINYL)-6,11-DIHYDRO-5H-BENZO[5,6]CYCLOHEPTA[1,2-b]PYRIDINE

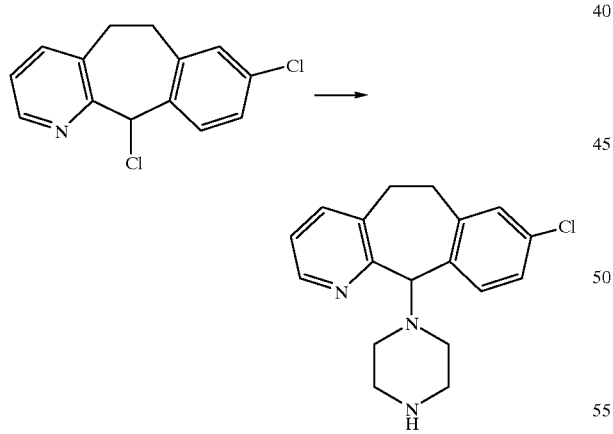

To a mixture of 10.0 g (37.9 mmol) of 8,11-dichloro-6,11-dihydro-5H-benzo[5,6]cyclohepta[1,2-b]pyridine and 1.0 mL of Et$_3$N in 200 mL of dry THF at room temperature and under a nitrogen atmosphere was added 33.0 g of piperazine. The mixture was stirred at room temperature for 22.5 hours and then refluxed for 5.5 hours. It was then cooled to room temperature, poured into 250 mL of 5% aqueous NaOH, and extracted with CH$_2$Cl$_2$ (3×). The combined organic portions were washed with brine, dried over MgSO$_4$, filtered, and concentrated in vacuo. The residue was purified via flash chromatography (2→5% MeOH saturated with NH$_4$OH in CH$_2$Cl$_2$) to yield the title compound as a glass.

PREPARATIVE EXAMPLE 8

PREPARATION OF THE R(+) AND S(−) DIASTEREOISOMERS

The racemic 8-chloro-11-(1-piperazinyl)-6,11-dihydro-5H-benzo-[5,6]cyclohepta[1,2-b]pyridine prepared in Preparative Example 7C above was resolved by the method described in Preparative Example 15A–C, pages 116–118, of WO 92/00293, published Jan. 9, 1992, to give the R(+) and S(−) diastereoisomers:

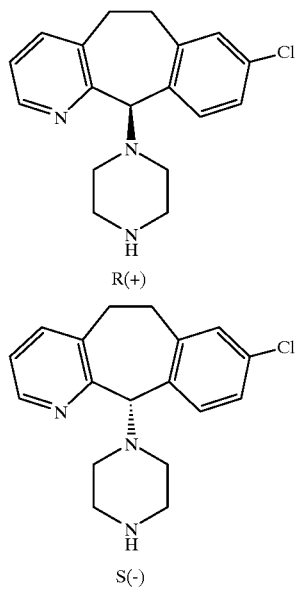

PREPARATIVE EXAMPLE 9

A. 4-(8-CHLORO-3-NITRO-5,6-DIHYDRO-11-(4-PIPERIDYLIDENE)-11H-BENZO[5,6]CYCLOHEPTA[1,2-b]PYRIDINE.

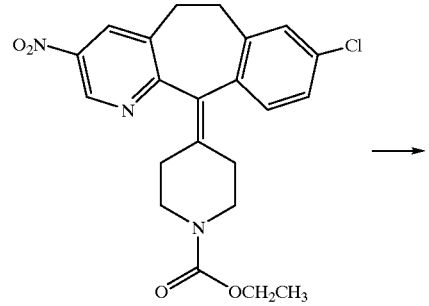

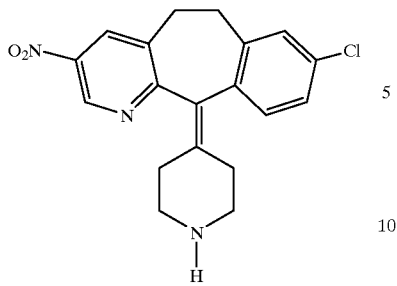

Hydrolyze the title compound of Example 31A (10.0 g, mmol) by dissolving in conc. HCl (250 mL) and heating to 100° C. for 16 h. The cooled acidic mixture was neutralized with 1M NaOH (950 mL). The mixture was extracted with CH₂Cl₂. The latter was dried over MgSO₄. Filtration and concentration afforded the title compound in 99% yield as a solid. MH+ 358.

PREPARATIVE EXAMPLE 10

8-CHLORO-11-(1-PIPERAZINYL)-11H-BENZO[5,6]CYCLOHEPTA[1,2b]PYRIDINE

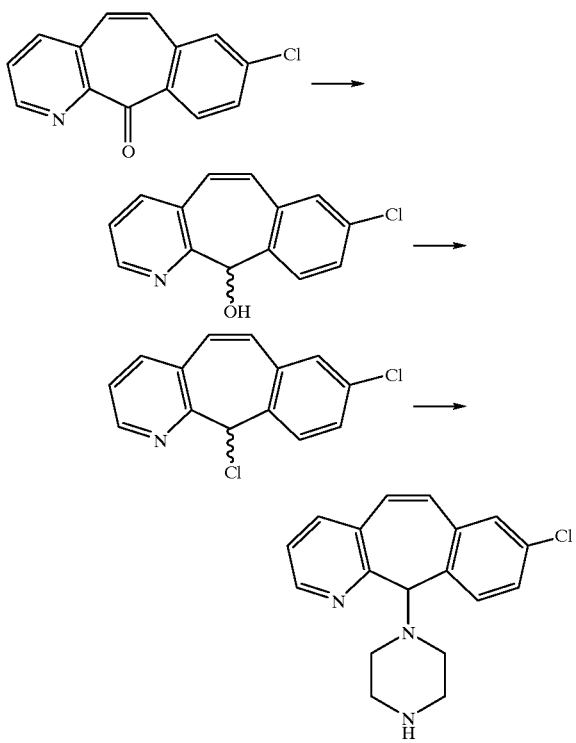

The preparation of the starting material for this reaction was described in *The Journal of Organic Chemistry*, 1990, 55, pp. 3341–3350 by Piwinski, et al. By substituting in Preparative Example 7A, 8-chloro-11H-benzo[5,6]cyclohepta[1,2-b]pyridin-11-one (11.53 g) (47.71 mmoles) for 8-chloro-5,6-dihydro-11H-benzo[5,6]cyclohepta[1,2-b]pyridin-11-one and employing basically the same methods as steps A through C of Preparative Example 7, one obtains 11.53 g (36%) of the title compound (MH+ 312).

PREPARATIVE EXAMPLE 11

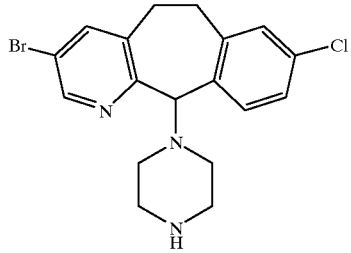

Step A:

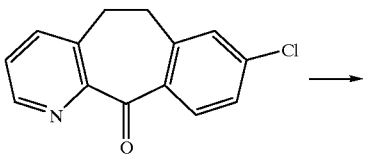

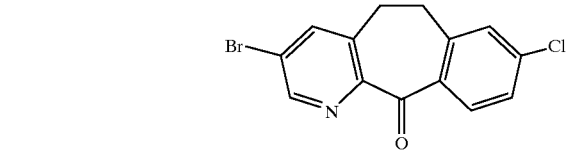

Cool 50.0 g (20.5 mmol) of 8-Chloro-5,6-dihydro-11H-benzo[5,6]cyclohepta[1,2-b]pyridin-11-one to 0° C. and slowly add 75 mL of sulfur monochloride over 20 minutes. Add 25 mL (48.59 mmol) of Br₂ over 15 minutes, then heat at 95° C. for 20 hours. Add 12.5 mL (24.3 mmol) of Br₂ over 15 minutes and heat for 24 hours more. Cool the mixture and slowly add it to a mixture of CH₂Cl₂ and 1N NaOH (aqueous) at 0° C. Wash the organic phase with water dry over MgSO₄, and concentrate in vacuo to a residue. Chromatograph (silica gel, 500 mL of CH₂Cl₂, then 0.2%–5% (10% concentrated NH₄OH in MeOH)-CH₂Cl₂), then rechromatograph (silica gel, 3–8.5% EtOAc/hexane) to give 8.66 g of the product compound. Mass Spec.: MH⁺=322.

Step B:

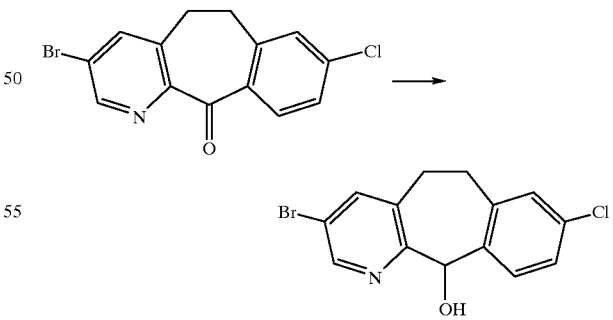

Combine 6.84 g (21.2 mmol) of the product of Step A 160.5 mL of MeOH and treat with 1.1709 g of NaBH₄ as described in Preparative Example 7, Step A, to give 5.93 g of the product compound. MH⁺ 326.

Step C:

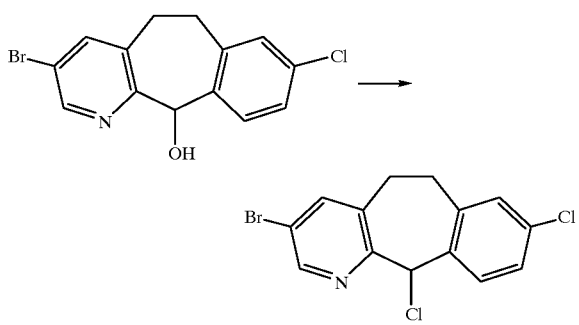

Combine 5.93 g (18.3 mmol) of the product of Step B and 116 mL of anhydrous toluene, cool to 0° C., and slowly add (dropwise) a solution of 2.465 g (33.9 mmol) of SOCl₂ in 23 mL of anhydrous toluene over a period of 0.5 hours. Stir at 0° C. for 1.5 hours and at 0°–25° C. for 2 hours, then work up as described in Preparative Example 7, Step B, to give the product compound.

Step D:

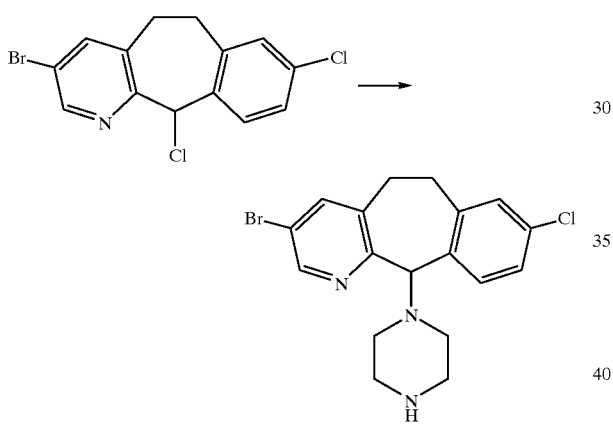

React 18.3 mmol of the product of Step C with 9.94 g (91.5 mmol) of piperazine via the procedure described in Preparative Example 7, Step C, to give 8.0 g of the title compound. Mass Spec.: MH⁺=394.

PREPARATIVE EXAMPLE 12

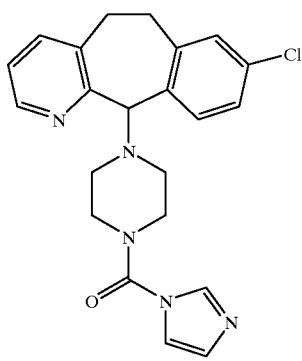

Combine 10 g (31.9 mmol) of the product of Preparative Example 7, Step C, 100 mL of dry CH₂Cl₂ and slowly (dropwise) add the solution to a mixture of 5.17 g (31.9 mmol) of carbonyldiimidazole in 150 mL of dry CH₂Cl₂ over 0.75 hours. Stir at 0° C. for 2 hours, wash with water, dry over MgSO₄, and concentrate in vacuo to a residue. Chromatograph (silica gel, 2% (10% conc. NH₄OH in MeOH)/CH₂Cl₂) to give 8.71 g of the title compound. Mass Spec.: MH⁺=408.2.

Using the product of Preparative Example 11, Step D, and essentially the same procedure as described for Preparative Example 12, the following compound is prepared:

Preparative Example 12-A

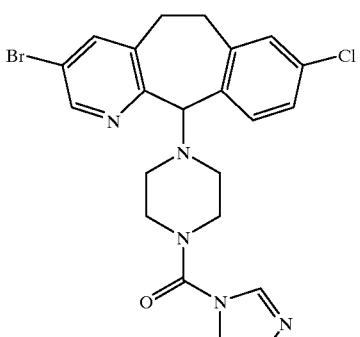

Mass Spec.: MH⁺ = 488.2

PREPARATIVE EXAMPLE 13

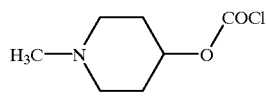

Combine 10 mL of dry CH₂Cl₂ and 914.6 mL (28.1 mmol) of a 1.93 M solution of phosgene in toluene, cool to 0° C. and slowly add (dropwise) a solution of 0.6484 g (5.62 mmol) of 3-hydroxy-1-N-methylpiperidine, 1.214 mL (15 mmol) of pyridine and 10 mL of dry CH₂Cl₂, over 10 min., then stir at 0°–25° C. for 2 hours. Purge excess phosgene with N₂ then concentrate in vacuo to give the title compound.

EXAMPLE 1

ETHYL 4-(8-CHLORO-5,6-DIHYDRO-11H-BENZO[5,6] CYCLOHEPTA[1,2-B]PYRIDIN-11-YLIDENE)-1-PIPERIDINECARBOXYLATE N-OXIDE

To a mixture of 5.10 gms of ethyl 4-(8-chloro-5,6-dihydro-11H-benzo[5,6]cyclohepta[1,2-b]pyridin-11-ylidene)-1-piperidinecarboxylate (535.00) in 100 ml of dry CH₂Cl₂ at −15° C. and under an atmosphere of nitrogen was added portionwise over 15 min 2.80 gms of meta-peroxybenzoic acid. After 15 minutes the ice bath was removed and the reaction mixture was slowly warmed to room temperature. After 2.25 hours a solution of 10% aqueous NaHSO₃ was added and the mixture was stirred for an additional 5 minutes. Following its basification with a solution of 15% aqueous NaOH, the organic layer was isolated, and subsequently washed once each with 15% aqueous NaOH and water. The organic phase was then dried over MgSO₄, filtered, and concentrated in vacuo. The product, 515.00, was purified via flash chromatography to yield the product as a white solid: MS (FAB) m/z 399 (M⁺=1).

EXAMPLE 2

A. N-(1,1-DIMETHYLETHYL)-2-BROMO-3-[2-(3-CHLOROPHENYL)-ETHYL]-2-PYRIDINE CARBOXAMIDE

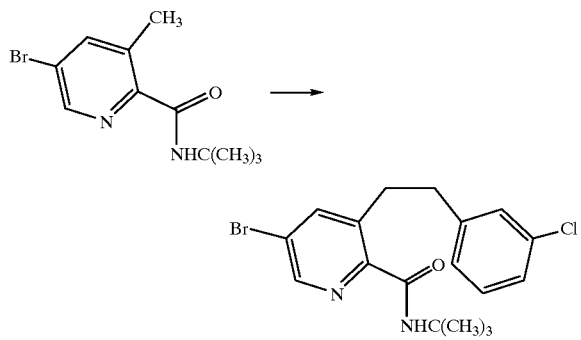

Cool diisopropylamine dissolved in THF (60 mL) to 0–5° C. Add n-butyl lithium(39 mL, 97.99 mmol.) and stir the reaction at that temperature for 30 min. Canulate this reaction mixture to a cooled solution of N-(1,1-dimethylethyl)-2-bromo-3-methyl pyridine carboxamide (9.91 g, 97.99 mmol) in dry THF (250 mL) (−70° C.). Stir for 0.5 h then add 3-chlorobenzyl bromide(11.4 g, 55.31 mmol) dissolved in 50 mL of THF. Stir the reaction mixture for 0.5 h. Quench the reaction with water and extract the products twice with EtOAc. Dry the organic phase over $Na_2SO_4$, filter and chromatograph on silica gel column eluting with 3% MeOH solution in $CH_2Cl_2$ to give the title compound (15 g, Yield 60%).

B. 2-BROMO-3-[2-(3-CHLOROPHENYL)-ETHYL]-2-PYRIDINE CARBONITRILE

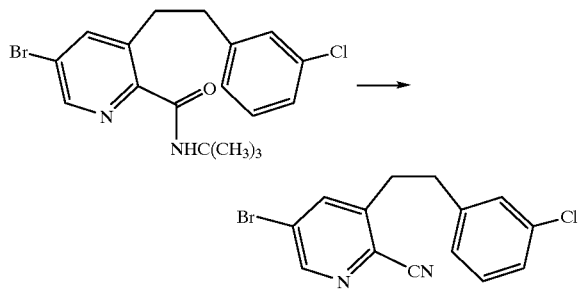

Dissolve the title compound of Example 2A above (11.34 g, 31.6 mmol) in toluene (80 mL) and add $POCl_3$ (10 mL). Reflux the reaction mixture for 3 h and then stir at room temperature overnight. Evaporate all the volatiles and partion the resulting solid between 1N NaOH and EtOAc. Wash the aqueous phase with EtOAc twice. Wash the organic phase with brine and dry it with $Na_2SO_4$. Remove the solvents to give the title compound as a white solid (9.68 g, Yield 96%).

C. 3-BROMO-8-CHLORO-5,6-DIHYDRO-11H-BENZO[5,6]-CYCLOHEPTA[1,2-b]PYRIDIN-11-ONE.

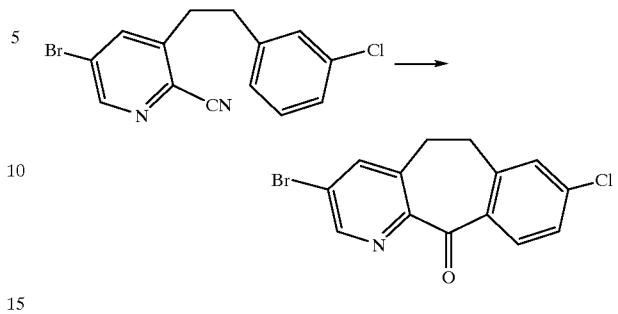

Cyclize 3-[2-(3-chlorophenyl)ethyl]-4-bromo-2-pyridine carbonitrile(10.7 g, 32.8 mmol) in triflic acid (82 mL) at 60° C. for 2 hours and then at room temperature for 2 hours. Add 80 mL of 5N HCl carefully, then reflux in an oil bath(120° C.) for 30 minutes. Cool the solution and pour into ice and basify with 25% NaOH solution. Extract the product with $CH_2Cl_2$ and wash with brine. Dry the organic layer with $Na_2SO_4$, filter and remove the solvent to give crude product (10.4 g). Purify the crude product with flash chromatography on silica gel and elute with 15% EtOAc-hexane to give the title compound as a white solid (9 g, 27.95 mmol, Yield 85.2% $MH^+$ 322).

D. 8-CHLORO-3-METHOXY-5,6-DIHYDRO-11H-BENZO[5,6L-CYCLOHEPTA[1,2-b]PYRIDIN-11-ONE.

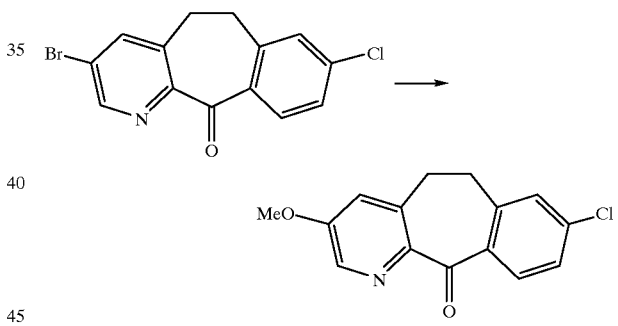

Dissolve the title compound from Example 2C (2.37 g, 7.4 mmol) in dry MeOH and add Na metal(3.37 g, 180 mmol). Reaction is stirred overnight at room temperature. Reflux the reaction for 3 hours, cool to room temperature and extract with $CH_2Cl_2$-water. Dry the $CH_2Cl_2$ fraction and chromatograph on silica gel eluting with 50% EtOAc-hexanes to give the title compound as a light yellow solid (1.5 g, Yield 72% $MH^+$ 274).

E. 8-CHLORO-3-METHOXY-11-(1-METHYL-4-PIPERIDINYL)-6,11-DIHYDRO-5H-BENZO[5,6]-CYCLOHEPTA[1,2-b]PYRIDIN-11-OL

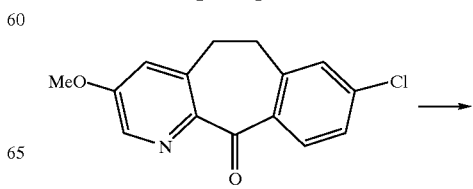

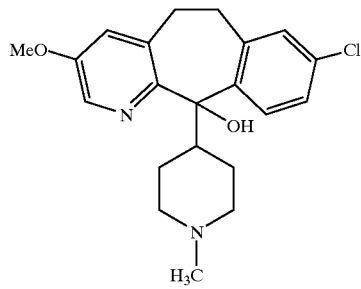

Dissolve the title compound from Example 2D above (1.45 g, 5.3 mmol) in THF (20 mL) and add slowly to a cooled (0° C.) solution of N-methyl-4-chloromagnesium piperidine (Grignard reagent) (4.4 mL, 1.2M). Stir the reaction for 2 h. Quench the reaction with NH$_4$Cl solution and extract with CH$_2$Cl$_2$ twice. Wash the organic phase with brine and dry over Na$_2$SO$_4$, filter and remove solvents.

Purify the residue with flash chromatography and elute with 5% and then 7% of methanolic ammonia dissolved in CH$_2$Cl$_2$ to give the title compound as a light yellow solid (1.1 g, Yield 57% MH$^+$ 373).

F. 8-CHLORO-3-METHOXY-11-(1-METHYL-4-PIPERIDYLENE)-6,11-DIHYDRO-5H-BENZO[5,6]-CYCLOHEPTA[1,2-b]PYRIDINE

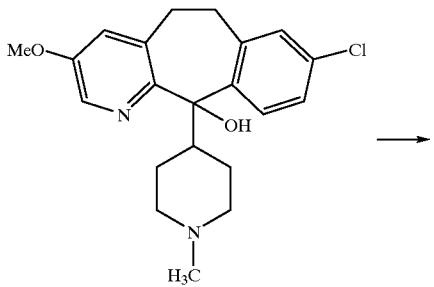

Dissolve the title compound of Example 2E above in concentrated H$_2$SO$_4$ and stir the reaction mixture at 80° C. for 2.5 h. Cool the reaction mixture to room temperature and then pour the reaction mixture onto ice and basify with 25% NaOH to pH 7. Extract with CH$_2$Cl$_2$ and wash the organic phase with brine. Dry the organic phase with MgSO$_4$, and remove the solvents. Purify on silica gel eluting with 5% methanolic ammonia dissolved in CH$_2$Cl$_2$ to give the title compound (0.38 g, Yield 36% MH+355).

G. 8-CHLORO-3-METHOXY-11-(1-ETHOXYCARBONYL-4-PIPERIDYLIDENE)-6,11-DIHYDRO-5H-BENZO[5,6]-CYCLOHEPTA[1,2-b]PYRIDINE

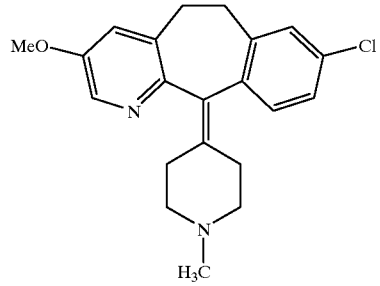

Stir a solution of the title compound of Example 2F (0.36 g, 1.01 mmol) and Et$_3$N (1 mL) in toluene at 80° C., add ethyl chloro-formate (1 mL) via a syringe. Stir the reaction at this temperature for 2 h, and at room temperature for 1 h. Adjust the pH to 7 with 1N NaOH and extract with EtOAc. On purification by flash chromatography, eluting with 70% EtOAc hexane, one obtains 8-chloro-3-methoxy-11-(1-ethoxycarbonyl-4-piperidylidene)-6,11-dihydro-5H-benzo[5,6]-cyclo-hepta[1,2-b]pyridine, 658.00, as a white solid (MH$^+$ 413).

H. 8-CHLORO-3-METHOXY-11-(4-PIPERIDYLIDENE)-6,11-DIHYDRO-5H-BENZO[5,6]-CYCLOHEPTA[1,2-b]PYRIDINE

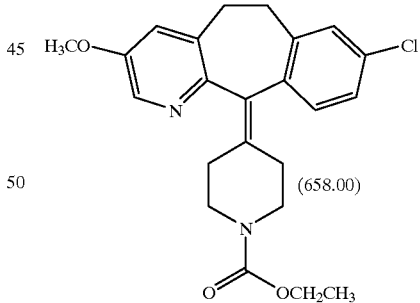

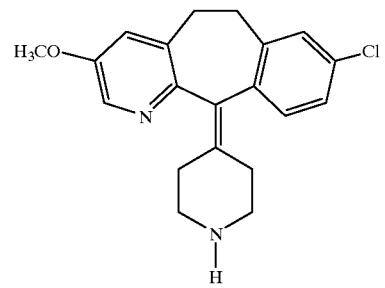

The title compound of Example 2H can be used to produce additional compounds. To obtain the title compound of Example 2H, reflux compound 658.00 from Example 2G (0.33 g, 0.8 mmol) with KOH (0.38 g, 6.9 mmol) in 10 mL of EtOH/water (1:1) overnight. Pour the reaction mixture into brine and extract with EtOAc, dry over $MgSO_4$, and filter. Remove the solvents to give the title compound (0.25 g, Yield 92%).

EXAMPLE 3
ETHYL 4-(8-CHLORO-6,11-DIHYDRO-11H-BENZO[5,6]CYCLOHEPTA[1,2-b]PYRIDIN-11-YL)-1-PIPERAZINECARBOXYLATE

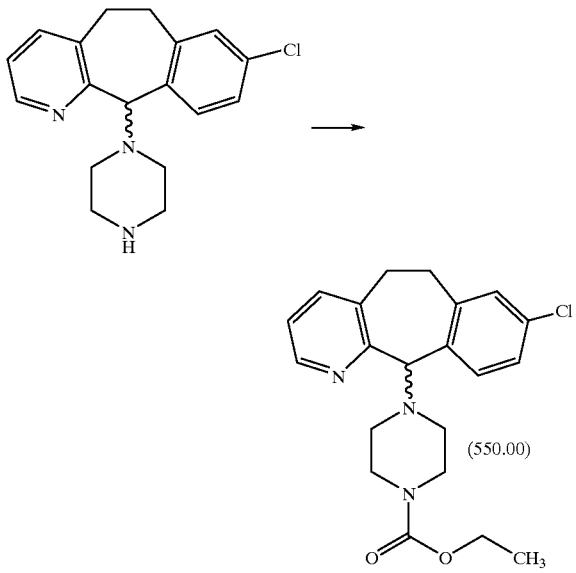

The title compound from Preparative Example 7C above (10 grams) (31.9 mmoles) was dissolved in dry THF (100 ml) and ethyl chloroformate (3.46 grams) (3.19 mmoles) was added in three portions to the stirred solution and the mixture was stirred at 250 for 1.5 h. The mixture was poured into $CH_2Cl_2$ and the latter was washed with saturated aqueus $NaHCO_3$, water and dried ($MgSO_4$). After filtration the $CH_2Cl_2$ was evaporated to dryness and the residue was chromatographed on silica gel using 0.5% (10% concentrated $NH_4OH$ in MeOH)-$CH_2Cl_2$ as the eluant to give compound 550.00 (Yield: 10.18 g., 83%, $MH^+$ 386.4).

EXAMPLE 4
PHENYL 4-(8-CHLORO-6,11-DIHYDRO-5H-BENZO[5,6]CYCLOHEPTA-[1,2-b]PYRIDIN-11-YL)-1-PIPERAZINECARBOXYLATE

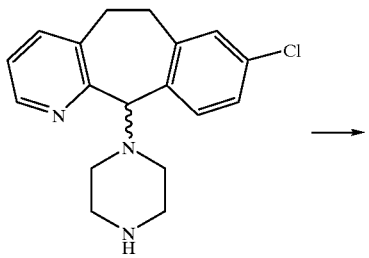

-continued

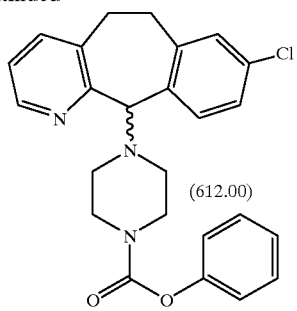

The title compound from Preparative Example 7C above (5 grams) (16.0 mmoles) and phenyl chloroformate (3.24 grams) (20.7 mmoles) were dissolved in dry pyridine (30 ml) and the mixture was stirred at 25° for 23 h.

The solution was diluted with $CH_2Cl_2$ and washed with saturated aqueous $NaHCO_3$ and then water. The $CH_2Cl_2$ was dried ($MgSO_4$), filtered and evaporated to dryness and the residue was azeotroped with toluene. The crude product was chromatographed on silica gel using 1% (10% concentrated $NH_4OH$ in MeOH)-$CH_2Cl_2$ as the eluant to give compound 612.00 (Yield: 6.1 g., 88%, $MH^+$ 434.2).

EXAMPLE 5
PHENYLMETHYL 4-(8-CHLORO-6,11-DIHYDRO-5H-BENZO[5,6]-CYCLOHEPTA[1,2-b]PYRIDIN-11-YL)-1-PIPERAZINECARBOXYLATE

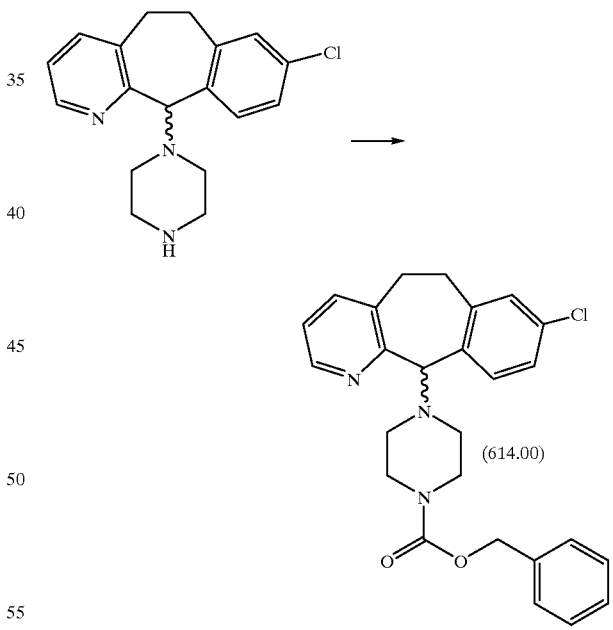

The title compound from Preparative Example 7C above (5 grams) (16.0 mmoles) was dissolved in dry pyridine (30 ml.) and benzylchloroformate (3.53 grams) (20.8 mmoles) was added. The mixture was stirred at 25° for 23 hours. Additional dry pyridine (30 ml.) and benzylchloroformate (7.06 grams) (41.6 mmoles) were added and the reaction was allowed to proceed at 25° for an additional 24 hours. The product was isolated and purified as in Example 4 above to give compound 614.00 (Yield: 3.87 grams, 54%, $MH^+$ 448).

EXAMPLE 6

A. 3-PYRIDYL CHLOROFORMATE

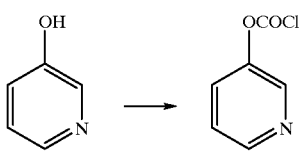

A 1.93M solution of phosgene in toluene (20%) (198.3 ml) (382.3 mmoles) was diluted with dry CH$_2$Cl$_2$ (100 ml) and the mixture was stirred at 0° under an argon atmosphere. A solution of 3-hydroxy-pyridine (7.27 grams) (76.5 mmoles) and dry pyridine (8.06 grams) (8.25 ml) (101.9 mmoles) in dry CH$_2$Cl$_2$ (200 ml) was added dropwise to the stirred solution at 0° over a period of 1 hour. The mixture was stirred at 0–25° for an additional 2 hours. A stream of nitrogen was passed through the solution to remove most of the phosgene and the solution was then evaporated to dryness to give the title compound which was dried in vacuo for 1 hour and then taken up in dry CH$_2$Cl$_2$ (60 ml) and dry pyridine (60 ml) to give a stock solution of the title compound.

B. 3-PYRIDYL 4-(8-CHLORO-6,11-DIHYDRO-5H-BENZO[5,6]-CYCLOHEPTA[1,2-b]PYRIDIN-11-YL)-1-PIPERAZINECARBOXYLATE

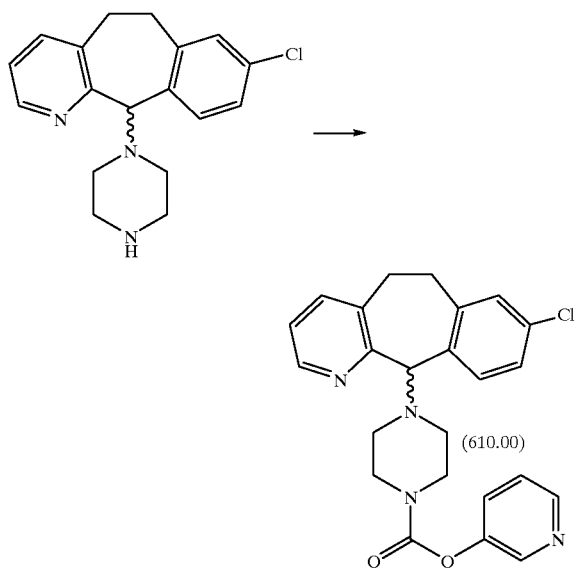

A portion of the stock solution of 3-pyridyl chloroformate (105 ml) prepared as described in Example 6A above and a solution of the title compound from Preparative Example 7C above (7 grams) in dry pyridine (30 ml) were stirred at 25° for 24 hours. The solution was evaporated to dryness and azeotroped with toluene. The residue was taken up in CH$_2$Cl$_2$ and washed with saturated aqueous NaHCO$_3$ and then water. The CH$_2$Cl$_2$ was dried (MgSO$_4$), filtered and evaporated to dryness. The residue was chromatographed on silica gel using 1% (10% concentrated NH$_4$OH in MeOH)-CH$_2$Cl$_2$ as the eluant to give compound 610.00 (Yield: 7.65 grams, 79%, MH$^+$ 435.15).

EXAMPLE 7

A. (+) ETHYL 4-(8-CHLORO-6,11-DIHYDRO-11H-BENZO[5,6]-CYCLOHEPTA[1,2-b]PYRIDIN-11(R)-YL)-1-PIPERAZINE CARBOXYLATE

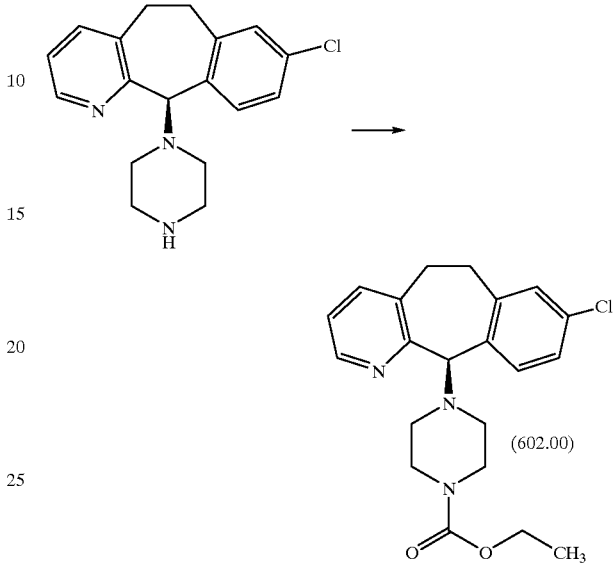

The title R(+) diastereoisomer from Preparative Example 8 above was reacted with ethyl chloroformate under the same conditions as described in Example 3 above to give compound 602.00 (Yield: 93%, MH$^+$386).

B. (−) ETHYL 4-(8-CHLORO-6,11-DIHYDRO-11H-BENZO[5,6]-CYCLOHEPTA[1,2-b]PYRIDIN-11(S)-YL)-1-PIPERAZINECARBOXYLATE

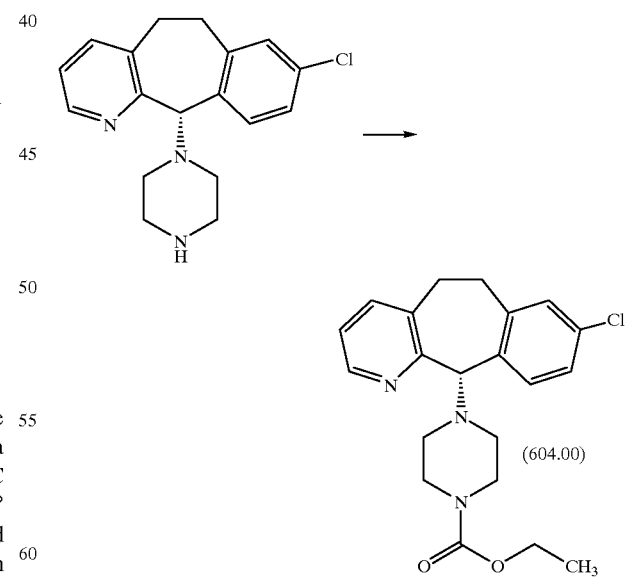

The title S(−) diastereoisomer from Preparative Example 8 above was reacted with ethyl chloroformate under the same conditions as described in Example 3 above to give compound 604.00 (Yield: 92%, MH$^+$ 386).

EXAMPLE 8

A. (+)3-PYRIDYL 4-(8-CHLORO-6,11-DIHYDRO-5H-BENZO[5,6]-CYCLOHEPTAR 1,2-b]PYRIDIN-11(R)-YL)-1-PIPERAZINE CARBOXYLATE

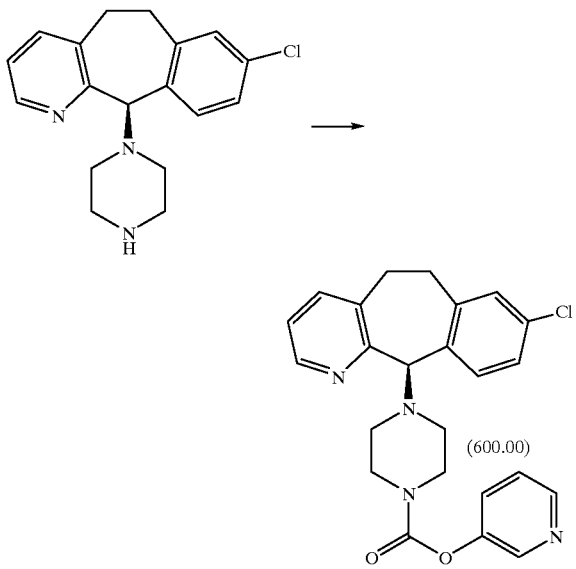

(600.00)

The title R(+) diastereoisomer from Preparative Example 8 above was reacted with 3-pyridyl chloroformate under the same conditions as described in Example 6B above to give compound 600.00(Yield: 71%, $MH^+$ 435).

B. (−) 3-PYRIDYL 4-(8-CHLORO-6,11-DIHYDRO-5H-BENZO[5,6]-CYCLOHEPTA[1,2-b]PYRIDIN-11(S)-YL)-1-PIPERAZINECARBOXYLATE

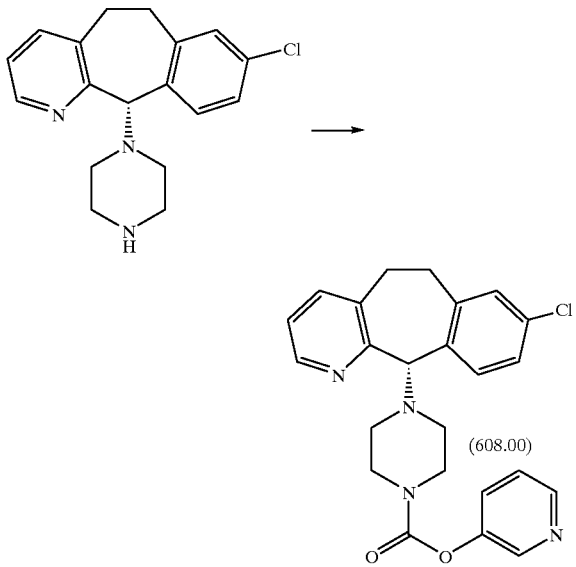

(608.00)

The title S(−) diastereoisomer from Preparative Example 8 above was reacted with 3-pyridyl chloroformate under the same conditions as described in Example 6B above to give compound 608.00 (Yield: 69%, $MH^+$ 435).

EXAMPLE 9

8-CHLORO-11-(1-ETHOXYCARBONYL-4-PIPERIDINYL)-11H-BENZO[5,6]CYCLOHEPTA[1,2-b]PYRIDINE

8-CHLORO-11-(1-ETHOXYCARBONYL-4-PIPERIDINYL)-9-ETHYL-11H-BENZO[5,6]CYCLOHEPTA[1,2-b]PYRIDINE

Compound 535.00 of Preparative Example 1F (51.15 grams, 0.1336 mole) was dissolved in trifluoromethane-sulfonic acid (170 mL). The dark mixture was heated to reflux for 70 h. The solution was cooled to room temperature and was then poured into 800 mL of an ice/water slurry and the resulting mixture stirred. Concentrated $NH_4OH$ solution (175 mL) was added to the mixture in small portions so that the temperature of the mixture was below 20° C. The resulting basic mixture was extracted with $CH_2Cl_2$. The $CH_2Cl_2$ extract was washed with brine and was then evaporated to give a brown residue. This residue was dissolved in $CH_2Cl_2$ (750 mL) and the solution cooled to 0° C. Ethyl chloroformate (14.8 grams, 0.136 mole) was added over 5 minutes and the resulting mixture stirred at 0° C. for 15 minutes. Saturated $NaHCO_3$ solution (150 mL) was added and the cooling bath was removed. The resulting biphasic mixture was stirred rapidly for 3 h. The layers were separated and the $CH_2Cl_2$ layer was filtered through silica gel. The filtrate was evaporated to dryness and the residue chromatographed on silica gel using a gradient of hexane-$CH_2Cl_2$-acetone 16:2.5:1.5 to hexane-$CH_2Cl_2$-acetone 28:7.5:4.5 as eluent to give compound 620.00 (25.02 g 49%, $MH^+$ 383) and compound 622.00 (4.85 g, 9%, $MH^+$ 411).

EXAMPLE 10

A. 8-CHLORO-11-(4-PIPERIDINYL)-11H-BENZO[5,6]CYCLOHEPTA[1,2-b]PYRIDINE

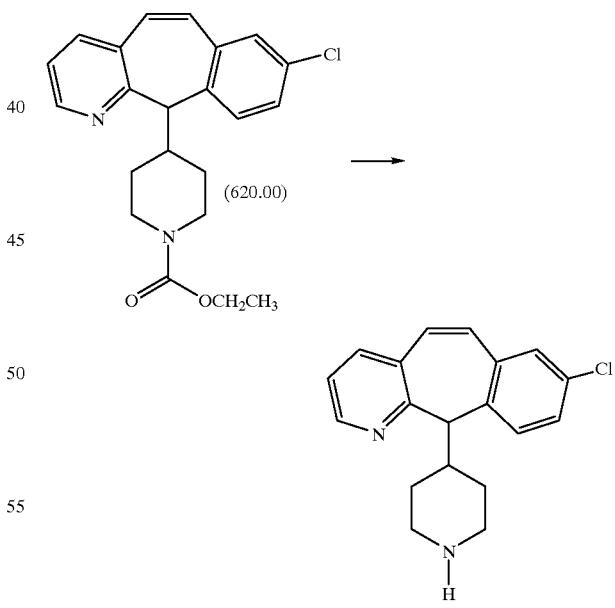

(620.00)

Hydrolyze compound 620.00 of Example 9 by dissolving in 50% aqueous $H_2SO_4$ (v/v) and heating to 900 to 100° C. for 16 h. The cooled acidic mixture was neutralized with 25% NaOH solution (w/v). The resulting mixture was extracted with EtOAc and the EtOAc extract was dried with $Na_2SO_4$. Filtration and evaporation of the EtOAc afforded the title compound ($MH^+$ 311).

B. 8-CHLORO-9-ETHYL-11-(4-PIPERIDINYL)-11H-BENZO-5,6]CYCLOHEPTA[1,2-b]PYRIDINE

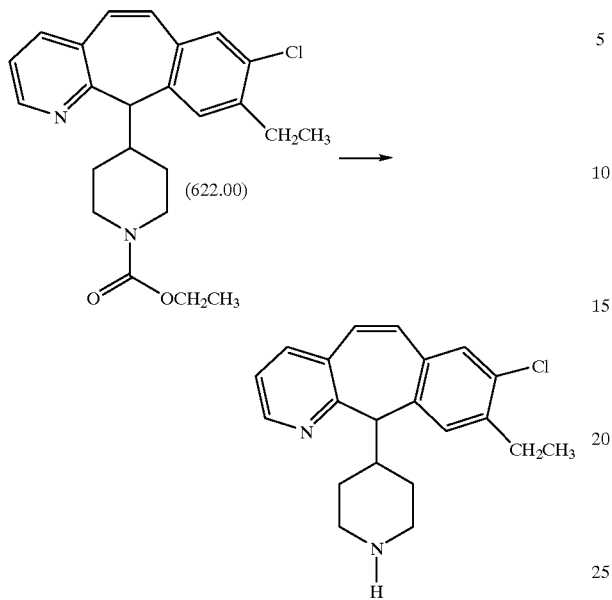

Hydrolyze compound 622.00 of Example 9 following the procedure described in Example 10A. (Decomposes between 205.7–215.4° C. heating 2–3° C. per minute).

C. 8-CHLORO-9-ETHYL-11-(1-(3-PYRIDYLOXY)CARBONYL-4-PIPERIDINYL)-1H-BENZO[5,6]CYCLOHEPTA[1,2-b]PYRIDINE

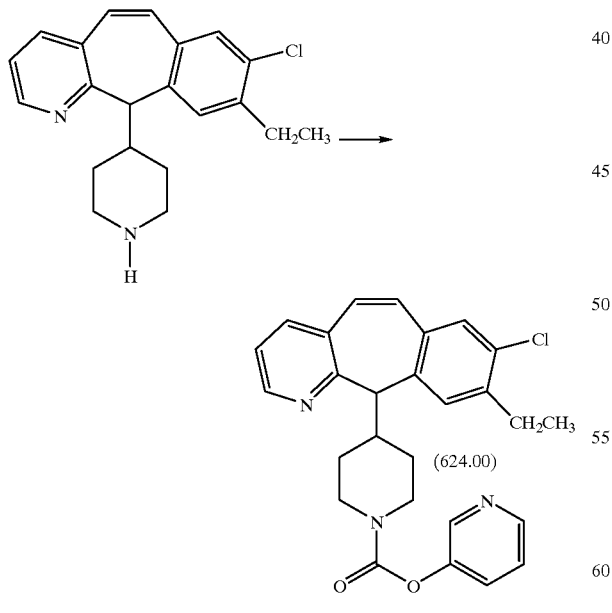

The title compound from Example 10B above was reacted with 3-pyridyl chloroformate as described in Example 6B above to give the title compound 624.00 (MH$^+$ 460).

EXAMPLE 11
8-CHLORO-11-(1-(3-PYRIDYLOXY)CARBONYL-4-PIPERIDINYL)-11H-BENZO[5,6]CYCLOHEPTA[1,2-b]PYRIDINE

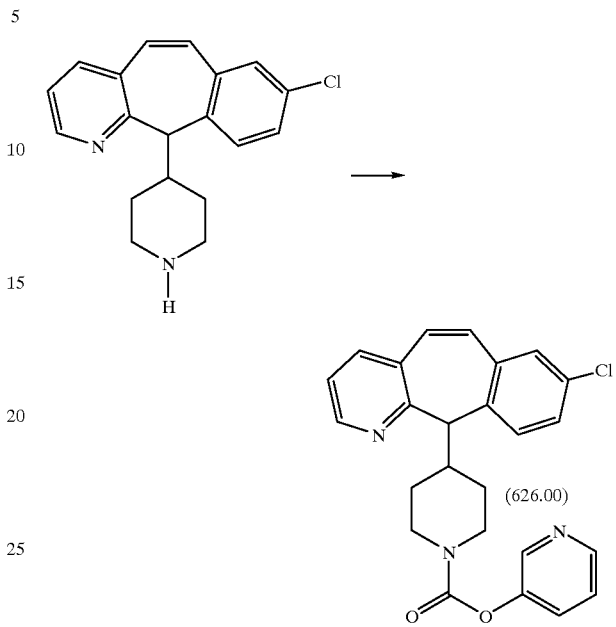

The title compound from Example 10A above was reacted with 3-pyridyl chloroformate as described in Example 6B above to give compound 626.00 (MH$^+$ 432, mp 102.1–103.9° C.).

EXAMPLE 12
A. 8-CHLORO-11-(1-ETHOXYCARBONYL-4-PIPERIDINYL)-11H-BENZO[5,6]CYCLOHEPTA[1,2-b]PYRIDINE-1-OXIDE

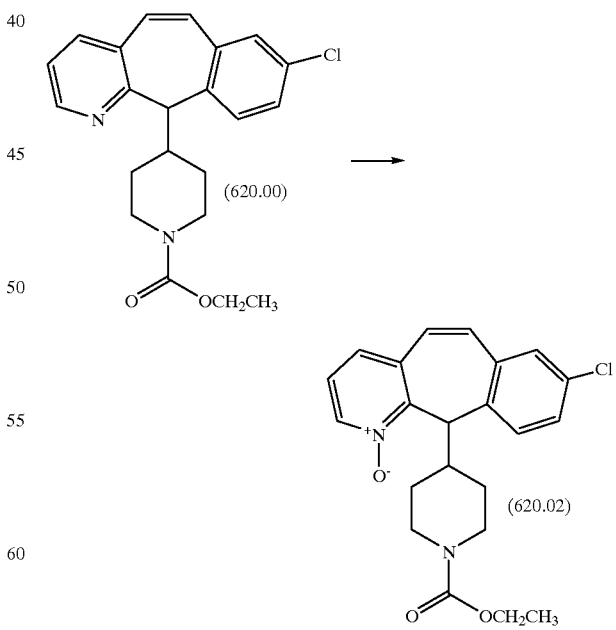

Compound 620.00 from Example 9 above (20.23 grams, 52.84 mmoles) was dissolved in CH$_2$Cl$_2$ (250 mL). MCPBA (1.25 equivalents) was added in one portion and this solution was stirred for 45 minutes. NaHSO₃ solution (20% w/v) was added and the biphasic mixture rapidly stirred for 30 minutes. The layers were separated and the organic layer was washed with saturated Na₂CO₃ solution and dried with Na₂SO₄. Filtration and evaporation afforded compound 620.02 (21 g, 99%, MH⁺ 399, mp 78.6–89.4° C.).

B. 4,8-DICHLORO-11-(1-ETHOXYCARBONYL-4-PIPERIDIN-YL)-11H-BENZO[5,6]CYCLOHEPTA[1,2-B]PYRIDINE (636.00) and 2,8-DICHLORO-11-(1-ETHOXYCARBONYL-4-PIPERIDIN-YL)-11H-BENZO[5,61CYCLOHEPTA[1,2-BIPYRFIDINE (640.00)

Compound 620.02 from Example 12A (21 grams, 53 mmoles) above was dissolved in anhydrous dichloroethane (250 mL) and the solution cooled to 0° C. POCl₃ (49.4 grams, 0.322 mole) was added dropwise to the dichloroethane solution over 15 minutes. After the POC₁₃ was added the reaction mixture was warmed to 45–50° C. and stirred for 18 h. Additional POCl₃ (8.2 grams) was added and the mixture heated to reflux for 9 h. The mixture was cooled and added to an ice cooled, stirred solution of NaOH (15% w/v). The resulting biphasic mixture was stirred rapidly for 18 h. The layers were separated and the aqueous layer was extracted with CH₂Cl₂. The combined organic layers were washed with water followed by brine and dried (Na₂SO₄). The mixture was filtered and evaporated, and the residue chromatographed on silica gel using a gradient of 25% EtOAc in hexane to 45% EtOAc in hexane as eluent. Compound 636.00 was obtained as a yellow solid (5.98 g), and compound 640.00 was obtained as a yellow solid (1.0 g, M⁺ 417, mp77.8–82.5° C.).

EXAMPLE 13

A. 4,8-DICHLORO-11-(4-PIPERIDINYL)-11H-BENZO[5,6]-CYLHEPTA[1,2-b]PYRIDINE

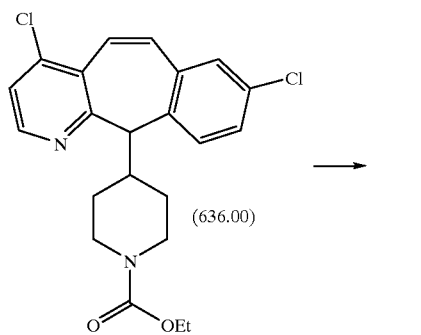

Compound 636.00 from Example 12B was hydrolyzed under the conditions described in Example 10A above to give the title compound (M⁺345).

B. 4,8-DICHLORO-11-(1-(3-PYRIDYLOXY)CARBONYL-4-PIPERIDINYL)-11H-BENZO[5,6]CYCLOHEPTA[1,2-b]PYRIDINE

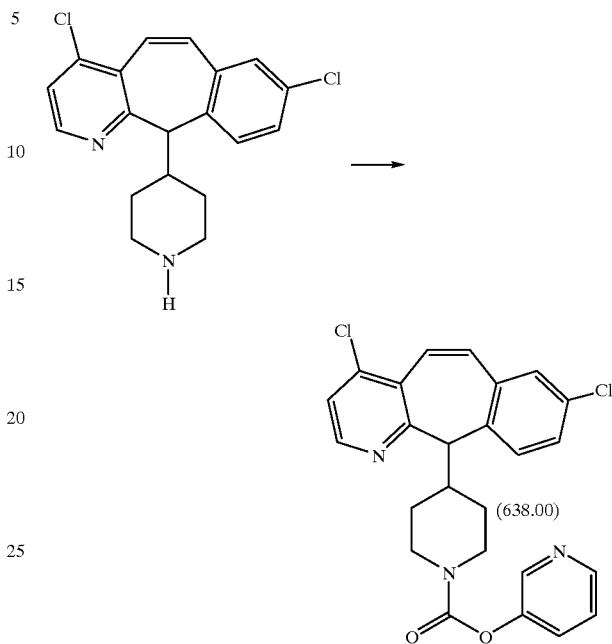

The title compound from Example 13A above was reacted with 3-pyridyl chloroformate as described in Example 6B above to give compound 638.00 (M⁺ 466).

EXAMPLE 14

4-(8-chloro-5,6-dihydro-11H-benzo[5,6]cyclohepta[12-b]-pyridin-11-ylidene)-1-piperinecarbothioic acid, S-phenyl ester

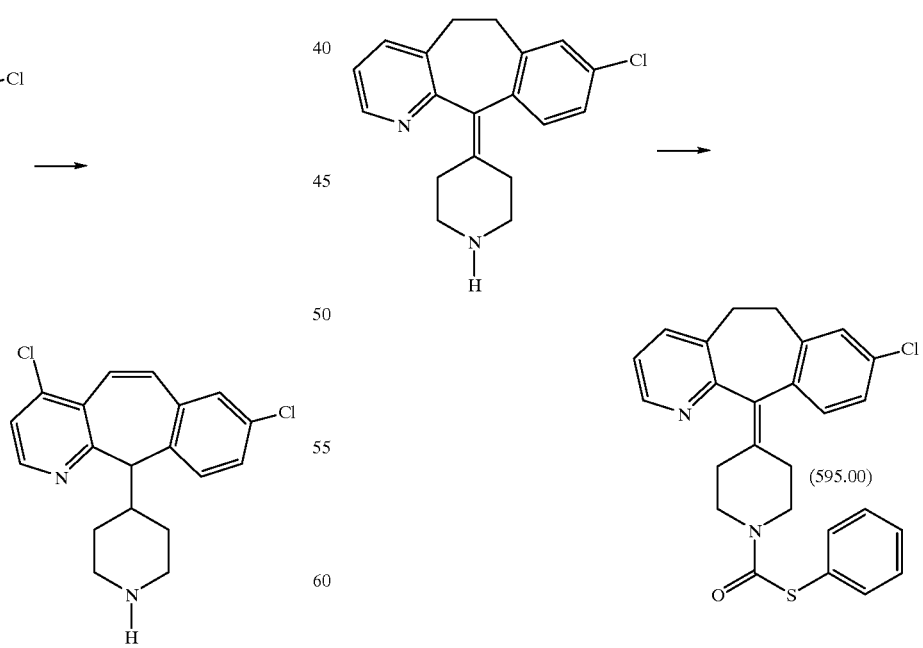

Dissolve the product of Preparative Example 1G (2 g, 6.71 mmole) in 25 ml of pyridine. To this add phenyl chlorothionoformate (1.2 ml, 6.96 mmole) and DMAP (0.2 g, 1.64 mmole). Heat to 50° C. for 4 hr followed by stirring at room temperature for 16 hr. Concentrate under vacuum,

EXAMPLE 15
ETHYL 4-[4-[(1H-BENZOTRIAZOL-1-YL)OXY]-8-CHLORO-5,6-DIHYDRO-11H-BENZO[5,6]CYCLOHEPTA[1,2-b]PYRIDIN-11-YLIDENE]-1-PIPERIDINE CARBAMATE

To a solution of compound 596.00 of Preparative Example 5 (1.5 grams) in dry DMF(20 mL) was added HOBT (1.5 grams). After stirring for 14 days at 25° C., NaH (0.84 grams, 60% in mineral oil) was added and after an additional 24 hours, the mixture was poured into water. Filtration provided compound 654.00 (Yield: 1.7 grams, 89%, mp=181.5–183.9° C., MH$^+$ 516).

EXAMPLE 16
ETHYL 4-[4-HYDROXY-8-CHLORO-5,6-DIHYDRO-11H-BENZO[5,6]CYCLOHEPTA[1,2-b]PYRIDIN-11-YLIDENE]-1-PIPERIDINE CARBOXYLATE

To a solution of compound 654.00 of Example 15 (0.15 grams) and glacial HOAc (5 mL) was added Zn dust (0.2 grams). After stirring at 25° C. for 1 hour, the mixture was filtered through celite and the filtrate concentrated in vacuo. The residue was diluted with EtOAc, washed with saturated aqueous NaHCO$_3$ and brine. The organic layer was separated, dried over MgSO$_4$ and concentrated in vacuo to give compound 646.00 (Yield: 0.11 grams, 95%, MH+ 399).

EXAMPLE 17
3-PYRIDYL 4-(4,8-DICHLORO-5,6-DIHYDRO-11H-BENZO[5,6]CYCLOHEPTA[1,2-b]PYRIDIN-11-YLIDENE)-1-PIPERIDINE CARBOXYLATE

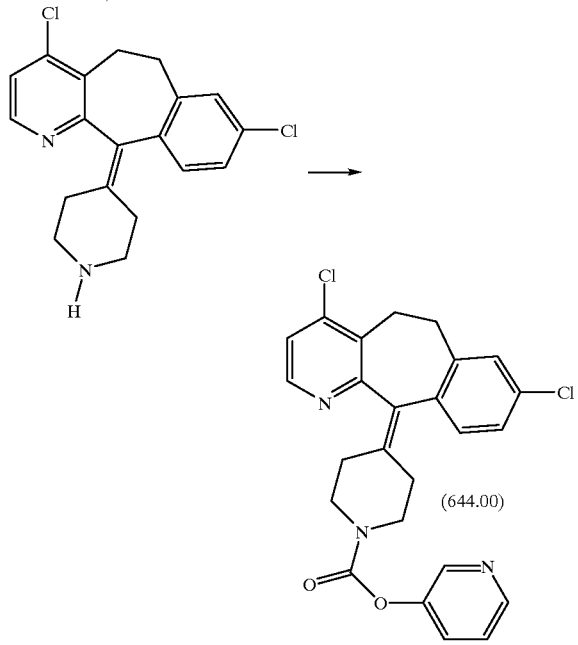

A portion of the stock solution of 3-pyridylchloroformate (62 mL of 0.144 M in pyridine) prepared as described in Example 6A and the 4,8-dichloro product from Preparative Example 4C (2.2 grams) were stirred at 25° C. for 6 days. The solution was evaporated to dryness and azeotroped with toluene. The residue was taken up in CH$_2$Cl$_2$ and washed with saturated aqueous NaHCO$_3$ and then water. The organic solution was dried over MgSO$_4$, filtered and evaporated to dryness. The residue was purified by flash column chromatography silica gel) using 3% MeOH-CH$_2$Cl$_2$ as eluent to give compound 644.00 (Yield: 1.6 grams, 54%, MH$^+$ 466).

EXAMPLE 18
3-PYRIDYL 4-[4-[(1H-BENZOTRIAZOL-1-YL)OXY]-8-CHLORO-5,6-DIHYDRO-11H-BENZO[5,6]CYCLOHEPTA[1,2-b]PYRIDIN-11-YLIDENE]-1-PIPERIDINE CARBOXYLATE

To a solution of compound 644.00 of Example 17 (1.42 grams) in dry DMF(50 mL) was added HOBT (3 grams), and NaH (0.4 g, 60% in mineral oil). The solution was stirred at 25° C. under nitrogen while being irradiated with a 200 Watt lamp for 60 hours. The reaction mixture was poured into 1N aqueous NaOH, and filtration provided compound 656.00 (Yield: 1.8 grams, 100%, MH$^+$ 565).

EXAMPLE 19
3-PYRIDYL 4-[4-HYDROXY-8-CHLORO-5,6-DIHYDRO-11H-BENZO[5,6]CYCLOHEPTA[1,2-b]PYRIDIN-11-YLIDENE]-1-PIPERIDINE CARBOXYLATE

To a solution of compound 656.00 of Example 18 (1.54 grams) and glacial HOAc (50 mL) was added Zn dust (1.8 grams). After stirring at 25° C. for 1 hour, the mixture was filtered through celite and the filtrate concentrated in vacuo. The residue was diluted with EtOAc, washed with saturated aqueous NaHCO$_3$ and brine. The organic layer was separated, dried over MgSO$_4$ and concentrated in vacuo to give compound 648.00 (Yield: 0.6 grams, 46%, MH$^+$ 448).

EXAMPLE 24
A. 8-CHLORO-6,11-DIHYDRO-11-(4-PIPERIDINYL)-5H-BENZO[5,6]CYCLOHEPTA[1,2-b]PYRIDINE (Product A) and 6,11-DIHYDRO-11-(4-PIPERIDINYL)-5H-BENZO[5,6]-CYCLOHEPTA[1,2-b]PYRIDINE (Product B)

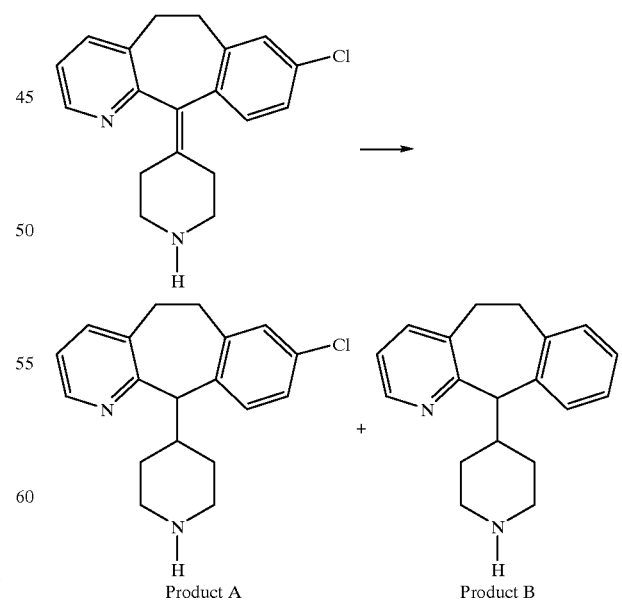

To a solution 66.27 g (0.21 mole) of 4-(8-chloro-5,6-dihydro-11H-benzo[5,6]cyclohepta(1,2-b]pyridin-11- ylidene)-piperidine (product from Preparative Example 1 Example, step G), in THF (1 L) was added LiAlH$_4$ (24.32 g, 0.64 mole) and the reaction mixture was heated to reflux overnight. The reaction mixture was then cooled to room temperature and ~3 L of Et$_2$O is added followed by dropwise addition of saturated Na$_2$SO$_4$ until a white gray precipitate forms. MgSO$_4$ was then added to the separated organic layer and stirred for 30 minutes. All the volatiles were then removed and the resulting crude mixture was chromatographed on a silica gel column eluting with 10% MeOH saturated with NH$_4$OH in CH$_2$Cl$_2$. The material obtained contained both the desired compound and the des-chloro compound. Separation on HPLC using reverse phase column and eluting with 40% MeOH-water afforded the desired compounds as white solids (Product A's mp=95.2–96.1° C., Product B's mp=145.1–145.7° C.).

B. ETHYL 4-(8-CHLORO-6,11-DIHYDRO-5H-BENZO-[5,6]CYCLOHEPTA(1,2-b)PYRIDIN-11-YL)-1-PIPERIDINE-CARBOXYLATE

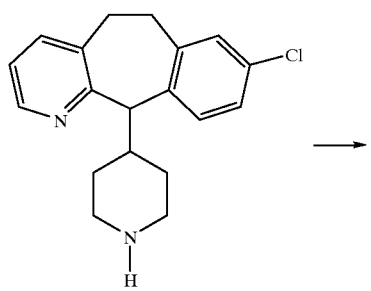

→

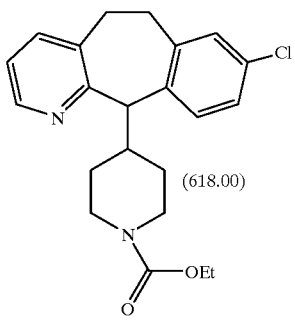

(618.00)

8-Chloro-6,11-dihydro-11-(4-piperidinyl)-5H-benzo[5,6] cyclohepta-[1,2-b]pyridine (product from Example 24A) (4.18 g, 13 mmol) was dissolved in toluene (175 mL). Ethyl chloroformate(11.6 g, 110 mmol, 10.2 mL) was then added and the reaction mixture was heated to ~120° C. overnight. All volatiles were stripped off and the crude product was purified on silica gel column eluting with 50% EtOAc-hexanes to give the title compound as a white solid(MH$^+$ 385).

EXAMPLE 28

By using the appropriately substituted chloroformate listed in Table 2 in place of ethyl chloroformate in step F of Preparative Example 1, and basically employing the same chemistry described in Example 1 F, the products in Table 2 are prepared. In most cases, the products are purified by flash chromatography.

TABLE 2

| Chloroformate | R$^{60}$ | Compound | MH$^+$ |
|---|---|---|---|
| Cl-C(O)-O-CH$_3$ | —CH$_3$ | 560.00 | 369 |
| Cl-C(O)-O-CH$_2$CH(CH$_3$)$_2$ | —CH$_2$CH(CH$_3$)$_2$ | 575.00 | 411 |
| Cl-C(O)-O-C$_6$H$_{13}$ | —C$_6$H$_{13}$ | 590.00 | 439 |

TABLE 2-continued

| Chloroformate | R⁶⁰ | Compound | MH⁺ |
|---|---|---|---|
| Cl-C(O)-O-C₈H₁₇ | —C₈H₁₇ | 585.00 | 468 |
| Cl-C(O)-O-phenyl | phenyl | 565.00 | 431 |
| Cl-C(O)-O-(4-Br-phenyl) | 4-Br-phenyl | 580.00 | 510 |
| Cl-C(O)-O-CH₂-phenyl | CH₂-phenyl | 570.00 | 445 |

EXAMPLE 29

ETHYL 4-[3-BROMO-4-HYDROXY-8-CHLORO-5,6-DIHYDRO-11H-BENZO[5,6]CYCLOHEPTA[1,2-b]PYRIDIN-11-YLIDENE]-1-PIPERIDINE CARBOXYLATE

To a solution of compound 646.00 from Example 16 (0.08 grams) and glacial HOAc (5 mL) was added a 2 M Br₂-HOAc solution (0.2 mL) at 25° C. under N₂. After 3 days, the solution was concentrated in vacuo, then neutralized with 1N aqueous NaOH and extracted with CH₂Cl₂. The organic phase was washed with brine, dried over anhydrous MgSO₄, and concentrated in vacuo to give compound 660.00 (0.02 grams, 23%, MH⁺ 477).

EXAMPLE 30

3-PYRIDYL 4-[3-BROMO-4-HYDROXY-8-CHLORO-5,6-DIHYDRO-11H-BENZO[5,6]CYCLOHEPTA[1,2-b]PYRIDIN-11-YLIDENE]-1-PIPERIDINE CARBOXYLATE

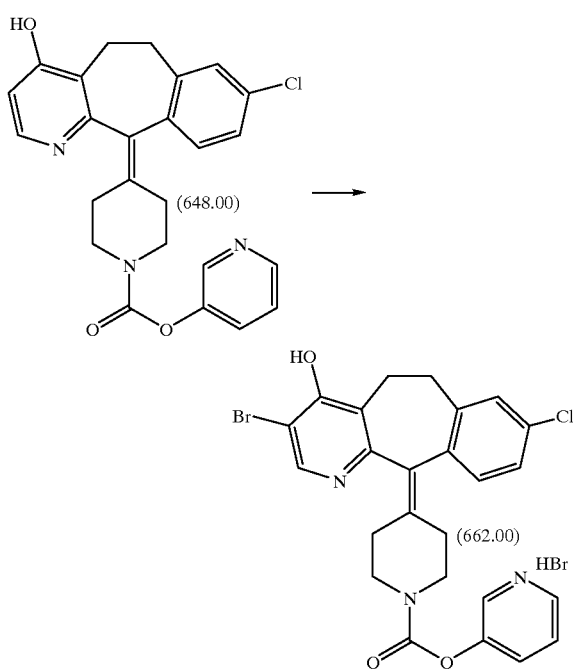

To a solution of compound 648.00 from Example 19 (0.02 grams) and glacial HOAc (1 mL) was added a 2 M $Br_2$-HOAc solution (0.04 mL) at 25° C. under $N_2$. After 10 minutes, water was added and an additional 3 drops of the $Br_2$-HOAc solution. The resulting solid was filtered and washed with water several times and dried to give compound 662.00 (0.02 grams, 92%, $MH^+$ 526).

EXAMPLE 31

A. 4-(8-CHLORO-3-NITRO-5,6-DIHYDRO-11H-BENZO[5,6]-CYCLOHEPTA[1,2-b]PYRIDIN-11-YLIDENE)-1-PIPERIDINE-1-CARBOXYLIC ACID ETHYL ESTER

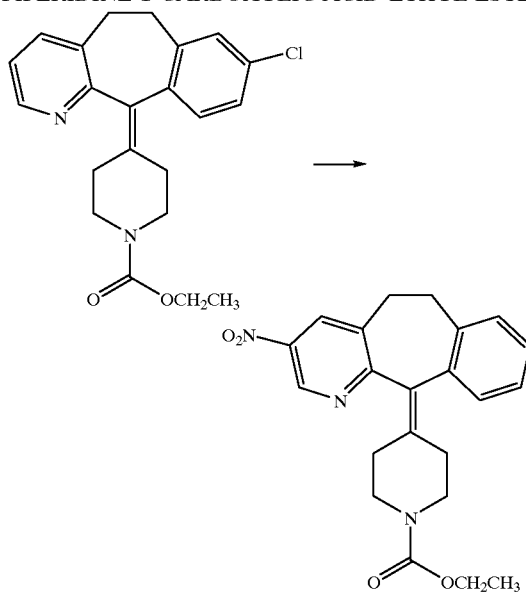

Tetrabutyl ammonium nitrate(4.98 g, 16.3 mmol) was dissolved in $CH_2Cl_2$(20 mL) and TFAA(3.12 g, 14.9 mmol, 2.1 mL) was then added. The solution was cooled to 0° C. and then added (by cannulation) to a solution of 4-(8-chloro-5,6-dihydro-11H-benzo[5,6]-cyclohepta[1,2-b]pyridin-11-ylidene)-1-piperidine-1-carboxylic aid ethyl ester (5.69 g, 14.9 mmol) in $CH_2Cl_2$ (35 mL) also cooled to 0° C. The reaction mixture was stirred at 0° C. for 3 h and then allowed to go to room temperature (25° C.) overnight. The reaction mixture was then extracted with saturated $NaHCO_3$ (60 mL) dried over $MgSO_4$ and concentrated to give a semi-solid material that was chromatographed on silica gel eluting first with 10% and then 20% EtOAc-hexane. Removal of the organic solvents gave the title compound in 44% yield as a light yellow solid. MP=90.4–91.0° C., $MH^+$ 428.

B. 4-(8-CHLORO-3-AMINO-5,6-DIHYDRO-11H-BENZO[5,6]-CYCLOHEPTA[1,2-b]PYRIDIN-11-YLIDENE)-1-PIPERIDINE-1-CARBOXYLIC ACID ETHYL ESTER

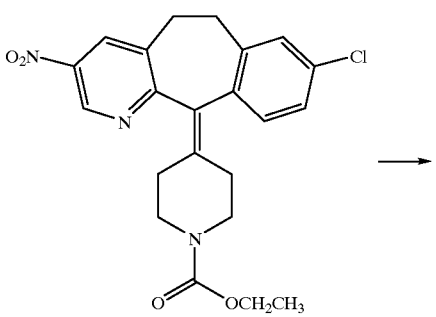

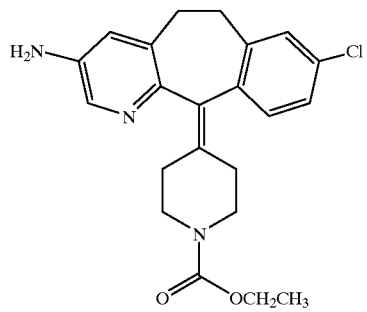

The title compound from Example 31A (5.99 g, 14 mmol) was dissolved in 85% aqueous EtOH. To this solution was added Fe filings (7.01 g, 125.57 mmol) and $CaCl_2$ (0.69 g, 6.29 mmol) and the reaction mixture was refluxed for 16 h. The reaction mixture was filtered through a bed of celite while hot and the celite was washed with hot EtOH (700 mL). The EtOH solution was then decolorized with activated charcoal (2.4 g) and then filtered through celite. EtOH was then rotary eavaporated to give the title compound in 100% yield as an off-white solid. MP=102.4–103.1° C., $MH^+$ 398.

C. 4-(8-CHLORO-3-BROMO-5,6-DIHYDRO-11H-BENZO[5,6]-CYCLOHEPTA[1,2-b]PYRIDIN-11-YLIDENE)-1-PIPERIDINE-1-CARBOXYLIC ACID ETHYLESTER

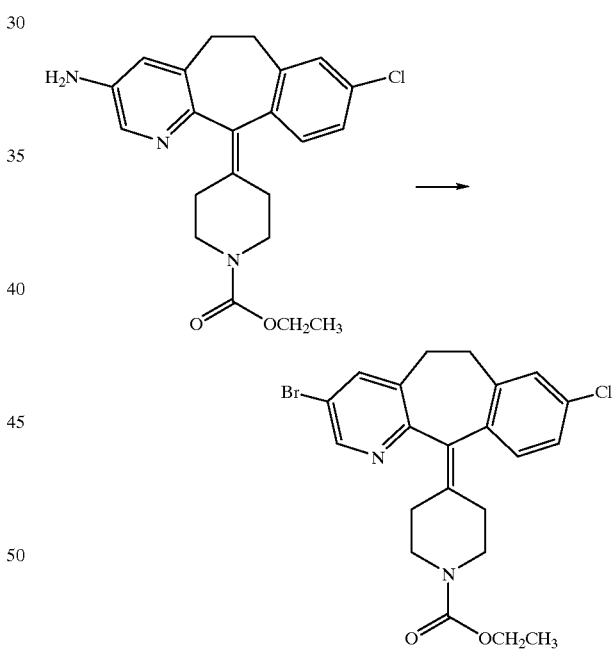

The title compound from Example 31B (3.00 g, 7.60 mmol) was dissolved in HBr (48%, 30 mL). The reaction mixture was cooled to −5° C. (ice-ethylene glycol bath) and $Br_2$ (2 mL) was added dropwise. The reaction mixture was stirred at −5° C. for 15 minutes. $NaNO_2$ (1.57 g, 22.8 mmol) dissolved in water (15 mL) was slowly added to the reaction mixture. The reaction mixture was then stirred for 45 minutes and then quenched with 40% NaOH to pH 10. The aqueous phase was then extracted with EtOAc (3×100 mL). Combined EtOAc fractions were dried over $NaSO_4$ and then concentrated to give the title compound in 83% yield as a light brown solid. Mp=146–148° C., MH+ 463.

EXAMPLE 32

A compound of formula:

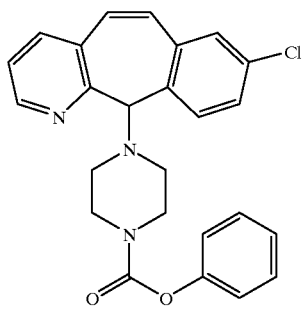

was prepared from the title compound of Preparative Example 10 by reaction with phenylchloroformate by essentially the same procedure as described in Example 4 in 89% yield, MH$^+$ 432.

EXAMPLE 33

A compound of the formula:

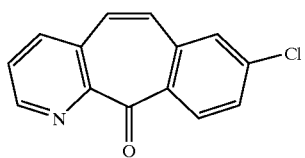

was reacted essentially as described in Example 2D–H to produce the intermediate

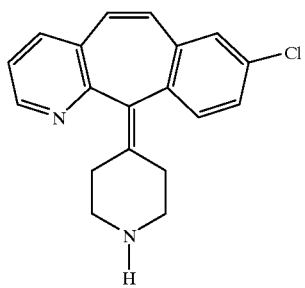

which intermediate was reacted with the title compound of Example 6A to give, by essentially the same procedure as described in Example 6B, the compound

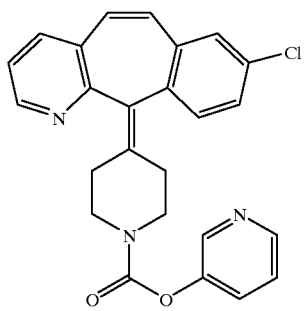

MH$^+$ 404. The starting ketone is a known compound which can be prepared by the process described in *The Journal of Organic Chemistry*, 1990, 55, pp. 3341–3350 by Piwinski, et al.

EXAMPLE 40

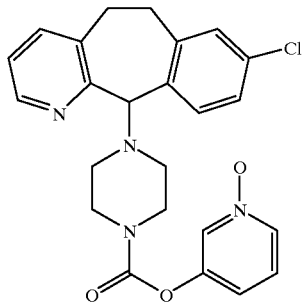

Combine 12 mL of dry $CH_2Cl_2$ and 12.58 mL (23.9 mmol) of a 28% solution of phosgene in toluene, cool to 0° C. under Ar atmosphere and slowly add (dropwise) a solution of 0.5 g (1.59 mmol) of the product of Preparative Example 7, Step C, 0.515 mL (6.36 mmol) of pyridine and 12 mL of dry $CH_2Cl_2$, over 0.75 hours, then warm the mixture to 12° C. over 0.5 hours. Purge excess phosgene with Ar then concentrate in vacuo to a residue. Add 10 mL of DMF, 0.515 mL of pyridine and 0.885 g (7.95 mmol) of 3-hydroxypyridine-1-N-oxide and stir at 25° C. for 18 hours. Dilute with $CH_2Cl_2$, wash with sat. $NaHCO_3$ (aqueous) and dry over $MgSO_4$. Concentrate in vacuo to a residue and chromatograph (silica gel, 1.5% (10% $NH_4OH$ in MeOH)/$CH_2Cl_2$) to give 0.186 g of the title compound. Mass Spec.: MH$^+$=451.3.

EXAMPLE 41

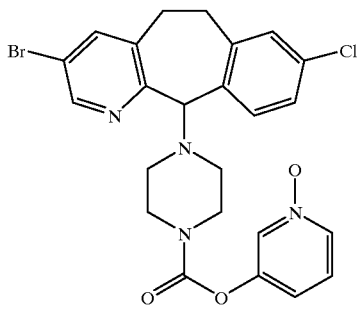

Combine 0.1 g (0.205 mmol) of the product of Preparative Example 12-A, 0.0463 g (0.205 mmol) of $ZnBr_2$, 0.0913 g (0.822 mmol) of 3-hydroxypyridine-1-N-oxide and 3 mL of dry DMF, and heat the mixture at 90° C. for 51 hours, then stir at 25° C. for 19 hours. Concentrate in vacuo to a residue and chromatograph (silica gel, 2% (10% $NH_4OH$ in MeOH)/$CH_2Cl_2$) to give 0.0812 g of the title compound. Mass Spec.: MH$^+$=531.1.

Using the starting compounds indicated and following essentially the same procedure as described for Example 41, the following compounds are obtained:

| Starting Compound | Product Compound | Analytical Data |
|---|---|---|
| 3-hydroxy-1-N-methylpiperidine and Preparative Example 12 | Example 41-A | Mass Spec.: MH⁺ = 455.25 |
| 3-hydroxy-1-N-methylpiperidine and Preparative Example 12-A | Example 41-B | Mass Spec.: MH⁺ = 533.15 |

EXAMPLE 42

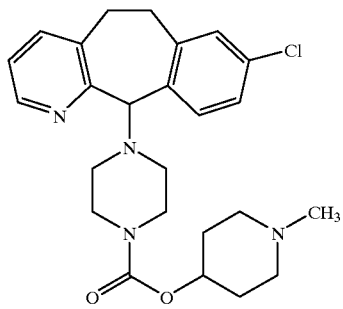

Combine 0.5 g (1.6 mmol) of the product of Preparative Example 7, Step C, 0.849 g (4.8 mmol) of the title compound of Preparative Example 13, and 10 mL of 1:1 pyridine/CH$_2$Cl$_2$, and stir at 25° C. for 19 hours. Workup as described for Example 4 and chromatograph (silica gel, 3% (10% NH$_4$OH in MeOH)/CH$_2$Cl$_2$) to give 0.5231 g of the title compound. Mass Spec.: MH⁺=455.25.

Using the starting compound indicated and following essentially the same procedure as described for Example 42, the following compounds are obtained:

| Starting Compound | Product Compound | Analytical Data |
|---|---|---|
| Preparative Example 11 | Example 42-A | Mass Spec.: MH⁺ = 533.15 |

ASSAYS

1. In vitro enzyme assays: Inhibition of farnesyl protein transferase and geranylgeranyl protein transferase.

Both farnesyl protein transferase (FPT) and geranylgeranyl protein transferase (GGPT) I were partially purified from rat brain by ammonium sulfate fractionation followed by Q-Sepharose (Pharmacia, Inc.) anion exchange chromatography essentially as described by Yokoyama et al (Yokoyama, K., et al., (1991), A protein geranylgeranyl-transferase from bovine brain: Implications for protein prenylation specificity, *Proc. Natl. Acad. Sci USA* 88: 5302–5306, the disclosure of which is incorporated herein by reference thereto). Human farnesyl protein transferase was also expressed in *E. coli*, using cDNA clones encoding both the α and β subunits. The methods used were similar to those published (Omer, C. et al., (1993), Characterization of recombinant human farnesyl protein transferase: Cloning, expression, farnesyl diphosphate binding, and functional homology with yeast prenyl-protein transferases, Biochemistry 32:5167–5176). Human farnesyl protein transferase was partially-purified from the soluble protein fraction of *E. coli* as described above the tricyclic farnesyl protein transferase inhibitors disclosed herein inhibited both human and rat enzyme with similar potencies. Two forms of val$^{12}$-Ha-Ras protein were prepared as substrates for these enzymes, differing in their carboxy terminal sequence. One form terminated in cysteine-valine-leucine-serine (Ras-CVLS) the other in cystein-valine-leucine-leucine (Ras-CVLL). Ras-CVLS is a substrate for the farnesyl protein transferase while Ras-CVLL is a substrate for geranylgeranyl protein transferase I. The cDNAs encoding these proteins were constructed so that the proteins contain an amino-terminal extension of 6 histidine residues. Both proteins were expressed in *Escherichia coli* and purified using metal chelate affinity chromatography. The radiolabelled isoprenyl pyrophosphate substrates, [$^3$H]farnesyl pyrophosphate and [$^3$H]geranylgeranyl pyrophosphate, were purchased from DuPont/New England Nuclear.

Several methods for measuring farnesyl protein transferase activity have been described (Reiss et al 1990, *Cell* 62: 81; Schaber et al 1990, *J. Biol. Chem.* 265: 14701; Manne et al 1990, *PNAS* 87: 7541; and Barbacid & Manne 1993, U.S. Pat. No. 5,185,248). The activity was assayed by measuring the transfer of [$^3$H]farnesyl from [$^3$H]farnesyl pyrophosphate to Ras-CVLS using conditions similar to those described by Reiss et al. 1990 (*Cell* 62: 81) The reaction mixture contained 40 mM Hepes, pH 7.5; 20 mM MgCl$_2$; 5 mM dithiothreitol; 0.25 μM [$^3$H]farnesyl pyrophosphate; 10 μl Q-Sepharose-purified farnesyl protein transferase; the indicated concentration of tricyclic compound or dimethylsulfoxide (DMSO) vehicle control (5% DMSO final); and 5 μM Ras-CVLS in a total volume of 100 μl. The reaction was allowed to proceed for 30 minutes at room temperature and then stopped with 0.5 ml of 4% sodium dodecyl sulfate (SDS) followed by 0.5 ml of cold 30% trichloracetic acid (TCA). Samples were allowed to sit on ice for 45 minutes and precipitated Ras protein was then collected on GF/C filter paper mats using a Brandel cell harvester. Filter mats were washed once with 6% TCA, 2% SDS and radioactivity was measured in a Wallac 1204 Betaplate BS liquid scintillation counter. Percent inhibition was calculated relative to the DMSO vehicle control.

The geranylgeranyl protein transferase I assay was essentially identical to the farnesyl protein transferase assay described above, with two exceptions: [$^3$H] geranylgeranylpyrophosphate replaced farnesyl pyrophosphate as the isoprenoid donor and Ras-CVLL was the protein acceptor. This is similar to the assay reported by Casey et al (Casey, P. J., et al., (1991), Enzymatic modification of proteins with a geranylgeranyl 35 isoprenoid, *Proc. Natl. Acad. Sci, USA* 88: 8631–8635, the disclosure of which is incorporated herein by reference thereto).

2. Cell-Based Assay: Transient expression of val$^{12}$-Ha-Ras-CVLS and val$^{12}$-Ha-Ras-CVLL in COS monkey kidney cells: Effect of farnesyl protein transferase inhibitors on Ras processing and on disordered cell growth induced by transforming Ras.

COS monkey kidney cells were transfected by electroporation with the plasmid pSV-SPORT (Gibco/BRL) containing a CDNA insert encoding either Ras-CVLS or Ras-CVLL, leading to transient overexpression of a Ras substrate for either farnesyl protein transferase or geranylgeranyl protein transferase I, respectively (see above).

Following electroporation, cells were plated into 6-well tissue culture dishes containing 1.5 ml of Dulbecco's-modified Eagle's media (GIBCO, Inc.) supplemented with 10% fetal calf serum and the appropriate farnesyl protein transferase inhibitors. After 24 hours, media was removed and fresh media containing the appropriate drugs was re-added.

48 hours after electroporation cells were examined under the microscope to monitor disordered cell growth induced by transforming Ras. Cells expressing transforming Ras become more rounded and refractile and overgrow the monolayer, reminiscent of the transformed phenotype. Cells were then photographed, washed twice with 1 ml of cold phosphate-buffered saline (PBS) and removed from the dish by scraping with a rubber policeman into 1 ml of a buffer containing 25 mM Tris, pH 8.0; 1 mM ethylenediamine tetraacetic acid; 1 mM phenylmethylsulfonyl fluoride; 50 μM leupeptin; and 0.1 μM pepstatin. Cells were lysed by homogenization and cell debris was removed by centrifugation at 2000×g for 10 min.

Cellular protein was precipitated by addition of ice-cold trichloroacetic acid and redissolved in 100 gl of SDS-electrophoresis sample buffer. Samples (5–10 μl) were loaded onto 14% polyacrylamide minigels (Novex, Inc.) and electrophoresed until the tracking dye neared the bottom of the gel. Proteins resolved on the gels were electroblotted onto nitrocellulose membranes for immunodetection.

Membranes were blocked by incubation overnight at 4° C. in PBS containing 2.5% dried milk and 0.5% Tween-20 and then incubated with a Ras-specific monoclonal antibody, Y13–259 (Furth, M. E., et al., (1982), Monoclonal antibodies to the p21 products of the transforming gene of Harvey murine sarcoma virus and of the cellular ras gene family, *J. Virol.* 43: 294–304), in PBS containing 1% fetal calf serum for one hour at room temperature. After washing, membranes were incubated for one hour at room temperature with a 1:5000 dilution of secondary antibody, rabbit anti-rat IgG conjugated to horseradish peroxidase, in PBS containing 1% fetal calf serum. The presence of processed and unprocessed Ras-CVLS or Ras-CVLL was detected using a colorimetric peroxidase reagent (4-chloro-1-naphthol) as described by the manufacturer (Bio-Rad).

3. Cell Mat Assay:

Normal human HEPM fibroblasts were planted in 3.5 cm dishes at a density of 5×10$^4$ cells/dish in 2 ml growth medium, and incubated for 3–5 d to achieve confluence. Medium was aspirated from each dish and the indicator tumor cells, T24-BAG4 human bladder carcinoma cells expressing an activated H-ras gene, were planted on top of the fibroblast monolayer at a density of $2 \times 10^3$ cells/dish in 2 ml growth medium, and allowed to attach overnight. Compound-induced colony inhibition was assayed by addition of serial dilutions of compound directly to the growth medium 24 h after tumor cell planting, and incubating cells for an additional 14 d to allow colony formation. Assays were terminated by rinsing monolayers twice with phosphate-buffered saline (PBS), fixing the monolayers with a 1% glutaraldehyde solution in PBS, then visualizing tumor cells by staining with X-Gal (Price, J., et al., Lineage analysis in the vertebrate nervous system by retrovirus-mediated gene transfer, Proc. Natl. Acad. Sci.84, 156–160 (1987)). In the colony inhibition assay, compounds were evaluated on the basis of two $IC_{50}$ values: the concentration of drug required to prevent the increase in tumor cell number by 50% ($tIC_{50}$) and the concentration of drug required to reduce the density of cells comprising the cell mat by 50% ($mIC_{50}$). Both $IC_{50}$ values were obtained by determining the density of tumor cells and mat cells by visual inspection and enumeration of cells per colony and the number of colonies under the microscope. The therapeutic index of the compound was quantitatively expressed as the ratio of $mIC_{50}/tIC_{50}$, with values greater than one indicative of tumor target specificity.

TABLE 3

FPT INHIBITION

| COMPOUND | FPT $IC_{50}$ ($\mu$M) | COS $IC_{50}$ ($\mu$M) |
|---|---|---|
| 500.00 | 1.6 | 22 |
| 515.00 | 37.6 | — |
| 520.00 | 10.4 | — |
| 525.00 | 37% at 50 $\mu$M, 79 | — |
| 530.00 | 3.7 | 15.4 |
| 540.00 | 7.0 | — |
| 545.00 | 7.1 | — |
| 550.00 | 7.2 | >20 |
| 555.00 | 37.8 | — |
| 560.00 | 17.6 | — |
| 565.00 | 0.84 | 6.7 |
| 570.00 | 8 | — |
| 575.00 | 4.4 | 9.9 |
| 580.00 | 0.2 | 17 |
| 585.00 | 0% at 43 $\mu$M | — |
| 590.00 | 80 | — |
| 595.00 | 0.24 | 5.1 |
| 596.00 | 10.5 | — |
| 600.00 | 1.28 | 6.9 |
| 602.00 | 34.1 | — |
| 604.00 | 10.5 | — |
| 608.00 | 0.82 | 3.9 |
| 610.00 | 0.5 | 3.0 |
| 612.00 | 0.8 | 4.8 |
| 614.00 | >20 | — |
| 618.00 | 1.22 | 20.5 |
| 620.00 | 8.9 | — |
| 622.00 | 10.5 | — |
| 636.00 | 7.4 | — |
| 642.00 | 2.17 | — |
| 644.00 | 1.03 | — |
| 646.00 | 30% @ 15 $\mu$M | — |
| 648.00 | 6.7 | — |
| 654.00 | 11.6 | — |
| 656.00 | 0.71 | — |
| 658.00 | 11.5 | — |
| 660.00 | 22% @ 13 $\mu$M | — |
| 662.00 | 3.8 | — |
| 664.00 | 1.46 | — |
| 666.00 | 10.8 | — |
| 668.00 | 32% @ 14 $\mu$M | — |
| 670.00 | 34% @ 17 $\mu$M | — |
| 672.00 | 8.2 | — |
| 674.00 | 12.9 | — |
| 676.00 | 0.53 | — |

TABLE 3-continued

FPT INHIBITION

| COMPOUND | FPT $IC_{50}$ ($\mu$M) | COS $IC_{50}$ ($\mu$M) |
|---|---|---|
| 678.00 | 50 | — |
| Example 32 | 0.88 | — |
| Example 33 | 1.46 | — |

Compound 525.00 and 678.00 are:

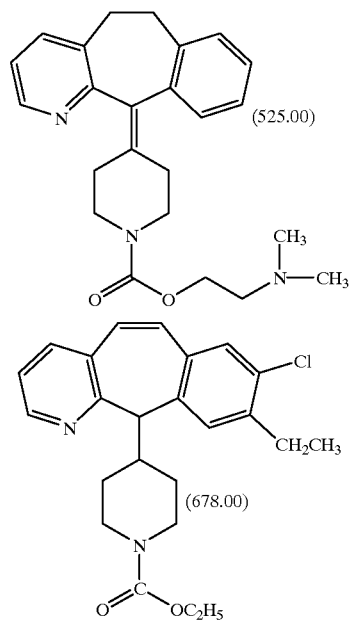

The GGPT $IC_{50}$ ($\mu$M) for compound 618.00 was >50.

TABLE 6

FPT INHIBITION

| COMPOUND | FPT $IC_{50}$ ($\mu$M) | COS $IC_{50}$ ($\mu$M) |
|---|---|---|
| (800.00) Example 40 | 3.7 | — |
| (801.00) Example 41 | 0.28 | — |
| (802.00) Example 42 | >1.3 35 (1.3) | — |
| (803.00) Example 42-A | 0.31 | >5.0 |
| (804.00) Example 41-A | 2.1 | — |
| (805.00) Example 41-B | 0.3 | — |

TABLE 4

INHIBITION OF TUMOR CELL GROWTH - MAT ASSAY

| COMPOUND | INHIBITION OF TUMOR CELL GROWTH ($IC_{50}$ $\mu$M) | INHIBITION OF NORMAL CELL GROWTH ($IC_{50}$ $\mu$M) |
|---|---|---|
| 500.00 | 25 | 25 |
| 515.00 | 75 | >100 |
| 530.00 | 12.5 | 100 |
| 550.00 | 18 | >50 |
| | 25 | >50 |
| 575.00 | 37 | >50 |

TABLE 4-continued

INHIBITION OF TUMOR CELL GROWTH - MAT ASSAY

| COMPOUND | INHIBITION OF TUMOR CELL GROWTH ($IC_{50}$ μM) | INHIBITION OF NORMAL CELL GROWTH ($IC_{50}$ μM) |
|---|---|---|
| 595.00 | 18 | >50 |
| 600.00 | 12.5 | 50 |
| 608.00 | 37 | >50 |
| 612.00 | 50 | >50 |
| 614.00 | 50 | >50 |
| 618.00 | >50 | >50 |
| 642.00 | 50 | >50 |
| Example 32 | 25 | 25 |

RESULTS

1. Enzymology:

The data demonstrate that the compounds of the invention are inhibitors of Ras-CVLS farnesylation by partially purified rat and human brain farnesyl protein transferase (FPT). The data also show that there are compounds of the invention which can be considered as potent ($IC_{50}$<10 μM) inhibitors of Ras-CVLS farnesylation by partially purified rat brain farnesyl protein transferase (FPT)—see Table 3.

The data also demonstrate that compounds of the invention are poorer inhibitors of geranylgeranyl protein transferase (GGPT) assayed using Ras-CVLL as isoprenoid acceptor. Tested compounds were inactive or weakly active as geranylgeranyl transferase inhibitors at 20 μg/ml. For example, compound 500.00 inhibits GGPT 7% at 50 μM and is at least 31-fold selective for FPT inhibition. For another example, Compound 530.00 is inactive against GGPT at 49 μM and is at least 13-fold selective for FPT inhibition. This selectivity is important for the therapeutic potential of the compounds used in the methods of this invention, and increases the potential that the compounds will have selective growth inhibitory properties against Ras-transformed cells.

2. Cell-Based: COS Cell and Cell Mat Assays

Immunoblot analysis of the Ras protein expressed in Ras-transfected COS cells indicated that the farnesyl transferase inhibitors of this invention inhibit Ras-CVLS processing, causing accumulation of unprocessed Ras (Table 3). For example, compounds 500.00 and 530.00 inhibit Ras-CVLS processing with $IC_{50}$ values of 22 and 15.4 μM, respectively. These results show that the compounds inhibit farnesyl protein transferase in intact cells and indicate their potential to block cellular transformation by activated Ras oncogenes. Microscopic and photographic examination of the Ras-transfected COS cells following treatment with compound 530.00 indicated that they also blocked phenotypic changes induced by expression of oncogenic Ras. Cells expressing oncogenicRas-CVLS overgrew the monolayer and formed dense foci of cells. This response to oncogenic Ras-CVLS was inhibited by compound 530.00 at both 20 and 6.6 μg/ml.

Compounds of this invention also inhibited the growth of Ras-transformed tumor cells in the Mat assay. For example, compound 530.00 inhibited with an $IC_{50}$ value of 12.5 μM. This compound only displayed cytotoxic activity against the normal cell monolayer at higher concentrations ($IC_{50}$ of 100 μM). Some compounds tested in this assay had little (515.00, 612.00, 614.00, 618.00 and 642.00) or no (500.00) selective antiproliferative activity against Ras-transformed cells versus normal cells.

In Vivo Anti-Tumor Studies:

Tumor cells ($5 \times 10^5$ to $8 \times 10^6$ of M27 [mouse Lewis lung carcinoma], A431 [human epidermal carcinoma] or SW620 [human colon adenocarcinoma (lymph node metastasis)]) are innoculated subcutaneously into the flank of 5–6 week old athymic nu/nu female mice. For the C-f-1 [mouse fibroblast transformed with c-fos oncogene] tumor model, 2 $mm^3$ tumor fragments are transplanted subcutaneously into the flank of 5–6 week old athymic nu/nu female mice. Tumor bearing animals are selected and randomized when the tumors are established. Animals are treated with vehicle (beta cyclodextran for i.p. or corn oil for p.o.) only or compounds in vehicle twice a day (BID) for 5 (1–5) or 7 (1–7) days per week for 2 (x2) or 4 (x4) weeks. The percent inhibition of tumor growth relative to vehicle controls are determined by tumor measurements. The results are reported in Table 5.

TABLE 5

In-Vivo Anti-Tumor Results

| s.c. Tumor | Route & Schedule | % Inhibition for 530.00 |
|---|---|---|
| M27 | po, BID, 1–7, x4 | 49 |
| A431 | po, BID, 1–5, x4 | 20.3 |
| A431 | po, BID, 1–5, x4 | 58.2 |
| C-f-1 | ip, BID, 1–5, x2 | 17.8 |
| C-f-1 | po, BID, 1–5, x4 | 69 |
| SW-620 | po, BID, 1–5, x4 | 73 |

Additional results for the compound of Formula 530.00 are: (a) in the SW620 cell line, at a dose of 100 MPK, for a schedule of po, 10/wk, x4 (10 times per week for 4 weeks), the average % tumor inhibition was 57; and (b) in the M27 cell line, at a dose of 100 MPK, for a schedule of po, 14/wk, x4 (14 times per week for 4 weeks), the average % tumor inhibition was 37.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

PHARMACEUTICAL DOSAGE FROM EXAMPLES

Example A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B

Capsules

| No. | Ingredients | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound selected from a compound of the formula:

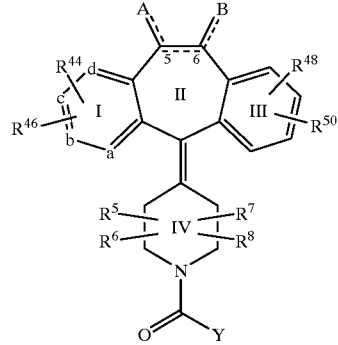

(1.3)

or a pharmaceutically acceptable salt or solvate thereof, wherein:

one of a, b, c and d represents N or $NR^9$ wherein $R^9$ is O—, —$CH_3$ or —$(CH_2)_nCO_2H$ wherein n is 1 to 3, and the remaining a, b, c and d groups represent $CR^1$ or $CR^2$;

$R^5$, $R^6$, $R^7$ and $R^8$ each independently represents H, —$CF_3$, alkyl or aryl, said alkyl or aryl optionally being substituted with —$OR^{10}$, —$SR^{10}$, —$N(R^{10})_2$, —$NO_2$, —$COR^{10}$, —$OCOR^{10}$, —$OCO_2R^{11}$, —$CO_2R^{10}$, or $OPO_3R^{10}$;

$R^{10}$ represents H, alkyl, aryl, or aralkyl;

$R^{11}$ represents alkyl or aryl;

the dotted line between carbon atoms 5 and 6 represents an optional double bond, such that when a double bond is present, A and B independently represent $R^{10}$, halo —$OR^{11}$, —$OCO_2R^{11}$ or —OC(O)$R^{10}$, and when no double bond is present between carbon atoms 5 and 6, A and B each independently represent $H_2$, —$(OR^{11})_2$; H and halo, dihalo, alkyl and H, (alkyl)$_2$, —H and —OC(O)$R^{10}$, H and —$OR^{10}$, =O, aryl and H, =$NOR^{10}$ or —O—$(CH_2)_p$—O— wherein p is 2, 3 or 4;

$R^{44}$ and $R^{46}$ are the same or different and each independently represents H, halo, —$CF_3$, —$OR^{10}$, —$COR^{10}$, —$SR^{10}$, —$N(R^{10})_2$, —$NO_2$, —$OC(O)R^{10}$, —$CO_2R^{10}$, —$OCO_2R^{11}$, benzotriazol-1-yloxy, CN, alkynyl, alkenyl or alkyl, said alkyl or alkenyl group optionally being substituted with halo, —$OR^{10}$ or —$CO_2R^{10}$;

$R^{48}$ and $R^{50}$ are the same or different and each independently represents any of the substituents of $R^{44}$ and $R^{46}$;

Y represents —$OR^{52}$ or —$SR^{70}$;

$R^{52}$ represents aralkyl, or aryl;

$R^{70}$ represents aryl and;

the dotted line between carbons 5 and 6 represent an optional double bond; and with the provisos that: (a) when Y represents —$OR^{52}$, and when there is a single bond between carbon atoms 5 and 6, and when both $R^{44}$ and $R^{46}$ are hydrogen, and when both $R^{48}$ and $R^{50}$ are H, then $R^{52}$ is not phenyl.

2. The compound of claim 1 wherein a represents N and the remaining b, c, and d groups represent carbon; each $R^{44}$ and $R^{46}$ is independently selected from H, —$CF_3$, halo, benzotriazol-1yloxy or $C_1$ to $C_4$ alkyl; each $R^{48}$ and $R^{50}$ are the same or different and each independently represents H or halo; $R^5$, $R^6$, $R^7$ and $R^8$ each independently represents H; when the dotted line between carbon atoms 5 and 6 represents a double bond, then A and B independently represent H, and when no double bond is present between carbon atoms 5 and 6, then A and B each independently represent $H_2$.

3. The compound of claim 2 wherein Y represents —$OR^{52}$; $R^{44}$ and $R^{46}$ are independently selected from H, halo, benzotriazol-1yloxy or $C_1$ to $C_4$ alkyl; $R^{48}$ is Cl at the C-8 position; $R^{50}$ is H; and $R^{52}$ represents phenyl, or substituted phenyl.

4. The compound of claim 3 wherein $R^{44}$ and $R^{46}$ are independently selected from H, Br, Cl or methyl.

5. The compound of claim 2 wherein Y is —$SR^{70}$; $R^{44}$ and $R^{46}$ are independently selected from H, halo, benzotriazol-1 yloxy or $C_1$ to $C_4$ alkyl; $R^{48}$ is Cl at the C-8 position; $R^{50}$ is H; and $R^{70}$ represents phenyl, or substituted phenyl.

6. The compound of claim 5 wherein $R^{44}$ and $R^{46}$ are independently selected from H, Br, Cl or methyl.

7. The compound of claim 1 selected from a compound of the structure:

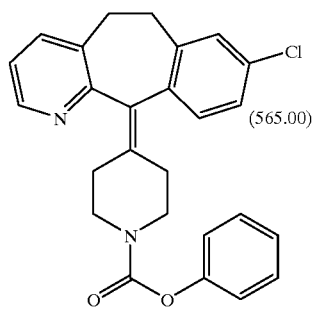

(565.00)

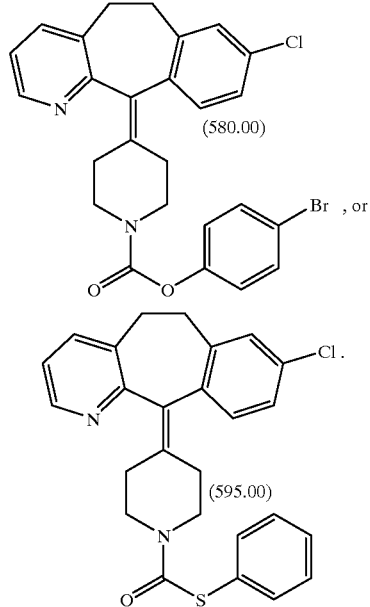

(580.00)

(595.00)

8. A pharmaceutical composition comprising a pharmaceutically acceptable carrier and an effective amount of a compound of claim 1.

9. A compound of the formula:

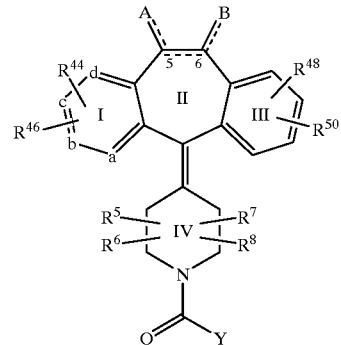

(1.3)

or a pharmaceutically acceptable salt or solvate thereof, wherein:

one of a, b, c and d represents N or $NR^9$ wherein $R^9$ is O—, —$CH_3$ or —$(CH_2)nCO_2H$ wherein n is 1 to 3, and the remaining a, b, c and d groups represent $CR^1$ or $CR^2$;

$R^5$, $R^6$, $R^7$ and $R^8$ each independently represents H, —$CF_3$, alkyl or aryl, said alkyl or aryl optionally being substituted with —$OR^{10}$, —$SR^{10}$, —$N(R^{10})_2$, —$NO_2$, —$COR^{10}$, —$OCOR^{10}$, —$OCO_2R^{11}$, —$CO_2R^{10}$, or $OPO_3R^{10}$;

$R^{10}$ represents H, alkyl, aryl, or aralkyl;

$R^{11}$ represents alkyl or aryl;

the dotted line between carbon atoms 5 and 6 represents an optional double bond, such that when a double bond is present, A and B independently represent —$R^{10}$, halo —$OR^{11}$, —$OCO_2R^{11}$ or —$OC(O)R^{10}$, and when no double bond is present between carbon atoms 5 and 6, A and B each independently represent $H_2$, —$(OR^{11})_2$; H and halo, dihalo, alkyl and H, (alkyl)$_2$, —H and —OC(O)$R^{10}$, H and —O$R^{10}$, =O, aryl and H, =NO$R^{10}$ or —O—(CH$_2$)$_p$—O— wherein p is 2, 3 or 4;

$R^{44}$ and $R^{46}$ are the same or different and each independently represents H, halo, —CF$_3$, —O$R^{10}$, —CO$R^{10}$, —S$R^{10}$, —N($R^{10}$)$_2$, —NO$_2$, —OC(O)$R^{10}$, —CO$_2$$R^{11}$, benzotriazol-1-yloxy, CN, alkynyl, alkenyl or alkyl, said alkyl or alkenyl group optionally being substituted with halo, —O$R^{10}$ or —CO$_2$$R^{10}$;

$R^{48}$ and $R^{50}$ are the same or different and each independently represents any of the substituents of $R^{44}$ and $R^{46}$;

Y represents —S$R^{70}$;

$R^{70}$ represents aryl; and the dotted line between carbons 5 and 6 represent an optional double bond.

10. The compound of claim 9 wherein a represents N and the remaining b, c, and d groups represent carbon; each $R^{44}$ and $R^{46}$ is independently selected from H, —CF$_3$, halo, benzotriazol-1yloxy or C$_1$ to C$_4$ alkyl; each $R^{48}$ and $R^{50}$ are the same or different and each independently represents H or halo; $R^5$, $R^6$, $R^7$ and $R^8$ each independently represents H; when the dotted line between carbon atoms 5 and 6 represents a double bond, then A and B independently represent H, and when no double bond is present between carbon atoms 5 and 6, then A and B each independently represent H$_2$.

11. The compound of claim 10 wherein $R^{44}$ and $R^{46}$ are independently selected from H, halo, benzotriazol-1yloxy or C$_1$ to C$_4$ alkyl; $R^{48}$ is Cl at the C-8 position; $R^{50}$ is H; and $R^{70}$ represents phenyl, or substituted phenyl.

12. The compound of claim 11 wherein $R^{44}$ and $R^{46}$ are independently selected from H, Br, Cl or methyl.

13. The compound of claim 9 having the formula:

(595.00)

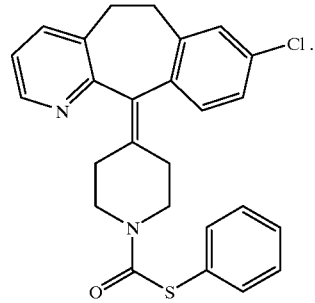

14. A pharmaceutical composition comprising a pharmaceutically acceptable carrier and an effective amount of a compound of claim 9.

* * * * *